(12) United States Patent
Kennedy et al.

(10) Patent No.: US 10,890,592 B2
(45) Date of Patent: Jan. 12, 2021

(54) AUTOMATED SAMPLE QUALITY ASSESSMENT

(71) Applicant: Metabolon, Inc., Morrisville, NC (US)

(72) Inventors: Adam D. Kennedy, Durham, NC (US); Matthew W. Mitchell, Durham, NC (US); Meredith V. Brown, Durham, NC (US); Kay A. Lawton, Raleigh, NC (US); Shaun Lonergan, Morrisville, NC (US); Jacob Wulff, Morrisville, NC (US)

(73) Assignee: Metabolon, Inc., Morrisville, NC (US)

( * ) Notice: Subject to any disclaimer, the term of this patent is extended or adjusted under 35 U.S.C. 154(b) by 192 days.

(21) Appl. No.: 15/772,834

(22) PCT Filed: Nov. 3, 2016

(86) PCT No.: PCT/US2016/060245
§ 371 (c)(1),
(2) Date: May 2, 2018

(87) PCT Pub. No.: WO2017/079384
PCT Pub. Date: May 11, 2017

(65) Prior Publication Data
US 2018/0321267 A1 Nov. 8, 2018

Related U.S. Application Data

(60) Provisional application No. 62/250,627, filed on Nov. 4, 2015.

(51) Int. Cl.
*G16B 50/00* (2019.01)
*G01N 33/48* (2006.01)
(Continued)

(52) U.S. Cl.
CPC ....... *G01N 35/00613* (2013.01); *G01N 33/48* (2013.01); *G01N 33/492* (2013.01);
(Continued)

(58) Field of Classification Search
CPC .. G16B 99/00; G16B 50/00; G01N 35/00613; G01N 33/48; G01N 33/492; G01N 33/50;
(Continued)

(56) References Cited

U.S. PATENT DOCUMENTS

2004/0248106 A1 12/2004 Leonard et al.
2010/0212675 A1 8/2010 Walling et al.
(Continued)

FOREIGN PATENT DOCUMENTS

| JP | 2012513221 A | 6/2012 |
|---|---|---|
| JP | 2014531046 A | 11/2014 |
| WO | 2013164278 A1 | 11/2013 |
| WO | 2014125443 A1 | 8/2014 |
| WO | 2015145387 A1 | 10/2015 |

OTHER PUBLICATIONS

PCT, International Search Report and Written Opinion in PCT/US16/60245 dated Mar. 9, 2017.
(Continued)

*Primary Examiner* — Brian J. Sines
(74) *Attorney, Agent, or Firm* — NK Patent Law

(57) ABSTRACT

A method of assessing the quality of a biological sample while maintaining the viability of the biological sample for intended use analysis is described herein. The method includes analyzing a biological sample obtained from a subject for an intended use, assessing the quality of the biological sample using one or more biomarkers of sample quality, and simultaneously performing intended use analysis on the same sample. Assessing the quality of the sample can include assessing compliance with sample handling protocols and assessing subject compliance.

21 Claims, 12 Drawing Sheets

(51) Int. Cl.
*G01N 33/50* (2006.01)
*G01N 33/66* (2006.01)
*G01N 33/68* (2006.01)
*G01N 33/92* (2006.01)
*G01N 35/00* (2006.01)
*G01N 33/53* (2006.01)
*G16B 99/00* (2019.01)
*G01N 33/49* (2006.01)

(52) U.S. Cl.
CPC ......... *G01N 33/50* (2013.01); *G01N 33/5308* (2013.01); *G01N 33/66* (2013.01); *G01N 33/68* (2013.01); *G01N 33/92* (2013.01); *G16B 50/00* (2019.02); *G16B 99/00* (2019.02); *G01N 2560/00* (2013.01); *G01N 2570/00* (2013.01)

(58) Field of Classification Search
CPC .... G01N 33/5308; G01N 33/66; G01N 33/68; G01N 33/92; G01N 2560/00; G01N 2570/00
See application file for complete search history.

(56) References Cited

U.S. PATENT DOCUMENTS

| 2010/0304989 | A1* | 12/2010 | Von Hoff | C12Q 1/6874 |
| | | | | 506/9 |
| 2013/0103321 | A1 | 4/2013 | Riel-Mehan et al. | |
| 2013/0286038 | A1* | 10/2013 | Kamath | G06K 9/00134 |
| | | | | 345/592 |
| 2013/0287283 | A1* | 10/2013 | Kamath | G06K 9/0014 |
| | | | | 382/133 |

OTHER PUBLICATIONS

EPO; Extended European Search Report for European Patent Application No. 16862931.9 dated May 21, 2019, 8 pages.
WIPO; International Preliminary Report on Patentability for International Patent Application No. PCT/US2016/060245 dated May 8, 2018, 8 pages.
JPO; Office Action for Japanese Patent Application No. 2018-543033 dated Sep. 29, 2020, 24 pages.

* cited by examiner

AUTOMATED SAMPLE QUALITY ASSESSMENT

CROSS-REFERENCE TO RELATED APPLICATIONS

This application is a U.S. National Stage application of International Application No. PCT/USS2016/060245, filed on 3 Nov. 2016, which claims the benefit of U.S. Provisional Patent Application No. 62/250,627, filed Nov. 4, 2015, the entire contents of which are all hereby incorporated herein by reference.

FIELD

The invention generally relates to a system, method and apparatus to assess the quality of a sample using small molecule biomarkers indicative of sample quality parameters and methods based on the same.

BACKGROUND

Metabolomics has been widely and successfully used to identify biomarkers for various indications. Obtaining interpretable, high quality data for any application, including metabolomics analysis, depends on starting with a good study design and high quality samples, free of artifacts due to mishandling the samples or lack of subject compliance. Currently, samples may be visually inspected prior to analysis to remove samples with obvious quality issues such as temperature or sample volume. In some cases, samples can be visually identified as sub-optimal due to a physical change in the appearance of the sample. For example visual inspection of plasma or serum samples may reveal macrohematuria, a red color from hemolysis, (high amount of red blood cell lysis) or turbidity from lipemia (high lipid content) in a sample. However, small amounts of hemolysis (e.g., micro-hematuria) or other perturbations to the sample may not be recognizable by visual inspection.

In sample types other than blood-based samples such as urine or tissue, visual inspection reveals little regarding sample quality. Furthermore, levels of metabolites in a sample may be affected by sample handling including sample collection, processing and storage conditions such as collection tubes and tube additives, processing time from collection, processing incubation temperature, time in storage, storage temperature, freeze-thaw cycles, and subject compliance such as fasting status, medication and supplement status, smoking status, and diet and exercise compliance. Protocol violations in sample handling and/or subject compliance, in turn, may impact the utility or suitability of the sample for subsequent analysis. The ability to monitor sample acquisition and assess samples for protocol compliance regarding handling and subject compliance could ensure that samples meet quality criteria or, those samples that fail one or more criteria are removed from analysis or the analysis is modified appropriately. A method to measure and report parameters affecting sample quality is beneficial.

While sample quality parameters exist for evaluating some effects of pre-analytical processing variations in metabolomics-based research (Kamlage, et al. *Clinical Chemistry.* 60:2, 399-412 (2014)), these parameters do not take into account subject compliance. Having quality parameters to evaluate subject compliance is important for studies such as clinical trials where failing to comply with a treatment regimen could affect the results of the trial or could pose a threat to subject safety. For example, non-compliance with a fasting protocol may affect results of many types of studies, including biomarker discovery and development. In addition, compliance for diagnostic tests may be important to obtaining valid results. A method to assess the quality of a sample that includes quality parameters addressing sample handling and subject compliance, and the identification of metabolite biomarkers useful in making the assessment, is needed.

The method described herein to assess the quality of a sample for studies involving the measurement of multiple small molecule analytes (e.g., metabolomics studies) represents an improvement over current methods for assessing sample quality. Current methods require a separate quality analysis on a subset of samples intended for a larger metabolomics study. The quality assessment is performed on only a few samples, and then the quality of all samples is extrapolated from that assessment. The method described herein performs quality assessment on all samples in the study simultaneously with the intended use analysis and does not require a separate sample or sample run to address sample quality. In this way, the amount of sample required is minimized, confidence that all samples meet quality criteria is assured, and the resulting data is of acceptable quality. Further, since the quality of each sample is assessed, variations observed in individual samples, such as variations due to compliance with a fasting or medication protocol, can be assessed and the need for additional or modified analysis can be determined and appropriately addressed. Current methods discourage the further use of samples for which insufficient quality has been determined. The method described herein assesses the quality of each sample, and individual samples that do not meet specific sample quality parameters can be flagged for further analysis. Thus, the entire sample set does not need to be discarded or removed from the analysis. Included in the method, the individual sample quality parameters identified as affected are reported. This assessment provides the investigator with information relating to which aspect(s) of the handling and/or compliance protocols may have been violated.

SUMMARY

Described herein are biomarkers of sample quality and systems, methods, and apparatuses of using the biomarkers to assess sample quality. Sample quality parameters are evaluated to assess if a sample is in compliance with a protocol. The methods and markers may be used to assess the quality of archival samples which may have been collected and stored for extended periods of time and for which handling protocols and subject compliance and requirement protocols are uncertain or unavailable. Protocol compliance may include sample handling from collection to processing to storage, as well as subject compliance with protocols prior to sample collection. The metabolic profiling of samples and sample quality biomarkers can be used to assess protocol compliance associated with sample handling. Examples of criteria associated with sample handling include sample collection, collection tubes, collection tube additives, sample processing time, processing incubation temperature, time in storage, storage temperature, and freeze-thaw cycles. The metabolic profiling of samples and sample quality biomarkers can also be used to assess subject compliance with a protocol. Examples of criteria associated with subject protocol compliance include fasting status, medication and supplement status, smoking status, diet, and exercise compliance.

Some embodiments described herein include systems, methods and apparatuses that employ metabolic profiling to assess sample quality simultaneously with performing biochemical analysis or metabolic profiling analysis of the same sample according to the intended use for the sample (e.g., clinical use or experimental use). The simultaneous survey of the biological sample may include automatically generating a metabolic profile of the biological sample and automatically statistically analyzing the resulting metabolic profile data to identify small molecules that are statistical outliers (i.e., aberrant) and can serve as sample quality biomarkers. As will be shown in the below examples, the generated metabolic profile of a sample and automated statistical analysis of the generated metabolic profile can uncover aberrant levels of small molecule sample quality biomarkers that aid in assessing the quality of the sample to determine if the sample was handled in compliance with a protocol and/or if the subject from whom the sample was collected was in compliance with a protocol (e.g., fasted). A visualization of the results of the automated statistical analysis of the generated metabolic profile may be provided to aid in assessing aberrant levels of small molecule sample quality biomarkers and/or perturbed or aberrant biochemical pathways that result from protocol non-compliance. In some embodiments, a list of one or more possible affected sample quality parameters associated with the identified aberrant sample quality biomarkers may be displayed. A list of recommended approaches for evaluating the sample may also be provided.

Automatic sample quality assessment is enabled by interrogation of sample quality biomarker levels in the sample. The sample quality assessment results can be reported as a Quality Assessment (QA) status. The sample quality biomarkers enable a user to distinguish biochemical changes due to a disease or disorder (e.g., clinical analyses) or due to experimental design (e.g., biomarker discovery analyses) from artifacts due to unacceptable sample quality. Thus, sample quality biomarkers allow a user to determine (or aid a user in determining) whether biochemical changes identified in a sample are indicative of a clinical or experimental result or of an issue with sample quality. The QA may include identifying and providing a list of affected sample quality parameters, identifying at least one intended use associated with one or more of the aberrant sample quality biomarkers, and/or providing a list of recommended approaches for evaluating the sample. The assessment allows for more than a simple inclusion/exclusion decision by providing information for further analysis of the sample based on the affected biomarkers and sample quality parameters. For example, in one aspect, the quality assessment may provide a recommendation for the application of a correction factor to one or more biomarkers before using the one or more biomarkers in an assessment. In another aspect, the quality assessment may provide a recommendation to eliminate certain biomarkers or biochemical pathways from the analysis. In another aspect, the quality assessment may provide a recommendation to substitute one biomarker with a different biomarker for a certain biochemical pathway.

The QA may include using the measured levels of one or more biomarkers in a composite score. The quality criteria can be adjusted by the experimentalist or clinician based upon the intended use of the sample, and the criteria may be selected from one or more quality parameters (e.g., sample processing time, sample storage temperature, sample freeze/thaw, time for plasma separation from whole blood, fasting status, medication status, smoking status, exercise compliance).

The quality assessment does not require a separate analysis or a separate sample; instead, it is performed simultaneously with the experimental or informational analysis. The simultaneous assessment of sample quality with the experimental or informational analysis has a number of advantages, including but not limited to, the following: reduced workload since it is not necessary to produce, process and analyze a separate "sample quality aliquot" from the analytical samples for QA purposes; reduced time for analysis; reduced costs associated with running and maintaining the instruments; reduced costs of goods (e.g., reagents, disposables, etc.); more data (and more useful data) may be obtained from the analyzed samples; and fewer samples may be discarded. The methods assess the quality of all samples rather than a selected subset of samples so each sample is associated with a QA. The QA would provide much needed clinical utility in identifying outliers (potential protocol violations) in a study based on the physical collection and handling of samples as well as subject compliance. These assessments would be more accurate and more sensitive than qualitative visual assessments. Further, simultaneous assessment of sample quality enables improvements in efficiency.

In some aspects, the quality assessment is partially automated. In some aspects, the quality assessment is fully automated.

In one embodiment a method is provided for assessing a sample for sample quality by surveying the sample for the level(s) of sample quality biomarkers by statistical analysis to identify aberrant sample quality biomarkers in said sample, listing aberrant sample quality biomarkers, and providing a sample quality assessment. In some embodiments the assessment is comprised of a composite score.

In one embodiment a method is provided for assessing a sample for sample quality by surveying the sample for the level(s) of sample quality biomarkers by statistical analysis to identify aberrant sample quality biomarkers in said sample, listing aberrant sample quality biomarkers, associating aberrant sample quality biomarkers with sample quality parameters, and providing a list of affected sample quality parameters.

In one embodiment, a method is provided for assessing a sample for sample quality by surveying the sample for the level(s) of sample quality biomarkers by statistical analysis to identify aberrant sample quality biomarkers in said sample, listing aberrant sample quality biomarkers, and identifying at least one intended use associated with one or more of the aberrant sample quality biomarkers.

In one embodiment, a method is provided for assessing a sample for sample quality by surveying the sample for the level(s) of sample quality biomarkers by statistical analysis to identify aberrant sample quality biomarkers in said sample, listing aberrant sample quality biomarkers, associating aberrant sample quality biomarkers with sample quality parameters, and identifying at least one intended use associated with one or more of the aberrant sample quality biomarkers.

In one embodiment, a method is provided for assessing a sample for sample quality by surveying the sample for the level(s) of sample quality biomarkers by statistical analysis to identify aberrant sample quality biomarkers in said sample, listing aberrant sample quality biomarkers, identifying at least one intended use associated with one or more of the aberrant sample quality biomarkers and providing a list of recommended approaches for evaluating the sample.

In one embodiment, a method is provided for assessing a sample for sample quality by surveying the sample for the level(s) of sample quality biomarkers by statistical analysis to identify aberrant sample quality biomarkers in said sample, listing aberrant sample quality biomarkers, associating aberrant sample quality biomarkers with sample quality parameters, and providing a list of recommended approaches for evaluating the sample.

In one embodiment a method is provided for assessing a sample for sample quality by surveying the sample for the level(s) of sample quality biomarkers by statistical analysis to identify aberrant sample quality biomarkers in said sample, listing aberrant sample quality biomarkers, associating aberrant sample quality biomarkers with sample quality parameters, providing a list of affected sample quality parameters, identifying at least one intended use associated with one or more of the aberrant sample quality biomarkers and, further, providing a list of recommended approaches for evaluating the sample.

DETAILED DESCRIPTION

Figure 1:
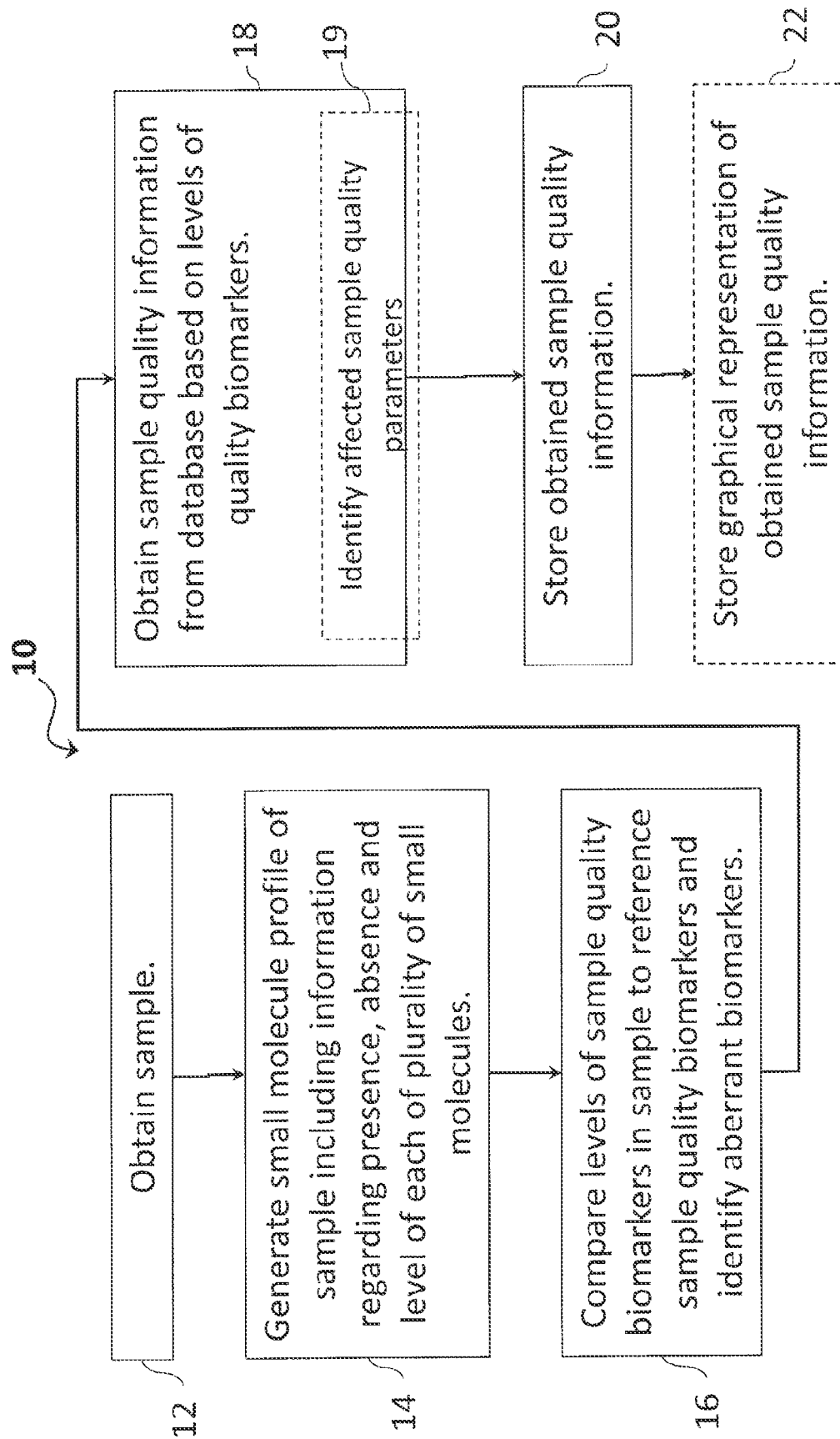
FIG. 1 is a block diagram of a method for assessing sample quality, in accordance with an embodiment.

A single test that can report on multiple sample quality parameters using the same sample and within the same dataset as the intended use analysis is described.

Prior to describing this invention in further detail, however, the following terms will be defined.

Definitions:

"Sample" can be any type of sample including a complex mixture or a biological sample such as a plant sample or an animal sample. The animal sample may be from a mammal such as, for example, a human, a mouse, a non-human primate, a rabbit or other mammal, or a non-mammal sample such as, for example, a drosophila or zebrafish sample. The biological sample of interest can include blood, plasma, serum, isolated lipoprotein fraction, saliva, urine, lymph fluid, and cerebrospinal fluid, a tissue sample, a cellular sample, or a skin sample. The biological sample may contain any biological material suitable for detecting the desired biomarkers, and may comprise cellular and/or non-cellular material from the subject. The sample can be isolated from any suitable biological tissue or fluid such as, for example, blood, blood plasma, serum, skin, epidermal tissue, adipose tissue, aortic tissue, liver tissue, urine, cerebral spinal fluid, crevicular fluid, amniotic fluid, or cell samples. The sample can be, for example, a dried blood spot where blood samples are blotted and dried on filter paper. In another the example, the sample can be isolated from a skin tape such as Sebutape®. In some embodiments, the sample may be an archival sample or a large collection of archival samples which have been collected and stored for long periods of time and for which handling protocols are uncertain or unavailable.

"Test sample" means the sample to be analyzed.

"Reference sample" means a sample used for determining a standard range for a level of small molecules. "Reference sample" may refer to an individual sample from an individual reference subject (e.g., a normal (healthy) reference subject or a disease reference subject), who may be selected to closely resemble the test subject by age and gender. "Reference sample" may also refer to a sample including pooled aliquots from reference samples. "Reference sample" may also refer to a sample (or a pool of samples) that has been processed according to a protocol specific for an intended use of the test sample.

"Subject" means any animal, but is preferably a mammal, such as, for example, a human, monkey, non-human primate, rat, mouse, dog or rabbit. In some aspects the subject is a patient. In some aspects the patient is a human.

The "level" of one or more biomarkers means the absolute or relative amount or concentration of the biomarker in the sample.

"Small molecule", "metabolite", "biochemical" means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates, which can be metabolized further or used to generate large molecules, called macromolecules. The term "small molecules" includes signaling molecules and intermediates in the chemical reactions that transform energy derived from food into usable forms. Non-limiting examples of small molecules include sugars, fatty acids, amino acids, nucleotides, intermediates formed during cellular processes, and other small molecules found within the cell.

"Biomarker" means a compound, preferably a metabolite, which is differentially present (i.e., increased or decreased) in a test sample as compared to one or more pre-determined reference ranges or to one or more reference samples, or in a sample treated according to one condition (e.g., fasted, stored at −80° C.) compared to a sample treated according to a second condition (e.g., fed, stored at −20° C.). A biomarker may be differentially present at any level, but is generally present at a level that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent). A biomarker may be differentially present at a level that is statistically significant (i.e., a p-value less than 0.05 and/or a q-value of less than 0.10 as determined using either Welch's T-test or Wilcoxon's rank-sum Test).

A "reference level" of a biomarker means a level of the biomarker that is indicative of sample quality or of one or more particular sample quality parameters. A "positive" reference level of a biomarker means a level that is indicative of an acceptable sample or sample quality parameter(s). A "negative" reference level of a biomarker means a level that is indicative of an unacceptable sample or sample quality parameter(s). A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for sample quality or for a particular sample quality parameter may be determined by measuring levels of desired biomarkers in one or more appropriate samples, referred to herein as a "reference sample", and such reference levels may be tailored to specific sample types or populations of subjects (e.g., a reference level may be age-matched so that comparisons may be made between biomarker levels in samples from subjects of a certain age and reference levels for a particular sample quality parameter in a certain age group). Such reference levels may also be tailored to specific techniques that are used to measure levels of biomarkers in samples (e.g., LC-MS, GC-MS, etc.).

"Aberrant" or "aberrant metabolite" or "aberrant level" refers to a metabolite or level of said metabolite that is either above or below a defined reference standard or range. In some embodiments the metabolite level is log-transformed prior to statistical analysis. In some embodiments the level is not log-transformed. Any statistical method may be used to determine aberrant metabolites. For example, a p-value, an IQR value or a Z-score. In one embodiment a p-value is determined and a metabolite that differs from the reference with, for example, a p-value less than 0.1 is considered aberrant. In another example embodiment a metabolite that differs from the reference with a p-value less than 0.05 is considered aberrant. In one embodiment the statistic is a Z-score. For example, for some metabolites, a metabolite having a log transformed level with a Z-score of >1 or <−1 is deemed aberrant. In some embodiments, for some metabolites, a metabolite having a log transformed level with a Z-score of >1.5 or <−1.5 is aberrant. In some embodiments, for some metabolites, a metabolite having a log transformed level with a Z-score of >2.0 or <−2.0 is aberrant. In some embodiments, different ranges of Z-scores are used for different metabolites. In some embodiments, the defined standard range may be based on an IQR of a level, instead of an IQR of a log transformed level. For example, for some metabolites, a log transformed level falling outside of at least 1.5*IQR (Inter Quartile Range) is aberrant. In another example, for some metabolites a log transformed level falling outside of at least 3.0*IQR is identified as aberrant.

"Non-biomarker compound" means a compound that is not differentially present in a biological sample from a subject or a group of subjects having a first phenotype (e.g., having a first disease) as compared to a biological sample from a subject or group of subjects having a second phenotype (e.g., not having the first disease). Such non-biomarker compounds may, however, be biomarkers in a biological sample from a subject or a group of subjects having a third phenotype (e.g., having a second disease) as compared to the first phenotype (e.g., having the first disease) or the second phenotype (e.g., not having the first disease).

"Metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques. A small molecule profile of the sample may include information regarding presence of, absence of, and a level of each of a plurality of small molecules in the sample. In some embodiments, the plurality of small molecules may include more than 25 small molecules, more than 50 small molecules, more than 100 small molecules, more than 200 small molecules, more than 300 small molecules, more than 400 small molecules, more than 500 small molecules, more than 600 small molecules, more than 700 small molecules, more than 800 molecules, more than 900 small molecules, more than 1000 small molecules, more than 1100 small molecules, more than 1200 small molecules more than 1300 small molecules, more than 1400 small molecules, more than 1500 small molecules, more than 2000 small molecules, more than 3000 small molecules, more than 4000 small molecules more than 5000 small molecules, more than 6000 small molecules, or more than 7000 small molecules. In other embodiments, the plurality of small molecules may include 25-25,000 small molecules, 50-25,000 small molecules, 100-25,000 small molecules, 200-25,000 small molecules, 300-25,000 small molecules, 400-25,000 small molecules, 500-25,000 small molecules, 600-25,000 small molecules, 700-25,000 small molecules, 800-25,000 small molecules, 900-25,000 small molecules, 1000-25,000 small molecules, 1100-25,000 small molecules, 1200-25,000 small molecules, or 1300-25,000 small molecules.

"Metabolome" means all of the small molecules present in a given organism.

"Sample quality" refers to one or more defined requirements for a sample based on an intended use of the sample. The requirements may be defined by a protocol such as a sample handling or a subject compliance protocol.

A "sample quality parameter" or "quality parameter" refers to one criterion that can be measured to determine if a sample is of suitable quality for an intended use. A sample quality parameter may be associated with protocol compliance and may indicate whether the sample has been handled according to a defined protocol (i.e., compliant with a sample handling protocol) or not and/or whether a subject from whom the sample was obtained was in compliance with a defined protocol (i.e., compliance with a protocol for the subject) or not. Example sample quality parameters related to sample handling include sample collection, collection tubes, collection tube additives, sample processing time, processing incubation temperature, time in storage, storage temperature, and freeze-thaw cycles. Example sample quality parameters related to subject protocol compliance include fasting status, medication and supplement status, smoking status, diet, and exercise compliance.

Sample "intended use" refers to the purpose for which the sample was obtained. The intended use of a sample may be experimental (e.g., global metabolomic discovery study, validation study (global or targeted), hypothesis testing, hypothesis generating, associating with a gene for determining significance of variants with unknown significance) or informational (e.g., diagnostic, health assessment, precision medicine). Informational use may refer to test panels that include one or more diagnostic tests or one or more health assessments. The intended use may refer to analysis of an individual sample or to analysis of each sample in studies of large cohorts. In some embodiments, the intended use may pertain to use of archival samples which have been collected and stored for long periods of time and for which handling protocols are uncertain or unavailable. In some embodiments the intended use may comprise performing metabolic profiling of the sample. In some embodiments the intended use may comprise performing biochemical analysis of the sample.

"Biochemical analysis" refers to the measurement of at least 1 and no more than 24 biochemicals in a sample.

"Acceptance criteria" refers to a standard used to determine if a sample is in sufficient compliance with a protocol to be suitable for its intended use. Acceptance criteria may be based on one or more sample quality biomarkers or one or more sample quality parameters. The biomarkers or parameters may be selected automatically (e.g., pre-selected default biomarkers, pre-selected default parameters) or may be modified manually by the analyst according to the intended use of the sample. The biomarkers or parameters selected may be based on the intended use of the sample. The biomarker or parameter may be associated with a threshold value that may be selected automatically (i.e., default threshold value) or may be set by the experimentalist or clinician. The acceptance criteria may use a composite score for one or more quality biomarkers or may use a composite score (e.g., a QPS) for one or more quality parameters to assess the sample quality or may use a composite score calculated from one or more selected QPS.

An "acceptable" sample or sample quality parameter refers to a sample or sample quality parameter that meets acceptance criteria for an intended use. An acceptable sample or sample parameter indicates compliance with a protocol for the sample or sample parameter.

An "unacceptable" sample or sample quality parameter refers to a sample or sample quality parameter that does not meet acceptance criteria for an intended use.

An unacceptable sample or sample parameter indicates non-compliance with a protocol for the sample or sample parameter.

A "marginal" quality sample refers to a sample that meets some, but not all of the acceptance criteria for the intended use; marginal samples may be subject to additional/corrective analysis or may be removed from the analysis.

A "sample quality composite score" or "composite score" refers to a value calculated using the levels of one or more sample quality biomarkers. The composite score may be calculated for the sample as a whole (e.g., overall composite score) or may be calculated for one or more sample quality parameters. When the score is calculated for a particular sample quality parameter, the term "quality parameter score" or "QPS" is used. One or more QPS may be combined to produce an overall quality score for the sample. When using QPS to calculate an overall composite score, the one or more QPS used for calculating the overall score may be selected by an analyst and the quality parameters selected may be based upon the intended use of the sample.

I. Biomarkers Indicative of Sample Quality

Novel biomarkers characteristic of particular sample quality parameters were identified using metabolomic profiling. Generally, metabolomic profiles were determined for biological samples obtained from samples handled according to (e.g., in compliance with) a sample collection protocol for a particular sample quality parameter, as well as from other samples not handled according to or in compliance with the sample collection protocol. Exemplary sampling considerations may include sample processing considerations such as sample storage, sample incubation, and freeze/thaw cycles, and subject non-compliance considerations such as fasting status, medication and supplement status, smoking status, and exercise compliance. The metabolomic profile for samples handled according to protocol was compared to the metabolomic profile for samples not handled according to protocol. Those molecules differentially present (e.g., those molecules differentially present at a level that is statistically significant) in the metabolomic profile of samples handled according to or in compliance with the protocol as compared to samples not handled according to or in compliance with the protocol were identified as biomarkers to distinguish those groups. Similarly, biomarkers of subject compliance were identified by comparing the metabolic profile of subjects in compliance with the protocol with the metabolic profile of non-compliant subjects. Detection of a level of one or more biomarkers identified in this manner can be used to assess the quality of a sample to determine if the sample is acceptable for its intended use. Said biomarkers can be detected in a sample individually, in subsets or in combinations thereof (e.g., as part of a profile).

The biomarkers are discussed in more detail herein. The biomarkers listed in Tables 1, 2, 3, 4, 5, 6, 7, 8, 9, 10, 11, 12, 13, 14, 15, 16, 17, 18, 19, 20, 21, 22, 23, 24, 25, and/or 26 and the biomarkers cysteinylglycine, sphingosine 1-phosphate, sphinganine-1-phosphate, ergothioneine and combinations thereof may be used to assess the quality of a sample. Although the markers are listed separately in Tables 1-26, one of ordinary skill in the art will understand that assessments of sample quality may be performed by combining markers found in different tables in many different combinations. It will be understood that the biochemical may be ordered in any way in the Tables, for example, by significance, alphabetically, by quality parameter, by biochemical superpathway and/or subpathway, etc.

A. Sample Processing Biomarkers

The level of a metabolite in a sample may be affected by the way the sample is processed after it has been collected from a subject. Biomarkers of sample processing were identified by comparing several sample processing conditions.

Sample Incubation and Sample Separation Biomarkers

One aspect of sample processing is related to how long the sample is held (incubated) at room temperature (RT) or at 4° C. (e.g., on ice or refrigerated) prior to freezing. Biomarkers of processing related to incubation time were discovered by comparing the levels of metabolites in samples that were immediately frozen after collection with samples that were held for various times before freezing. Another aspect of sample processing is the time interval between collection and serum or plasma separation from whole blood. Biomarkers of processing related to separation time of blood were discovered by comparing samples that were separated immediately after collection with samples incubated as whole blood prior to separation. Biomarkers for use in the methods disclosed herein for assessing the sample quality parameter related to sample processing include those listed in Tables 1, 2, 3, 4, 5, and/or 6. As seen in the tables, the biomarkers may include adenosine 5'-monophosphate (AMP), cys-gly oxidized, glucose, taurine, arginine, ornithine, spermine, spermidine, hypoxanthine, xanthine, oxidized glutathione, cysteine-glutathione disulfide, 5-oxoproline, thymine, 2'-deoxyuridine, 2'-deoxyinosine, 3-hydroxypropanoate, 4-phenylbutyrate, caproate (6:0), benzoate, stearoylcarnitine (C18), succinate, pyruvate, lactate, fumarate, malate, glutamate, α-ketoglutarate, linoleoylcarnitine, oleoylcarnitine, palmitoylcarnitine, myristoylcarnitine, adenosine, inosine, sphingosine, sphinganine, oleic ethanolamide (oleoyl ethanolamide), palmitoyl ethanolamide, and combinations and subsets thereof. In one embodiment, the one or more biomarkers may be selected from the group consisting of adenosine 5'-monophosphate (AMP), cys-gly oxidized, glucose, taurine, and combinations and subsets thereof.

Sample Storage Biomarkers

The level of a metabolite in a sample may be affected by sample storage conditions. Biomarkers of sample storage were identified by comparing several sample storage conditions. One aspect of sample quality related to sample storage is the storage temperature. Another aspect is the time in storage. Biomarkers for use in the methods disclosed herein for assessing sample storage include those listed in Tables 7, 8, 9, and/or 18. As seen in the tables, the biomarkers may include α-ketoglutarate, acetylcarnitine, propionylcarnitine, caproate (6:0), 4-methyl-2-oxopentanoate, 3-methyl-2-oxovalerate, 3-methyl-2-oxobutyrate, gamma-glutamyl-leucine, gamma-glutamyl-valine, glutamine, methionine and combinations and subsets thereof. In one embodiment, the one or more biomarkers may be selected from the group consisting of 4-methyl-2-oxopentanoate, acetylcarnitine, α-ketoglutarate, caproate (6:0), gamma-glutamyl-leucine, glutamine, methionine, and combinations and subsets thereof.

Freeze/Thaw Cycles Biomarkers

The metabolite levels in a sample may be affected by the number a freeze-thaw cycles that a sample undergoes. Biomarkers for use in the methods disclosed herein for assessing sample freeze-thaw cycles include those listed in Tables 10, 11, and/or 12. As seen in the tables, the biomarkers may include adenosine, succinate, 13-HODE+9-HODE, 3-hydroxy-2-ethylpropionate, caproate (6:0), docosahexaenoate (DHA; 22:6n3), eicosapentaenoate (EPA; 20:5n3), 2'-deoxyuridine, phenyllactate (PLA), alpha-hydroxyisovalerate, arachidonate (20:4n6), gamma-glutamylmethionine, inosine, isoleucine, myristoleate (14:1n5), phenylacetate, stearoylcarnitine (C18), 2-methylcitrate, decanoylcarnitine (C10), thymine, acetylcarnitine (C2), hexanoylcarnitine (C6), palmitoylcarnitine (C16), myristoylcarnitine, phenylpyruvate, argininosuccinate, and combinations and subsets thereof.

B. Subject Compliance Biomarkers

The metabolite levels in a sample may be affected by the compliance of a subject with a given protocol. Exemplary aspects of sample quality related to subject compliance include: fasting status, medication and supplement status, smoking status, diet, and exercise compliance.

Fasting Status Biomarkers

Biomarkers of sample quality related to fasting status were discovered by comparing the levels of metabolites in samples from subjects that were fasted with samples from subjects that were fed. Biomarkers for use in the methods disclosed herein for assessing the fasting status of an individual include those listed in Tables 13, 14, 15, 16, and/or 17. As seen in the tables, the biomarkers may include methionine sulfoxide, glycocholate, dopamine sulfate, azelate, uridine, xanthine, mannose, palmitoleate, and combinations and subsets thereof.

II. Methods of Assessing Sample Quality Using Biomarkers

General Description of the Method

An assessment of sample quality can be made or facilitated by analyzing a sample to determine the level of one or more biomarkers selected from Tables 1, 2, 3, 4, 5, 6, 7, 8, 9, 10, 11, 12, 13, 14, 15, 16, 17, 18, 19, 20, 21, 22, 23, 24, 25, and 26 (including combinations and subsets thereof) and comparing the level(s) of the biomarkers in the sample to sample quality-positive and/or sample quality-negative reference levels of biomarkers. As mentioned above, the biomarkers listed in different tables may be combined in any combination to perform an assessment of sample quality. As seen in the tables, the biomarkers may include 3-methyl-2-oxobutyrate, 3-methyl-2-oxovalerate, 4-methyl-2-oxopentanoate, 4-phenylbutyrate, acetylcarnitine, adenosine, adenosine 5'-monophosphate (AMP), alpha-hydroxyisocaproate, alpha-ketoglutarate, azelate (nonanedioate), caproate (6:0), cys-gly oxidized, dopamine sulfate, gamma-glutamylleucine, gamma-glutamylvaline, glucose, glutamine, glycocholate, hexanoylcarnitine (C6), mannose, methionine, methionine sulfoxide, palmitoleate (16:1n7), propionylcarnitine, taurine, uridine, xanthine. For example, the level of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in the group or any fraction thereof, may be determined and used in such methods. Determining the level(s) of combinations of the biomarkers may allow greater sensitivity and specificity in the assessment of sample quality, and may allow better differentiation of sample quality parameters. In one embodiment, the level(s) of one or more sample quality biomarkers may be assessed in combination with the level(s) of one or more currently used sample quality biomarkers or parameters. In an embodiment, ratios of the one or more biomarkers may be used to assess sample quality. Further, one or more ratios of biomarkers may be used in combination with one or more biomarkers to assess sample quality.

Any suitable method may be used to analyze the biological sample in order to determine the level(s) of the one or more biomarkers in the sample. Suitable methods include, but are not limited to, chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured. The level(s) of the one or more biomarkers may also be determined as part of a biomarker profile, e.g., a metabolomic profile, using, for example, the methods set forth herein.

Comparison to References

After the level(s) of the one or more sample quality biomarkers in a sample are determined, the measured level(s) are compared to reference levels characteristic of a sample in compliance with a protocol (i.e., "positive" or "acceptable" sample quality), and/or reference levels characteristic of a sample not in compliance with a protocol (i.e., "negative" or "not acceptable" sample quality). In some embodiments, the measured levels are compared to reference levels for one or more quality parameters. In some embodiments, the measured levels are compared to reference levels for all quality parameters. In some embodiments, a sample is of acceptable quality based on criteria set by the experimentalist or clinician. Levels of the one or more biomarkers matching the reference levels characteristic of a sample positive for sample quality or a sample quality parameter (e.g., levels that are the same as the reference levels, substantially the same as the reference levels, not statistically different from the reference levels, within an established range of the reference levels, etc.) are indicative of acceptable sample quality or quality parameter (in compliance with protocol). Levels of the one or more biomarkers matching the reference levels characteristic of unacceptable sample quality (out of compliance with protocol) (e.g., levels that are the same as the reference levels, substantially the same as the reference levels, not statistically different from the reference levels, within an established range of the reference levels, etc.) are indicative of unacceptable sample quality or quality parameter (out of compliance with one or more protocol parameters). In addition, levels of the one or more biomarkers that are differentially present (e.g., at a level that is statistically significant) in the sample, as compared to reference levels characteristic of a sample acceptable (positive) for sample quality are indicative of unacceptable sample quality or quality parameter. Levels of the one or more biomarkers that are differentially present (e.g., at a level that is statistically significant) in the sample, as compared to reference levels characteristic of a sample negative for sample quality, are indicative of acceptable sample quality or quality parameter. In some embodiments, determination of acceptable or unacceptable sample quality may be determined based on a particular sample quality parameter or a combination of sample quality parameters. In some embodiments, the levels of biomarkers in a test sample compared to reference levels identifies one or more affected sample quality parameters in the test sample.

The level(s) of the one or more biomarkers may be compared to sample acceptable and/or unacceptable (quality-positive and/or quality-negative) reference levels using various techniques, including a simple comparison of the level(s) of the one or more biomarkers in the biological sample to sample quality-positive and/or sample quality-negative reference levels. The level(s) of the one or more biomarkers in the sample may also be compared to sample quality-positive and/or sample quality-negative reference levels using one or more statistical analyses (e.g., t-test, Welch's T-test, Wilcoxon's rank sum test, Z-score, random forest). In various embodiments, such comparisons may be made manually, by an automated system, or by an automated system with manual verification.

Ratios of biomarkers may be used to assess sample quality. For example, ratios of glucose to pyruvate, glucose to lactate, glucose to succinate, glucose to fumarate, glucose to malate, arginine to ornithine, arginine to spermine, or arginine to spermidine may be used to assess sample quality. One or more ratios of biomarkers may be used in combination with one or more biomarkers to assess sample quality. In one aspect, two or more biomarkers or ratios of biomarkers may be used to assess sample quality.

In one embodiment, the biomarkers may be classified according to biochemical pathway, and assessment of sample quality can be made or facilitated by analyzing a sample to determine the level(s) of one or more biomarkers selected from one or more biochemical pathways and comparing the level(s) of the one or more biomarkers in the sample to sample quality reference levels of the one or more biomarkers in order to assess the quality of the sample. For example, the biochemical pathways and the one or more biomarkers associated with each pathway may be: (a) urea cycle metabolism (e.g., arginine, ornithine, spermine, spermidine); (b) purine degradation (e.g., hypoxanthine, xanthine, AMP, adenosine, inosine); (c) glutathione metabolism (e.g., oxidized glutathione, cys-gly oxidized, cysteine-glutathione disulfide, 5-oxoproline); (d) thymine metabolism (e.g., thymine, 2'-deoxyuridine); (e) energy metabolism (e.g., glucose, pyruvate, lactate, succinate, fumarate, malate, α-ketoglutarate, linoleoylcarnitine, oleoylcarnitine, palmitoylcarnitine, stearoylcarnitine, myristoylcarnitine); (f) sphingolipid metabolism (e.g., sphingosine, sphinganine, oleic ethanolamide (oleoyl ethanolamide), palmitoyl ethanolamide). In another aspect, two or more biomarkers or ratios of biomarkers are selected from the biomarkers listed in two or more of the biochemical pathways in groups a-f.

Composite Score

A sample quality composite score may be used to assess sample quality. The sample quality score may be an overall quality score (QS) generated for the sample based on one or more biomarkers. In another aspect, the sample quality score may be generated based on one or more biomarkers for one or more quality parameters to generate one or more quality parameter scores (QPS). The analyst may select an overall quality score (QS) or a quality score for one or more quality parameters (QPS). The selection may be based on the intended use of the sample. In this regard, for some uses a single overall quality score may be sufficient while other intended uses may require the sample quality assessment to be based on one or more selected quality parameters. Furthermore, the parameters used in the sample quality assessment may vary with the intended use of the sample. For example, for some intended uses, the composite score may be calculated using levels of biomarkers for sample handling without regard for subject compliance biomarkers. For other intended uses, the composite score may be calculated using levels of a subset of sample handling biomarkers (e.g., storage temperature and incubation temperature, or freeze-thaw cycles). In still other intended uses, subject compliance biomarkers may be used to generate a composite score. In yet other intended uses, the composite score may be based on combinations of one or more subject compliance and one or more sample handling biomarkers. In one example, the levels of the biomarkers adenosine 5'-monophosphate (AMP), cys-gly oxidized, glucose, and taurine are used to generate a composite score.

In some embodiments, the standard range for the reference small molecule profile may be based on a composite score. The method may include generating a sample quality composite score based on a combination of data from one or more of the biomarkers or ratios of biomarkers for sample quality. In some aspects, the biomarkers used to calculate the composite score may be weighted and the coefficients (weights) may be determined using, for example, regression analysis, PLS, LDA or other formal statistical methods.

Reporting

A report listing all sample quality biomarkers determined to be aberrant in the test sample may be generated. In some embodiments, the biomarkers are automatically sorted by sample quality parameter. In other embodiments, a visualization of results showing sample quality parameters and individual sample quality biomarkers is generated. In yet other embodiments, affected sample quality parameters are identified. Thus, in some embodiments, the method can comprise analyzing and reporting the information obtained from the entire metabolic profile and can identify aberrant sample quality biomarkers and associated sample quality parameters to determine affected sample quality parameters, without relying on specific sample quality tests comprised of a single internal standard for quality assurance or quality control for specific sample quality parameters.

Sample Quality Parameters

The biomarkers for sample quality may indicate that a particular sample quality parameter is affected. For example, the sample quality parameter may provide an indication that the sample is not in compliance with a protocol. Protocol non-compliance may include issues with sample handling. Exemplary sample quality parameters related to sample handling may include: processing time, time in storage, storage temperature, freeze-thaw cycles, and collection tube additives. Protocol non-compliance may also include subject non-compliance. Exemplary sample quality parameters related to subject compliance include: fasting status, medication and supplement status, smoking status, and exercise compliance.

Assessing Sample Processing

An exemplary sample quality parameter is sample processing. Thus, an assessment of sample quality can be performed by analyzing a sample to determine the level of one or more biomarkers selected from Tables 1, 2, 3, 4, 5, and/or 6. The one or more biomarkers may include adenosine 5'-monophosphate (AMP), cys-gly oxidized, glucose, taurine, arginine, ornithine, spermine, spermidine, hypoxanthine, xanthine, oxidized glutathione, cysteine-glutathione disulfide, 5-oxoproline, thymine, 2'-deoxyuridine, 2'-deoxyinosine, 3-hydroxypropanoate, 4-phenylbutyrate, caproate (6:0), benzoate, stearoylcarnitine (C18), succinate, pyruvate, lactate, fumarate, malate, glutamate, α-ketoglutarate, linoleoylcarnitine, oleoylcarnitine, palmitoylcarnitine, myristoylcarnitine, adenosine, inosine, sphingosine, sphinganine, oleic ethanolamide (oleoyl ethanolamide), palmitoyl ethanolamide, and combinations and subsets thereof. The level(s) of the one or more biomarkers in the sample can be compared to sample quality-positive and/or sample quality-negative reference levels of the one or more biomarkers. In one embodiment, the one or more biomarkers may be selected from the group consisting of adenosine 5'-monophosphate (AMP), cys-gly oxidized, glucose, taurine, and combinations and subsets thereof. In an exemplary embodiment, an increase in the levels of adenosine 5'-monophosphate (AMP), cys-gly oxidized, and taurine, and a decrease in the level of glucose indicate prolonged sample processing time. In one example, the levels of the biomarkers adenosine 5'-monophosphate (AMP), cys-gly oxidized, glucose, and taurine can be used to generate a composite score. In another example, the levels of the biomarkers adenosine 5'-monophosphate (AMP), glucose, and taurine can be used to generate a different composite score. The composite score may comprise biomarkers that are weighted.

One aspect of sample processing is the time the sample is held prior to freezing. Assessment of sample quality related to the time the sample was held prior to freezing can be made or facilitated by analyzing a sample to determine the level of one or more biomarkers selected from Tables 1, 2, 3, 4, and/or 5, and comparing the level(s) of the one or more biomarkers in the sample to sample quality-positive and/or sample quality-negative reference levels of the biomarkers. The biomarkers may include adenosine 5'-monophosphate (AMP), cys-gly oxidized, glucose, taurine, arginine, ornithine, spermine, spermidine, hypoxanthine, xanthine, oxidized glutathione, cysteine-glutathione disulfide, 5-oxoproline, thymine, 2'-deoxyuridine, 2'-deoxyinosine, 3-hydroxypropanoate, 4-phenylbutyrate, caproate (6:0), benzoate, stearoylcarnitine (C18), succinate, and combinations and subsets thereof.

Another aspect of sample processing is the time interval between sample collection and serum or plasma separation from whole blood. Assessment of sample quality related to this time interval can be made or facilitated by analyzing a sample to determine the level of one or more biomarkers selected from Tables 1 and/or 2 and comparing the level(s) of the one or more biomarkers in the sample to sample quality-positive and/or sample quality-negative reference levels of biomarkers. The biomarkers may include adenosine 5'-monophosphate (AMP), cys-gly oxidized, glucose, taurine, pyruvate, lactate, succinate, fumarate, malate, glutamate, α-ketoglutarate, linoleoylcarnitine, oleoylcarnitine, palmitoylcarnitine, stearoylcarnitine, myristoylcarnitine, arginine, ornithine, spermine, spermidine, adenosine, xanthine, inosine, sphingosine, sphinganine, oleic ethanolamide (oleoyl ethanolamide), palmitoyl ethanolamide, and combinations and subsets thereof.

Assessing Sample Storage

Another sample quality parameter is sample storage. Assessment of sample quality related to sample storage can be made or facilitated by analyzing a sample to determine the level of one or more biomarkers selected from Tables 7, 8, 9, and/or 18 and comparing the level(s) of the one or more biomarkers in the sample to sample quality-positive and/or sample quality-negative reference levels of the biomarkers. The biomarkers may include α-ketoglutarate, acetylcarnitine, propionylcarnitine, caproate (6:0), 4-methyl-2-oxopentanoate, 3-methyl-2-oxovalerate, 3-methyl-2-oxobutyrate, gamma-glutamyl-leucine, gamma-glutamyl-valine, glutamine, methionine and combinations and subsets thereof. In one embodiment, the one or more biomarkers may be selected from the group consisting of α-ketoglutarate, acetylcarnitine, propionylcarnitine, caproate (6:0), 4-methyl-2-oxopentanoate, 3-methyl-2-oxovalerate, 3-methyl-2-oxobutyrate, gamma-glutamyl-leucine, gamma-glutamyl-valine, glutamine, methionine, and combinations and subsets thereof. In another embodiment, an increase in the levels of caproate (6:0), gamma-glutamyl-leucine, gamma-glutamyl-valine, and a decrease in the levels of α-ketoglutarate, acetylcarnitine, propionylcarnitine, 4-methyl-2-oxopentanoate, 3-methyl-2-oxovalerate, 3-methyl-2-oxobutyrate, glutamine, methionine, indicate that the sample was stored at −20° C. instead of −80° C. The biomarkers may be used to generate a composite score. For example, the levels of the biomarkers 4-methyl-2-oxopentanoate, acetylcarnitine, α-ketoglutarate, caproate (6:0), gamma-glutamyl-leucine, glutamine, and methionine, may be used to generate a composite score. In another example, the levels of the biomarkers 4-methyl-2-oxopentanoate, α-ketoglutarate, caproate (6:0), gamma-glutamyl-leucine, glutamine, and methionine, may be used to generate a composite score. The composite score may comprise biomarkers that are weighted.

The sample quality related to sample storage may be affected by the storage temperature and the time in storage.

Assessing Effect of Freeze-Thaw Cycles

Another parameter that can affect the quality of a sample is the number of freeze-thaw cycles. In that regard, assessment of sample quality related to freeze-thaw cycles can be made or facilitated by analyzing a sample to determine the level of one or more biomarkers selected from Tables 10, 11, and/or 12 and comparing the level(s) of the biomarkers in the sample to sample quality-positive and/or sample quality-negative reference levels of the biomarkers. The biomarkers may include adenosine, succinate, 13-HODE+9-HODE, 3-hydroxy-2-ethylpropionate, caproate (6:0), docosahexaenoate (DHA; 22:6n3), eicosapentaenoate (EPA; 20:5n3), 2'-deoxyuridine, phenyllactate (PLA), alpha-hydroxyisovalerate, arachidonate (20:4n6), gamma-glutamylmethionine, inosine, isoleucine, myristoleate (14:1n5), phenylacetate, stearoylcarnitine (C18), 2-methylcitrate, decanoylcarnitine (C10), thymine, acetylcarnitine (C2), hexanoylcarnitine (C6), palmitoylcarnitine (C16), myristoylcarnitine, phenylpyruvate, argininosuccinate, and combinations and subsets thereof. In an exemplary embodiment, the sample is a blood or serum sample, and an increase in the levels of acetylcarnitine (C2), caproate (6:0), decanoylcarnitine (C10), succinate and a decrease in the levels of 13-HODE+9-HODE, 2'-deoxyuridine, 2-methylcitrate, 3-hydroxy-2-ethylpropionate, adenosine, alpha-hydroxyisovalerate, arachidonate (20:4n6), docosahexaenoate (DHA; 22:6n3), eicosapentaenoate (EPA; 20:5n3), gamma-glutamylmethionine, hexanoylcarnitine (C6), inosine, isoleucine, myristoleate (14:1n5), myristoylcarnitine, palmitoylcarnitine (C16), phenylacetate, phenyllactate (PLA), stearoylcarnitine (C18), thymine indicate that plasma or serum quality is unacceptable for the freeze-thaw quality parameter. In another exemplary embodiment, the sample is a urine sample, and an increase in the levels of 2-methylcitrate, argininosuccinate, inosine, and a decrease in the levels of laurylcarnitine (C12), phenylpyruvate indicate that the urine quality is unacceptable for the freeze-thaw quality parameter. The biomarkers may be used to generate a composite score. The composite score may comprise biomarkers that may be weighted.

Assessing Fasting Status

Sample quality can be assessed by analyzing the fasting status of the subject from whom a sample is obtained. In this regard, sample quality can be assessed by analyzing a sample to determine the level of one or more biomarkers selected from Tables 13, 14, 15, 16, and/or 17 and comparing the level(s) of the biomarkers in the sample to sample quality-positive and/or sample quality-negative reference levels of biomarkers. The biomarkers may include methionine sulfoxide, glycocholate, dopamine sulfate, azelate, uridine, xanthine, mannose, palmitoleate, and combinations and subsets thereof. In one embodiment, an increase in the levels of methionine sulfoxide, glycocholate, dopamine sulfate, azelate, and a decrease in the levels of uridine, xanthine, mannose, palmitoleate, indicate that the subject was not fasted (i.e., was fed). The biomarkers may be used to generate a composite score. For example, the levels of the biomarkers methionine sulfoxide, glycocholate, dopamine sulfate, azelate, uridine, xanthine, mannose, and palmitoleate can be used to generate a composite score. The composite score may comprise biomarkers that are weighted.

III. System, Method, Computer Program Product

Various systems and apparatuses are used in assessing sample quality according to the methods described herein. FIG. 1 provides a flow chart showing an example of how such systems and apparatuses may be used.

FIG. 1 is a block diagram of a method 10 for assessing sample quality. In some embodiments, the method 10 includes generating a sample quality composite score based on a weighted combination of data from one or more of the quality biomarkers, and obtaining sample quality information from the database based on the levels of the quality biomarkers and includes obtaining sample quality information from the database based on the generated sample quality composite score. The obtained sample quality information is stored (step 20). The stored sample quality information can include one or more of: i) an identification of at least one sample quality parameter associated with the quality biomarkers; ii) an identification of at least one aspect of the intended use associated with one or more of the quality biomarkers having an aberrant level; and iii) an identification of at least one recommended approach for evaluating the sample (e.g., accept sample, reject sample/remove from analysis, modify analysis to take affected parameter into account (e.g., apply a "correction factor" to adjust level of affected metabolites)). Thus, the stored sample quality information facilitates sample analysis. In some embodiments, the method may further include storing a graphical representation of the obtained sample quality information (step 22). The dashed lines around the boxes for steps 19 and 22 in FIG. 1 indicate that these steps need not be present in all embodiments. The method 10 may be applied to a single sample or to any number of samples simultaneously.

As shown in FIG. 1, a sample is obtained (step 12). The sample may be obtained from any source. A small molecule profile of the sample is generated including information regarding presence of, absence of, and, if appropriate, a level of each of a plurality of small molecules in the sample (step 14).

Generation of the small molecule profile of a sample requires analysis of its constituent biochemical small molecules. The analysis may include extracting at least some of the plurality of small molecules from the sample. Suitably, the analysis may be conducted using one or more different analytical techniques known in the art, for example, liquid chromatography (LC), high performance liquid chromatography (HPLC) (see Kristal, et al. *Anal. Biochem.* 263:18-25 (1998)), gas chromatography (GC), thin layer chromatography (TLC), electrochemical separation techniques (see, WO 99/27361, WO 92/13273, U.S. Pat. Nos. 5,290,420, 5,284, 567, 5,104,639, 4,863,873, and U.S. RE32,920), refractive index spectroscopy (RI), ultra-violet spectroscopy (UV), fluorescent analysis, radiochemical analysis, near-infrared spectroscopy (Near-IR), nuclear magnetic resonance spectroscopy (NMR), light scattering analysis (LS), mass spectrometry (MS), tandem mass spectrometry (MS/MS$^2$), and combined methods such as gas-chromatography/mass spectrometry (GC-MS), liquid chromatography/mass spectrometry (LC-MS), ultrahigh performance liquid chromatography/tandem mass spectrometry (UHLC/MS/MS$^2$) and gas-chromatography/tandem mass spectrometry (GC/MS/MS$^2$).

U.S. Pat. No. 7,884,318, discloses systems, methods and computer-readable media for determining a composition of chemical constituents in a complex mixture, which may be employed for generating the small molecule profile of the sample, in accordance with some embodiments. U.S. Pat. No. 7,884,318 is incorporated by reference herein in its entirety. As described in U.S. Pat. No. 7,884,318, separation data and mass spectroscopy data are generated for a sample, and the generated separation and mass spectroscopy data is compared with a library of chemical information (a "chemical library") to determine small molecule chemical constituents of the sample.

U.S. Pat. Nos. 7,561,975 and 7,949,475, each of which is incorporated by reference herein in its entirety, provide additional disclosure regarding analysis for identification of small molecule constituents of a biological sample for multiple biological samples.

In some embodiments, multiple aliquots (e.g., two, three, four, five, six, etc.) of a single test sample may be tested. In some embodiments, aliquots from test samples from multiple different individuals are analyzed in the same run. In one embodiment, the test samples may be run as individual samples, in duplicate, triplicate, quadruplicate, or etc.

In some embodiments, data analysis for generation of the small molecule profile is partially automated (e.g., with a person manually verifying the identifications of some or all small molecules based on the generated data). In some embodiments, data analysis for generation of the small molecule profile is fully automated.

The small molecule profile is compared to one or more reference small molecule profile(s) to identify sample quality biomarkers that are aberrant in the sample (step 16). The reference small molecule profile may include a standard range for each of a plurality of biomarkers. An aberrant biomarker is a biomarker with a level in the sample that is outside the standard range for the biomarker. In some embodiments, the reference small molecule profile is determined, at least in part, from statistical analysis of small molecules profiles generated for reference samples.

Sample quality information is obtained from a database based on the levels of the sample quality biomarkers (step 18). The database includes information associating an aberrant level of one or more biomarkers with information regarding sample quality or a sample quality parameter for each of the plurality of sample quality parameters. In methods in which a sample quality parameter-specific composite score is generated based on a weighted combination of data from one or more of the subset of quality biomarkers, the database further includes information associating a range of sample quality parameter-specific composite scores with information regarding the sample quality parameter for one or more of the sample quality parameters.

The obtained sample quality information is stored (step 20). The stored sample quality information can include one or more of: i) an identification of at least one sample quality parameter associated with the identified aberrant sample quality biomarkers; ii) an identification at least one intended use associated with the identified aberrant sample quality biomarkers; and iii) an identification of at least one approach for evaluating the sample based on the aberrant levels of the sample quality biomarkers. In some embodiments, the stored sample quality information includes an identification of at least one sample quality parameter associated with the identified aberrant sample quality biomarkers and one or more of an identification at least one intended use associated with the identified sample quality biomarkers, and an identification of at least one approach for evaluating the sample based on the levels of the aberrant sample quality biomarkers. In some embodiments, the sample quality information may be stored in multiple databases (e.g., the sample analysis information may be stored in one database and the information with an identification of a sample quality parameter and information regarding approaches for evaluating the sample may be stored in another database).

Some embodiments include storing a graphical representation of some or all of the obtained sample quality information (step 22). In some embodiments, a graphical representation of the one or more sample quality parameters associated with the identified sample quality biomarkers is stored. As used herein, generation, storage and/or display of a graphical representation of some or all of the obtained sample quality information is also referred to as visualization of the information or visualization of the results.

The graphical representation may be stored in any known format for electronic storage of images (e.g., JPEG/JFIF, JPEG 2000, Exif, TIFF, RAW, GIF, BMP, PNG, PPM, PGM, PNM, WEBP, CGM, SVG, etc.) In some embodiments, the graphical representation(s) may be incorporated into a document and stored in a document file format (e.g., PDF, .ps, .doc, .docx, .ppt, .odt, .htm, .html, etc.).

In some embodiments, multiple types of sample quality information for the sample(s) may be compiled into a single document, which is referred to as a report herein. The report may include information regarding any or all of: a total number of different small molecule biochemicals detected; a total number of different sample quality biomarkers detected; identification of sample quality parameters associated with small molecules biomarkers; a listing of sample quality biomarkers associated with one or more sample quality parameters; identification of which sample quality biomarkers in the identified sample quality parameters were present in aberrant levels; identification of sample quality biomarkers present in aberrant levels and an indication of the levels; an indication of whether each aberrant sample quality biomarker is present at a level higher or lower than the standard range; an indication of a sample quality composite score for one or more sample quality parameters; an indication of whether the value for each sample quality parameter composite score is within the range of the reference score; a list of affected sample quality parameters; a list of at least one recommended approach for evaluating the sample. The report may be stored in a suitable electronic file format. In some embodiments, the report of the results is provided to a researcher and/or health care provider in any suitable electronic or non-electronic (e.g., paper) form.

Figure 2:
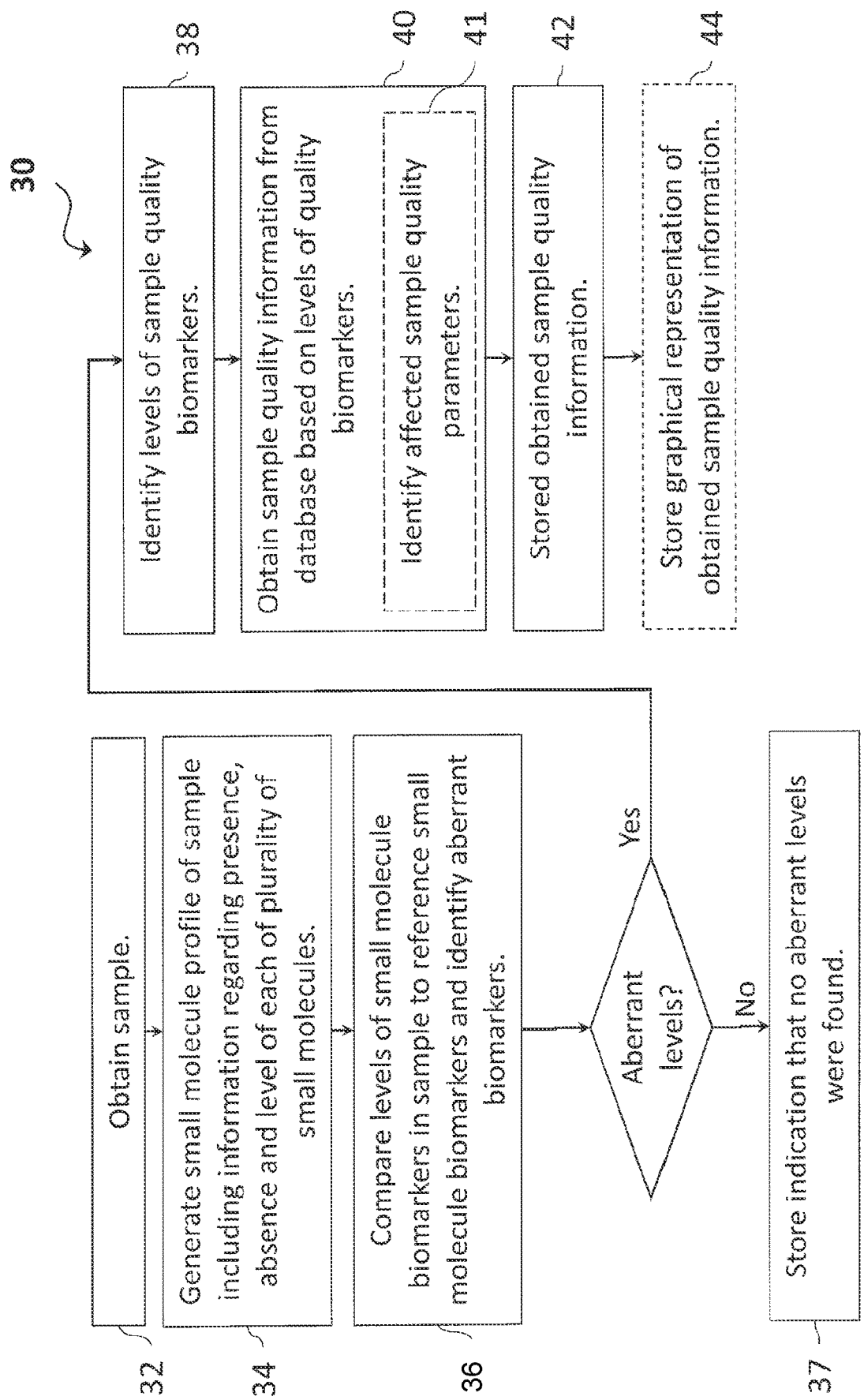
FIG. 2 is a block diagram of a method for screening a sample for a plurality of sample quality parameters, in accordance with an embodiment.

FIG. 2 is a block diagram of a method 20 for assessing a sample for a plurality of sample quality parameters, in accordance with an embodiment. A sample is obtained (step 32). A small molecule profile of the sample is generated including information regarding presence of, absence of, and a level of each of a plurality of small molecules in the sample (step 34). The small molecule profile includes information regarding the levels of sample quality biomarkers for assessing sample quality. The levels of the sample quality biomarkers in the sample are compared to a reference small molecule profile that includes a standard range for a level of each of the sample quality biomarkers, and the aberrant small molecule biomarkers are identified (step 36).

If none of the sample quality biomarkers in the small molecule profile of the sample have an aberrant level, information is stored indicating that no aberrant levels were detected (step 37).

If any aberrant biomarker levels are detected, sample quality analysis proceeds, and levels of sample quality biomarkers, including the sample quality biomarkers having aberrant levels, are identified (step 38). Sample quality information is obtained from a database based on the levels of sample quality biomarkers (step 40). In some embodiments, obtaining sample quality information based on the levels of the sample quality biomarkers includes identifying one or more affected sample quality parameters (step 41). In some embodiments, the method includes generating a sample quality parameter-specific composite score based on a weighted combination of data from one or more of the sample quality biomarkers, and obtaining sample quality information from the database based on the levels of the sample quality biomarkers including obtaining sample quality information from the database based on the generated sample quality parameter-specific composite score. The sample quality biomarkers used to generate the composite score may or may not have aberrant levels. The database includes information associating a level of one or more of the plurality of sample quality biomarkers with information regarding a sample quality parameter for each of a plurality of sample quality parameters. The obtained sample quality information is stored (step 42). The stored sample quality information includes one or more of: an identification of at least one sample quality parameter associated with the sample quality biomarkers, an identification at least one intended use associated with one or more of the sample quality biomarkers, and an identification of at least one recommended approach for evaluating the sample (e.g., analyze the sample with all measured small molecules, analyze the sample with selected measured small molecules, or remove the sample and all measured small molecules from analysis). In some embodiments, the method also includes storing a graphical representation of the obtained sample quality information (step 44). The dashed line around the boxes for steps 41 and 44 in FIG. 2 indicates that these steps need not be present in all embodiments.

The steps of generating the small molecule profile of the sample, comparing the profile of the sample quality biomarkers in the sample to a reference small molecule profile to determine if any sample quality biomarkers in the sample have aberrant levels, identifying sample quality biomarkers having aberrant levels, obtaining sample quality information from a database based on levels of the sample quality biomarkers, storing an indication that no aberrant levels were found, storing obtained sample quality information, storing a graphical representation of obtained sample quality information may be performed in part or in whole using instructions executing on one or processors of one or more computing systems.

Some embodiments include storing computer-executable code with instructions for performing various steps of methods described herein.

Figure 3:
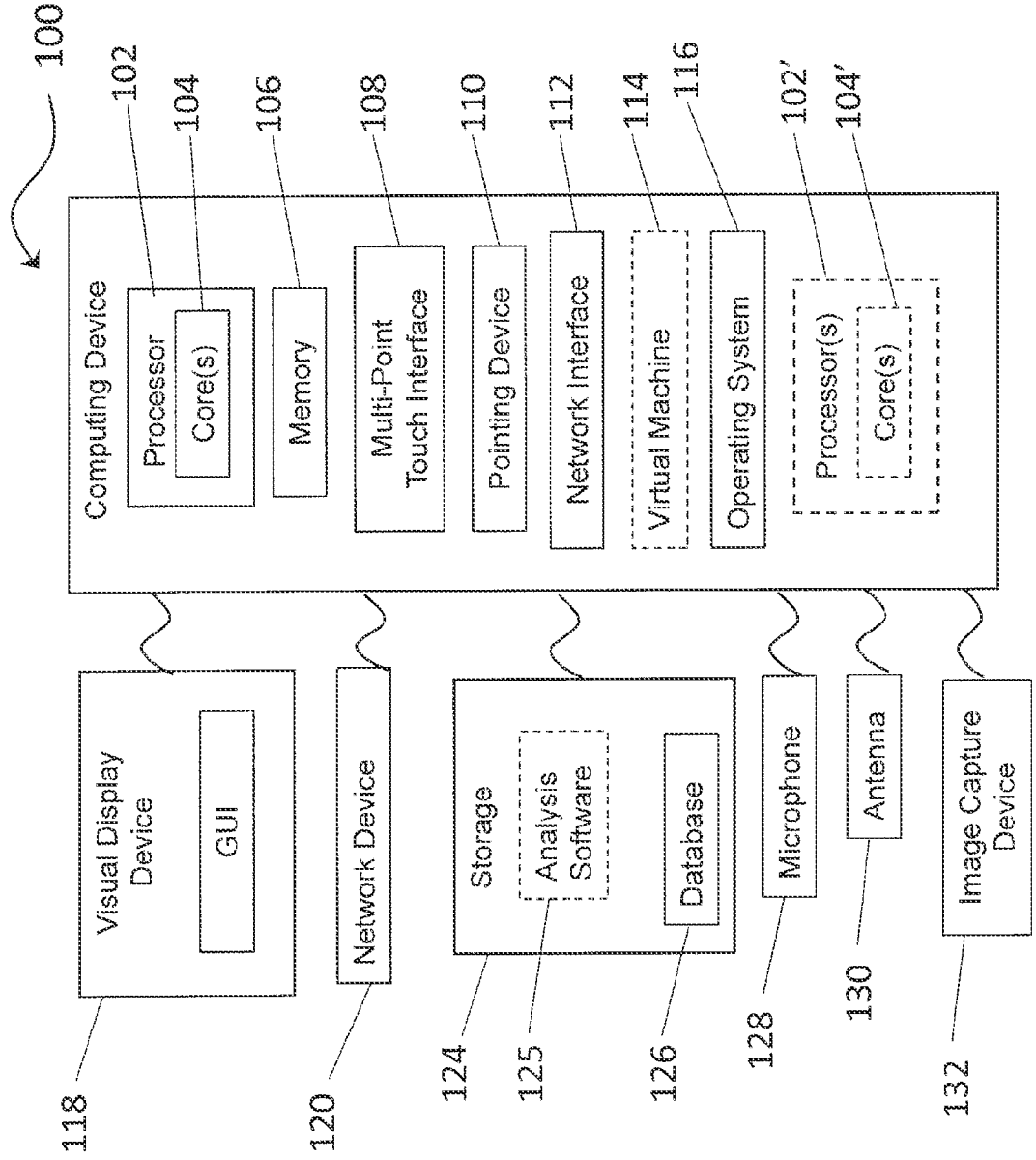
FIG. 3 is a block diagram of a computing device for use in implementing some steps of some exemplary methods, in accordance with some embodiments.

FIG. 3 is a block diagram of an exemplary computing device 100 that may be used to implement various steps of exemplary methods described herein. The computing device 100 includes one or more non-transitory computer-readable media for storing one or more computer-executable instructions or software for implementing exemplary embodiments. Suitably, the non-transitory computer-readable media may include, but are not limited to, one or more types of hardware memory, non-transitory tangible media (for example, one or more magnetic storage disks, one or more optical disks, one or more flash drives), and the like. For example, memory 106 included in the computing device 100 may store computer-readable and computer-executable instructions or software for implementing all or part of steps or methods described herein. The computing device 100 may also include a configurable and/or programmable processor 102 and associated core 104, and optionally, one or more additional configurable and/or programmable processor(s) 102' and associated core(s) 104' (for example, in the case of computer systems having multiple processors/cores), for executing computer-readable and computer-executable instructions or software stored in the memory 106 and other programs for controlling system hardware. Processor 102 and processor(s) 102' may each be a single core processor or multiple core (104 and 104') processor.

Virtualization may be employed in the computing device 100 so that infrastructure and resources in the computing device may be shared dynamically. A virtual machine 114 may be provided to handle a process running on multiple processors so that the process appears to be using only one computing resource rather than multiple computing resources. Multiple virtual machines may also be used with one processor.

Memory 106 may include a computer system memory or random access memory, such as DRAM, SRAM, EDO RAM, and the like. Memory 106 may include other types of memory as well, or combinations thereof.

A user may interact with the computing device 100 through a visual display device 118, such as a computer monitor, which may display one or more graphical user interfaces that may be provided in accordance with exemplary embodiments. The computing device 100 may include other I/O devices for receiving input from a user, for example, a keyboard or any suitable multi-point touch interface 108, a pointing device 110 (e.g., a mouse), a microphone 128, and/or an image capturing device 132 (e.g., a camera or scanner). The multi-point touch interface 108 and the pointing device 110 may be coupled to the visual display device 118. The computing device 100 may include other suitable conventional I/O peripherals.

The computing device 100 may also include one or more storage devices 124, such as a hard-drive, CD-ROM, or other computer readable media, for storing data and computer-readable instructions and/or software for implementing exemplary embodiments described herein. Exemplary storage device 124 may also store one or more databases for storing any suitable information required to implement exemplary embodiments. For example, exemplary storage device 124 can store one or more databases 126 that include any or all of a chemical library, a reference small molecule profile, small molecules profiles of one or more reference samples, small molecule profiles of one or more test samples, sample quality information associated with levels of one or more sample quality biomarkers for a plurality of sample quality parameters, information associating intended uses with one or more sample quality biomarkers, information associating a sample quality parameter with one or more sample quality biomarker levels for a plurality of sample quality parameters, and an identification of at least one recommended approach for evaluating the sample associated with one or more sample quality biomarker levels. In other embodiments, different databases for different steps may be associated with different computing devices. In some embodiments a database may be configured to automatically receive data corresponding to the level(s) of one or more sample quality biomarkers measured in a biological sample using an analytical device (e.g., a separation device coupled to a detection device, such as, for example, LC/MS, GC/MS) from the analytical device.

The one or more storage devices 124 may be used to store any or all of obtained sample quality information, graphical representations of obtained sample quality information, reports for a test sample, etc.

The one or more storage devices 124 and or the memory 106 may hold software 125 executable on the processor 102 for implementing an analysis facility that compares the small molecule biomarker profile of the sample to a reference small molecule biomarker profile that includes a standard range for a level of each of the plurality of sample quality biomarkers and identifies the sample quality biomarkers in the sample having aberrant levels.

The computing device 100 can include a network interface 112 configured to interface via one or more network devices 120 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing device 100 can include one or more antennas 130 to facilitate wireless communication (e.g., via the network interface) between the computing device 100 and a network. The network interface 112 may include a built-in network adapter, network interface card, PCMCIA network card, card bus network adapter, wireless network adapter, USB network adapter, modem or any other device suitable for interfacing the computing device 100 to any type of network capable of communication and performing the operations described herein. Moreover, the computing device 100 may be any computer system, such as a workstation, desktop computer, server, laptop, handheld computer, tablet computer (e.g., the iPad™ tablet computer), mobile computing or communication device (e.g., the iPhone™ communication device), or other form of computing or telecommunications device that is capable of communication and that has sufficient processor power and memory capacity to perform the operations described herein. In some embodiments, the computing device 100 may communicate via a network with one or more computing devices or analytical devices used to obtain experimental data (e.g., a computing device associated with an LC/MS system, a computing device associated with a GC/MS system, an LC/MS system, a GC/MS system).

The computing device 100 may run any operating system 116, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 116 may be run in native mode or emulated mode. In an exemplary embodiment, the operating system 116 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art shall understand that various substitutions and alterations in form and detail may be made therein without departing from the scope of the invention. Further still, other embodiments, functions and advantages are also within the scope of the invention.

Exemplary block diagrams/flowcharts are provided herein for illustrative purposes and are non-limiting examples of methods. One of ordinary skill in the art will recognize that exemplary methods may include more or fewer steps than those illustrated in the exemplary block diagrams/flowcharts, and that the steps in the exemplary block diagrams/flowcharts may be performed in a different order than the order shown in the illustrative block diagrams/flowcharts.

IV. Kit

Any of the described methods, alone or in combination, may be performed using tools provided in the form of a kit. Kits may further comprise appropriate controls, standards and/or detection reagents. In an embodiment, the kit may include tools and reagents for the analysis of a blood-based sample. The kit may comprise a sample collection element and a vessel for storing the sample. For example, the kit may comprise a sample collection element, a retrieved sample collection receptacle, sample labels, sample barcodes, and instruction protocol. The instruction protocol may be provided as a printed form or booklet or on an electronic medium, such as, for example, a computer disk or other computer readable medium.

The kit may be used in accordance with the following exemplary method. A blood sample may be collected from the subject using a needle and syringe. The blood can then be extruded into a collection receptacle (e.g., a vial, a conical tube, etc.). The sample in the collection receptacle may then be subjected to metabolic profiling and intended use analysis. Barcodes and labels enable the sample identity and the analyses results to be tracked through the analysis.

The kit may further comprise a volumetric container. The volumetric container may be any container (i.e., a cup, vial, microfuge tube, microtiter plate etc.) suitable for holding a liquid sample. The volumetric container may optionally contain volumetric measurements which may be useful in measuring out a desirable amount of the sample or other reagents. The volumetric container may be made of any material (e.g., plastics, aluminum, stainless steel). The internal volume of the volumetric container depends on the type of sample to be collected. The volumetric container can include a body and a cap. In some embodiments, the internal standard material may be attached to the cap. In some embodiments, the internal standard material may be coated on the internal volume of the body of the volumetric container.

In some embodiments, the volumetric container may additionally be configured for the type of sample collection contemplated and used for collection of the specimen. In other aspects, a specimen collection receptacle is separately provided in the kit, and may be in the form of a cup, vial, microfuge tube.

The kit may optionally comprise a transportation container. The transportation container may be any structure suitable for transportation of samples. The container is configured such that the sample material can be packed into the container and the container may be sealed.

The kit may optionally include an extraction solution.

EXAMPLES

The invention will be further explained by the following illustrative examples that are intended to be non-limiting.

I. General Methods

A. Sample Preparation.

Samples were prepared using the automated MicroLab STAR® system from Hamilton Company. Recovery standards were added prior to the first step in the extraction process for QC purposes. Sample preparation was conducted using a methanol extraction to remove the protein fraction while allowing maximum recovery of small molecules. The resulting extract was divided into five fractions: one for analysis by UPLC-MS/MS with positive ion mode electrospray ionization, one for analysis by UPLC-MS/MS with negative ion mode electrospray ionization, one for LC polar platform, one for analysis by GC-MS, and one sample was reserved for backup. Samples were placed briefly on a TurboVap® (Zymark) under nitrogen to remove the organic solvent. For LC, the samples were stored under nitrogen overnight. For GC, the samples were dried under vacuum overnight. Samples were then prepared for the appropriate instrument, either LC/MS or GC/MS.

B. Ultrahigh Performance Liquid Chromatography-Tandem Mass Spectroscopy (UPLC-MS/MS).

LC/MS analysis used a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in acidic or basic LC-compatible solvents, each of which contained 8 or more injection standards at fixed concentrations to ensure injection and chromatographic consistency. One aliquot was analyzed using acidic positive ion optimized conditions and the other using basic negative ion optimized conditions in two independent injections using separate dedicated columns (Waters UPLC BEH C18-2.1× 100 mm, 17 µm). Extracts reconstituted in acidic conditions were gradient eluted from a C18 column using water and methanol containing 0.1% formic acid. The basic extracts were similarly eluted from C18 using methanol and water containing with 6.5 mM Ammonium Bicarbonate. The third aliquot was analyzed via negative ionization following elution from a HILIC column (Waters UPLC BEH Amide 2.1×150 mm, 1.7 µm) using a gradient consisting of water and acetonitrile with 10 mM Ammonium Formate. The MS analysis alternated between MS and data-dependent MS2 scans using dynamic exclusion, and the scan range was from 80-1000 m/z.

C. Gas chromatography/Mass Spectrometry (GC/MS).

For GC/MS analysis, samples were re-dried under vacuum desiccation for a minimum of 24 hours prior to being derivatized under dried nitrogen using bistrimethyl-silyl-trifluoroacetamide (BSTFA). The GC column was a 20 m X 0.18 mm ID, with 5% phenyl; 95% dimethylsilicone phase. The temperature ramp was from 60° to 340° C. in an 18 minute period. Samples were analyzed on a Thermo-Finnigan Trace DSQ fast-scanning single-quadrupole mass spectrometer using electron impact ionization at unit mass resolution. The instrument was tuned and calibrated for mass resolution and mass accuracy on a daily basis.

D. Data Processing and Analysis.

For each biological matrix data set on each instrument, relative standard deviations (RSDs) of peak area were calculated for each internal standard to confirm extraction efficiency, instrument performance, column integrity, chromatography, and mass calibration. Several of these internal standards serve as retention index (RI) markers and were checked for retention time and alignment. Modified versions of the software accompanying the UPLC-MS and GC-MS systems were used for peak detection and integration. The output from this processing generated a list of m/z ratios, retention times and area under the curve values. Software specified criteria for peak detection including thresholds for signal to noise ratio, height and width. Missing values, if any, were imputed with the observed minimum for that particular compound.

The biological data sets, including QC samples, were chromatographically aligned based on a retention index that utilizes internal standards assigned a fixed RI value. The RI of the experimental peak is determined by assuming a linear fit between flanking RI markers whose values do not change. The benefit of the RI is that it corrects for retention time drifts that are caused by systematic errors such as sample pH and column age. Each compound's RI was designated based on the elution relationship with its two lateral retention markers. Using an in-house software package, integrated, aligned peaks were matched against an in-house library (a chemical library) of authentic standards and routinely detected unknown compounds, which is specific to the positive, negative or GC-MS data collection method employed. Matches were based on retention index values, and the range of RI units varied relative to the detection platform. The experimental spectra were compared to the library spectra for the authentic standard and assigned forward and reverse scores. A perfect forward score would indicate that all ions in the experimental spectra were found in the library for the authentic standard at the correct ratios and a perfect reverse score would indicate that all authentic standard library ions were present in the experimental spectra and at correct ratios. The forward and reverse scores were compared and a MS/MS fragmentation spectral score was given for the proposed match. All matches were then manually reviewed by an analyst that approved or rejected each call based on the mass, RI, and scores to assess the call and manually approves the peaks if the call is retained the criteria above. However, manual review by an analyst is not required. In some embodiments the matching process is completely automated.

Further details regarding a chemical library, a method for matching integrated aligned peaks for identification of named compounds and routinely detected unknown compounds, and computer-readable code for identifying small molecules in a sample may be found in U.S. Pat. No. 7,561,975, which is incorporated by reference herein in its entirety.

E. Quality Control.

Methods were put in place to control the quality of sample extraction and instrument run procedures. These methods occur after sample collection and processing. From the biological samples, aliquots of each of the individual samples were combined to make technical replicates, which were extracted as described above. Extracts of this pooled sample were injected six times for each data set on each instrument to assess process variability. As an additional quality control, five water aliquots were also extracted as part of the sample set on each instrument to serve as process blanks for artifact identification. All QC samples included the instrument internal standards to assess extraction efficiency, and instrument performance and to serve as retention index markers for ion identification. The standards were isotopically labeled or otherwise exogenous molecules chosen so as not to obstruct detection of intrinsic ions.

Example 1

Biomarkers for Assessing Sample Processing Conditions

Biomarkers for assessing the effects related to commonly encountered sample processing conditions were identified in several studies. In one study, whole blood samples were incubated at room temperature for various times prior to separating the plasma and freezing. In another study, whole blood samples were separated following collection and the resulting plasma samples were incubated at 4° C. for various times before freezing. In yet another study, whole blood samples were separated following collection and the resulting plasma samples were incubated at ambient temperature for various times before freezing. The results of each study are presented below.

In the first study, five whole blood samples were collected, divided into aliquots, and held at room temperature for 0 h (Control), 0.5 h, 1 h, 2 h, 4 h, and 24 h prior to plasma separation and freezing. The fold-change of each biomarker was calculated as the ratio of the mean level of the biomarker in the samples at each time point compared to the 0 h time point control samples, and the p-value was determined using matched pairs t-tests. The data is presented in Table 1. Table 1 includes, for each biomarker, the biochemical name of the biomarker, the fold change (FC) of the biomarkers in samples incubated at room temperature for 0.5 h, 1 h, 2 h, 4 h, and 24 hours prior to separation compared to control (0 h time point) samples and the p-value. Thus, the study provides biomarkers related to the time interval between collection time and plasma separation time.

TABLE 1

| Biomarkers of sample processing - Time incubated as whole blood prior to separation | | | | | | | | | | |
|---|---|---|---|---|---|---|---|---|---|---|
| | 0.5 h/0 h | | 1 h/0 h | | 2 h/0 h | | 4 h/0 h | | 24 h/0 h | |
| Biochemical Name | FC | p value | FC | p value | FC | p value | FC | p value | FC | p-value |
| adenosine monophosphate (AMP) | 1.68 | 6.55E−02 | 1.15 | 6.87E−01 | 1.55 | 7.34E−02 | 2.44 | 1.72E−03 | 11.96 | 2.79E−04 |
| 5-oxoproline | 1.09 | 4.55E−01 | 1.16 | 6.45E−02 | 1.42 | 5.22E−04 | 1.67 | 6.86E−04 | 3.49 | 1.04E−04 |
| spermine | 4.30 | 4.33E−01 | 1.08 | 9.38E−01 | 0.78 | 7.87E−01 | 0.80 | 7.95E−01 | 7.27 | 2.48E−03 |
| spermidine | 2.79 | 4.85E−01 | 1.04 | 9.73E−01 | 1.08 | 9.37E−01 | 0.90 | 9.07E−01 | 3.76 | 3.50E−02 |
| stearoylcarnitine | | | | | | | | | 1.76 | 1.17E−01 |
| inosine | 1.20 | 6.89E−01 | 1.21 | 6.19E−01 | 1.11 | 8.08E−01 | 1.56 | 3.91E−01 | 2.33 | 1.64E−02 |
| malate | 1.04 | 8.82E−01 | 1.04 | 8.96E−01 | 1.19 | 3.53E−01 | 1.29 | 1.73E−01 | 2.61 | 2.07E−02 |
| palmitoyl ethanolamide | 1.33 | 4.58E−01 | 1.68 | 1.17E−01 | 2.41 | 3.10E−03 | 3.09 | 8.08E−04 | 4.06 | 6.69E−03 |
| succinate | 0.96 | 7.61E−01 | 0.99 | 9.47E−01 | 1.01 | 9.12E−01 | 1.03 | 8.07E−01 | 1.49 | 7.54E−03 |
| oleic ethanolamide (oleoyl ethanolamide) | 1.88 | 1.10E−01 | 3.14 | 2.50E−02 | 6.22 | 1.90E−04 | 8.94 | 8.31E−05 | 10.24 | 1.06E−02 |
| adenosine | 1.05 | 7.32E−01 | 0.93 | 6.66E−01 | 0.94 | 7.80E−01 | 1.05 | 8.24E−01 | 2.00 | 1.45E−02 |
| S-adenosylhomocysteine (SAH) | 1.25 | 6.55E−01 | 1.64 | 2.69E−01 | 1.93 | 1.22E−01 | 1.84 | 2.16E−01 | 4.80 | 2.47E−04 |
| tartronate (hydroxymalonate) | 1.07 | 6.04E−01 | 0.94 | 6.84E−01 | 0.99 | 9.66E−01 | 0.85 | 2.38E−01 | 0.22 | 2.62E−04 |
| 1-arachidonoylglycerophosphate | 1.07 | 3.58E−01 | 1.00 | 7.89E−01 | 1.26 | 3.46E−01 | 4.86 | 8.32E−03 | 12.96 | 3.63E−04 |
| 1-methylguanosine | 0.87 | 4.22E−01 | 0.87 | 4.78E−01 | 0.86 | 4.45E−01 | 0.57 | 2.51E−02 | 0.19 | 4.86E−04 |
| oxalate (ethanedioate) | 1.00 | 9.88E−01 | 1.04 | 5.78E−01 | 1.04 | 6.05E−01 | 0.90 | 1.92E−01 | 0.65 | 7.00E−04 |
| adipate | 0.99 | 9.66E−01 | 1.14 | 2.86E−01 | 1.09 | 6.99E−01 | 1.51 | 2.32E−02 | 1.84 | 9.09E−04 |
| 1-stearoylglycerophosphoserine | 1.00 | 7.91E−01 | 1.00 | 5.18E−01 | 1.00 | 5.06E−01 | 1.00 | 7.28E−01 | 1.00 | 1.51E−03 |
| 1-palmitoylglycerophosphate | 1.00 | 1.50E−01 | 1.00 | 2.92E−01 | 1.00 | 2.39E−01 | 1.36 | 3.16E−02 | 4.46 | 1.75E−03 |
| leucylleucine | 1.99 | 1.65E−01 | 1.09 | 8.07E−01 | 1.25 | 5.18E−01 | 1.16 | 7.00E−01 | 2.48 | 2.89E−03 |
| 5,6-dihydrouracil | 1.00 | 9.16E−01 | 0.91 | 5.56E−01 | 1.08 | 6.97E−02 | 1.22 | 2.13E−03 | 1.47 | 3.79E−03 |
| glycerophosphorylcholine (GPC) | 1.23 | 5.55E−01 | 0.90 | 7.33E−01 | 1.37 | 4.64E−01 | 1.54 | 1.27E−01 | 2.39 | 5.49E−03 |
| 1-palmitoylglycerol (16:0) | 0.69 | 2.79E−02 | 0.82 | 2.19E−01 | 0.86 | 3.42E−01 | 0.72 | 5.70E−02 | 0.64 | 7.47E−03 |
| caproate (6:0) | 0.89 | 3.58E−01 | 0.99 | 9.33E−01 | 0.95 | 5.36E−01 | 1.01 | 9.50E−01 | 1.25 | 8.76E−03 |
| N-acetylaspartate (NAA) | 0.97 | 6.40E−01 | 1.03 | 7.57E−01 | 1.06 | 5.38E−01 | 1.09 | 3.88E−01 | 1.26 | 1.12E−02 |
| 1-pentadecanoylglycerophosphocholine (15:0) | 0.90 | 5.94E−01 | 1.06 | 6.05E−01 | 1.29 | 3.51E−02 | 1.16 | 2.73E−01 | 1.44 | 1.18E−02 |

TABLE 1-continued

Biomarkers of sample processing - Time incubated as whole blood prior to separation

| Biochemical Name | 0.5 h/0 h FC | p value | 1 h/0 h FC | p value | 2 h/0 h FC | p value | 4 h/0 h FC | p value | 24 h/0 h FC | p-value |
|---|---|---|---|---|---|---|---|---|---|---|
| isoleucylvaline | 0.96 | 9.01E−01 | 1.11 | 6.27E−01 | 0.66 | 2.00E−01 | 1.40 | 1.23E−01 | 1.91 | 1.56E−02 |
| 1-oleoylglycerol (18:1) | 0.66 | 1.24E−01 | 0.60 | 8.65E−02 | 0.63 | 5.66E−02 | 0.43 | 6.16E−03 | 0.41 | 1.63E−02 |
| HWESASLLR | 1.00 | 6.99E−01 | 1.00 | 2.23E−01 | 1.00 | 7.46E−01 | 1.00 | 9.96E−01 | 21.53 | 2.08E−02 |
| choline | 1.05 | 7.54E−01 | 1.10 | 5.00E−01 | 1.12 | 4.26E−01 | 1.28 | 1.02E−01 | 1.41 | 2.26E−02 |
| glycerophosphoethanolamine | 0.93 | 5.41E−01 | 0.93 | 4.89E−01 | 1.04 | 7.91E−01 | 1.05 | 7.32E−01 | 1.60 | 2.31E−02 |
| prolylglycine | 0.89 | 3.35E−01 | 0.88 | 3.46E−01 | 0.88 | 3.82E−01 | 1.00 | 9.89E−01 | 0.68 | 2.95E−02 |
| gamma-glutamylalanine | 0.95 | 6.71E−01 | 1.01 | 9.35E−01 | 1.05 | 7.32E−01 | 1.22 | 1.13E−01 | 1.54 | 3.02E−02 |
| 2-hydroxyglutarate | 0.85 | 2.78E−01 | 0.93 | 5.93E−01 | 1.13 | 4.58E−01 | 1.03 | 8.41E−01 | 1.79 | 3.25E−02 |
| uridine | 0.98 | 9.16E−01 | 1.06 | 7.67E−01 | 1.09 | 6.40E−01 | 1.15 | 4.39E−01 | 1.46 | 3.44E−02 |
| asparagylleucine | 1.68 | 1.61E−01 | 1.00 | 7.66E−01 | 1.00 | 9.54E−01 | 3.82 | 3.46E−01 | 8.21 | 3.67E−02 |
| 1-palmitoyl-GPC (16:0) | 0.93 | 6.66E−01 | 1.04 | 7.39E−01 | 1.24 | 5.34E−02 | 1.31 | 1.57E−02 | 1.43 | 3.74E−02 |
| phenylalanyltryptophan | 0.71 | 2.96E−01 | 0.95 | 8.08E−01 | 0.92 | 7.32E−01 | 0.87 | 5.15E−01 | 0.52 | 4.05E−02 |
| glycylproline | 0.48 | 3.05E−01 | 0.31 | 1.46E−01 | 0.12 | 6.09E−02 | 0.04 | 4.13E−02 | 0.04 | 4.13E−02 |
| 1-linoleoylglycerol (18:2) | 0.80 | 4.88E−01 | 0.64 | 2.56E−01 | 0.51 | 1.16E−01 | 0.48 | 9.85E−02 | 0.35 | 4.34E−02 |
| HWESASXX | 0.86 | 4.87E−01 | 1.14 | 7.23E−01 | 0.96 | 8.57E−01 | 1.02 | 9.50E−01 | 7.19 | 4.99E−02 |
| palmitoylcarnitine | | | | | | | | | 1.76 | 1.72E−01 |
| lactate | 1.11 | 5.83E−01 | 1.25 | 2.35E−01 | 1.53 | 2.37E−02 | 1.79 | 1.27E−03 | 3.54 | p < 0.0001 |
| alpha-ketoglutarate | | | | | | | | | 1.75 | 6.27E−02 |
| arginine | 0.86 | 4.34E−01 | 0.81 | 2.72E−01 | 0.71 | 1.07E−01 | 0.55 | 2.00E−02 | 0.26 | 8.38E−04 |
| fumarate | 1.06 | 7.74E−01 | 1.15 | 4.87E−01 | 1.31 | 2.01E−01 | 1.57 | 6.01E−02 | 3.09 | 2.09E−02 |
| glucose | | | | | | | | | 0.48 | 8.58E−02 |
| glutamate | 1.03 | 9.03E−01 | 1.06 | 8.33E−01 | 1.14 | 6.31E−01 | 1.51 | 1.94E−01 | 2.95 | 4.90E−03 |
| linoleoylcarnitine | 0.94 | 8.52E−01 | 1.30 | 5.14E−01 | 1.78 | 9.01E−02 | 2.27 | 3.42E−02 | 4.39 | 2.12E−02 |
| myristoylcarnitine | | | | | | | | | 1.64 | 1.98E−01 |
| oleoylcarnitine (C18) | 0.97 | 9.26E−01 | 1.24 | 4.86E−01 | 1.65 | 7.36E−02 | 2.05 | 6.67E−03 | 3.40 | 6.89E−03 |
| ornithine | 1.20 | 1.38E−01 | 1.38 | 1.61E−02 | 1.67 | 3.63E−03 | 2.02 | 2.44E−04 | 2.96 | 7.22E−05 |
| pyruvate | 1.20 | 5.36E−01 | 1.19 | 6.28E−01 | 1.43 | 4.32E−01 | 1.57 | 2.80E−01 | 7.83 | 2.59E−02 |
| sphingosine | 1.80 | 3.15E−02 | 1.85 | 2.67E−03 | 2.23 | 1.65E−02 | 2.76 | 3.45E−05 | 3.13 | 3.87E−03 |
| sphingosine 1-phosphate | 1.31 | 2.79E−01 | 1.42 | 8.67E−02 | 2.05 | 5.66E−03 | 2.55 | 2.41E−03 | 2.59 | 3.22E−02 |
| maltose | 0.68 | 5.62E−01 | 0.73 | 6.38E−01 | 0.77 | 6.90E−01 | 0.79 | 7.41E−01 | 3.21 | 2.51E−02 |
| mannose | 0.96 | 8.82E−01 | 1.03 | 8.88E−01 | 0.98 | 9.46E−01 | 0.76 | 3.04E−01 | 0.30 | 1.39E−02 |
| taurine | 1.08 | 4.28E−01 | 1.10 | 4.03E−01 | 1.08 | 5.19E−01 | 1.05 | 6.91E−01 | 1.93 | 8.73E−04 |

In a second study, sample quality biomarkers for assessing the effects of the time interval that plasma is stored at 4° C. prior to freezing at −80° C. were identified. Whole blood was collected and plasma was separated. Triplicate plasma samples were processed immediately by freezing at −80° C. within one hour of collection (control, timepoint 0 h) or processing was delayed by storing the plasma samples at 4° C. for 2, 4, and 20 hours prior to freezing at −80° C. After the levels of the metabolites were determined, the % difference between the delayed processing samples and the control samples was calculated to identify biomarkers for sample processing. Thus, the study provides biomarkers related to the time interval a plasma sample is held at 4° C. prior to freezing.

TABLE 2

Biomarkers for assessing sample processing - cold incubation prior to freezing

| Red Biochemical Name | Percent Change vs. Control | | |
|---|---|---|---|
| | 2 hour | 4 hour | 20 hour |
| 2'-deoxyinosine | 32.34 | 119.73 | 839.44 |
| 3-hydroxypropanoate | 44.05 | 34.39 | 36.39 |
| 4-phenylbutyrate | 39.31 | 51.82 | 114.47 |
| caproate (6:0) | 20.60 | 22.24 | 56.44 |
| 12-HETE | −32.85 | −20.98 | −45.80 |
| 13-HODE + 9-HODE | −8.02 | −23.39 | −38.30 |
| 2'-deoxyguanosine | −9.05 | −14.08 | −18.25 |
| adenosine | −9.00 | −39.15 | −29.82 |
| eicosapentaenoate (EPA; 20:5n3) | −10.91 | −20.72 | −21.07 |
| 2-hydroxy-3-methylvalerate | 8.29 | 8.80 | 62.50 |
| argininosuccinate | −7.63 | −3.51 | −16.02 |

TABLE 2-continued

Biomarkers for assessing sample processing - cold incubation prior to freezing

| Red Biochemical Name | Percent Change vs. Control | | |
|---|---|---|---|
| | 2 hour | 4 hour | 20 hour |
| decanoylcarnitine (C10) | 8.45 | 13.21 | 16.86 |
| docosahexaenoate (DHA; 22:6n3) | −3.86 | −14.67 | −17.55 |
| gamma-glutamylmethionine | −12.71 | −11.48 | −48.84 |
| hexanoylcarnitine (C6) | −14.69 | −14.67 | −36.58 |
| methionine | −2.04 | 4.28 | 32.03 |
| myristoleate (14:1n5) | −8.44 | −13.65 | −19.84 |
| uracil | 11.06 | 11.63 | 56.58 |
| sebacate (decanedioate) | −12.91 | −8.53 | −13.68 |

In a third study, four whole blood samples were separated immediately after collection and the resulting plasma samples were frozen at −80° C. within one hour of collection (control, 0 h time point), or after incubation at room temperature (about 23° C.) for 24, 48, 72, or 96 hours prior to being frozen at −80° C. The percent change was calculated by comparing the level of the biomarker in the sample at 24 h, 48 h, 72 h and 96 h to the 0 h control. The data is presented in Table 2. Table 2 includes, for each biomarker, the biochemical name of the biomarker, and the percent difference or percent change in the level of the biomarker at each time point compared to the control (0 h time point). Thus, the study provides biomarkers related to the time interval a plasma sample is held at room temperature prior to freezing.

TABLE 3

Biomarkers of sample processing - RT incubation prior to freezing

| | Percent Change vs. Control (0 time point) | | | |
|---|---|---|---|---|
| Biochemical Name | 1 day | 2 day | 3 day | 4 day |
| adenosine monophosphate (AMP) | 416.79 | 2124.06 | 3038.37 | 3941.25 |
| glutathione, oxidized (GSSG) | 361.91 | 3359.19 | 3657.22 | 2840.58 |
| cys-gly, oxidized | 143.20 | 495.89 | 781.35 | 1573.71 |
| spermine | 2897.39 | 21528.49 | 25072.27 | 87348.47 |
| spermidine | 874.25 | 10471.89 | 13300.03 | 19413.41 |
| inosine | 139.22 | 1998.44 | 4453.55 | 12151.70 |
| cysteine-glutathione disulfide | 306.07 | 1504.05 | 1711.69 | 1515.70 |
| 5-oxoproline | 50.50 | 243.52 | 422.86 | 761.74 |
| xanthine | −46.18 | −14.33 | 165.70 | 699.72 |
| thymine | −100.00 | 513.92 | 477.89 | 697.63 |
| succinate | 41.23 | 152.04 | 222.82 | 302.26 |
| stearoylcarnitine (C18) | −9.04 | 56.75 | 55.79 | 287.17 |
| malate | 104.61 | 202.41 | 217.00 | 219.93 |
| oleic ethanolamide (oleoyl ethanolamide) | 24.20 | 63.43 | 51.13 | 136.16 |
| adenosine | 45.00 | 94.88 | 204.84 | 108.01 |
| palmitoyl ethanolamide | 44.63 | 69.67 | 21.10 | 63.99 |
| 2'-deoxyuridine | −50.97 | −83.24 | −100.00 | −43.73 |
| taurine | 21.12 | 129.53 | 199.79 | 204.86 |
| sphinganine | 19.97 | 68.19 | 117.20 | 328.00 |
| ornithine | 17.38 | 14.51 | 9.39 | 7.69 |
| glutamate | 83.20 | 175.72 | 267.38 | 315.19 |
| arginine | −65.57 | −79.46 | −80.59 | −83.11 |
| glucose | −50.31 | −85.50 | −96.30 | −98.78 |
| pyruvate | 75.39 | 307.40 | 296.01 | 544.39 |
| lactate | 86.77 | 122.79 | 144.25 | 106.48 |
| fumarate | 28.44 | 21.94 | 15.31 | 14.65 |
| alpha-ketoglutarate | 56.48 | 100.77 | 159.29 | 119.94 |
| oleoylcarnitine (C18) | 42.01 | 163.77 | 96.76 | 275.06 |
| palmitoylcarnitine (C16) | 19.67 | 146.26 | 107.77 | 356.00 |
| linoleoylcarnitine | 42.59 | 158.11 | 111.65 | 288.18 |
| myristoylcarnitine | 17.73 | 134.39 | 75.70 | 185.46 |
| sphingosine | −1.22 | 122.04 | 133.48 | 257.61 |
| hypoxanthine | −100.00 | 6392.42 | 25003.89 | 75436.45 |

Figure 4:
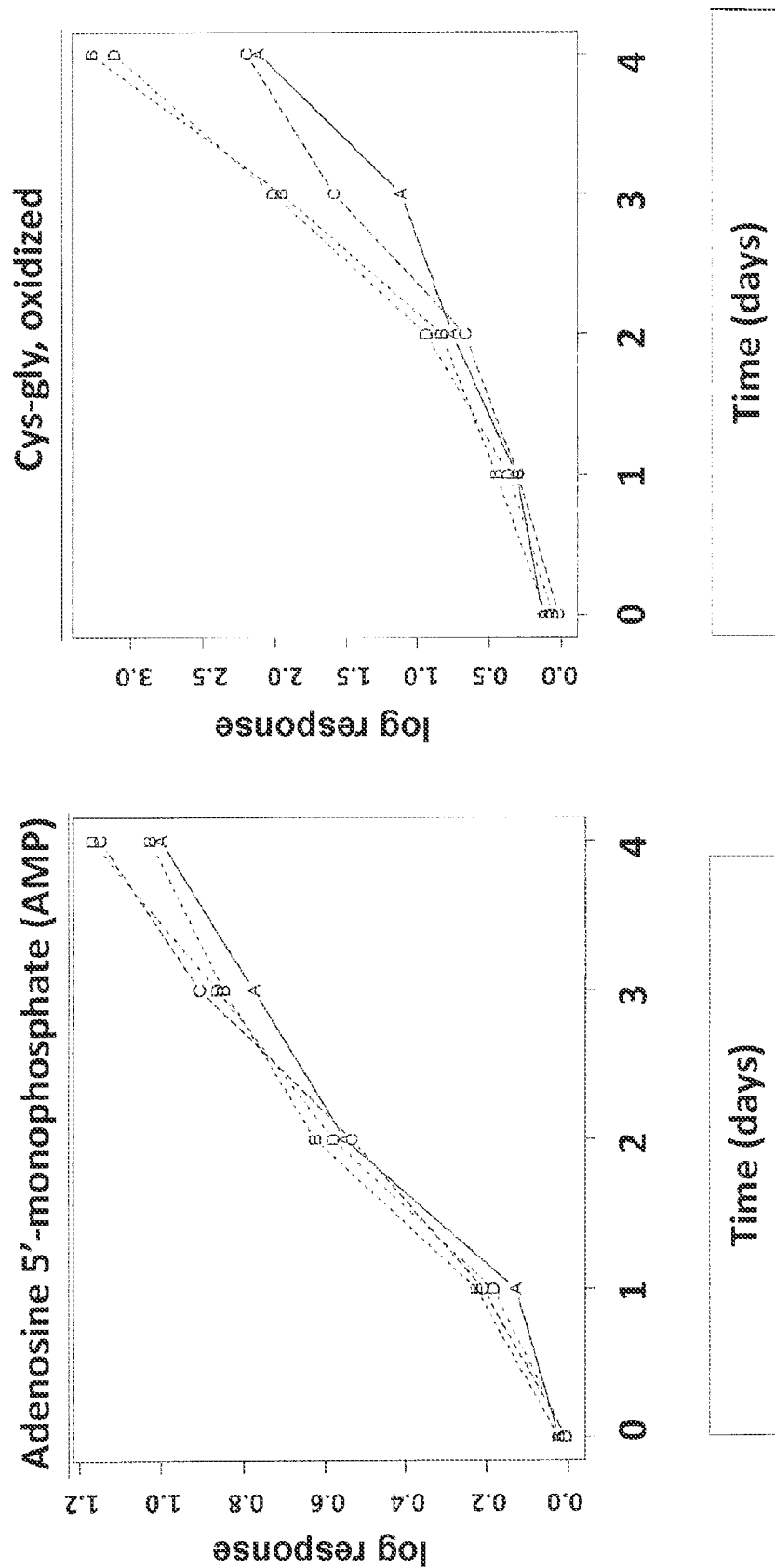
FIG. 4 is a graphical representation of levels of four exemplary biomarkers (adenosine 5'-monophosphate (AMP), cys-gly oxidized, glucose, taurine) for assessing the sample quality parameter of sample processing time. Sample processing time is indicated on the x-axis, and metabolite level is indicated on the y-axis. Results are shown for four samples, A-D.

In one example, four exemplary biomarkers were selected based on significance and consistency (i.e., that the level of the small molecule biomarker either consistently increased or consistently decreased for all subsequent times). The four candidate biomarkers are shown in Table 4 below, and the levels of the biomarkers over time are shown in the graphs in FIG. 4. For this example, the biomarkers were equally weighted; biomarkers that increase with longer sample processing time were assigned a positive weight, and biomarkers that decrease with longer sample processing time were assigned a negative weight. The weight for each biomarker is shown in column 2 of Table 3. It should be appreciated that the coefficients (weights) are exemplary and may be refined as additional data becomes available using formal statistical analysis methods as described herein.

TABLE 4

Exemplary biomarkers used to assess sample processing

| Candidate Biomarker | Weight |
|---|---|
| Adenosine 5'-monophpsphate (AMP) | +0.25 |
| cys-gly, oxidized | +0.25 |
| glucose | −0.25 |
| taurine | +0.25 |

The exemplary biomarkers were then evaluated using 30 plasma samples that were separated from whole blood immediately and frozen at −80° C. (0 time point) or incubated at room temperature for 0.5, 1, 2, 4, or 24 hours prior to separation from whole blood and freezing at −80° C. Five samples were analyzed for each time point. For each sample, each exemplary biomarker was evaluated individually, and the metabolite level at each time point was assessed. The biomarkers were also used to generate a composite score to assess sample quality and the sample processing time parameter for the samples. The composite score for sample processing time for each of the five samples at each time point was calculated as follows: Sample Processing Composite Score=0.25*(level AMP+level cys-gly oxidized−level glucose+level taurine).

Figure 5:
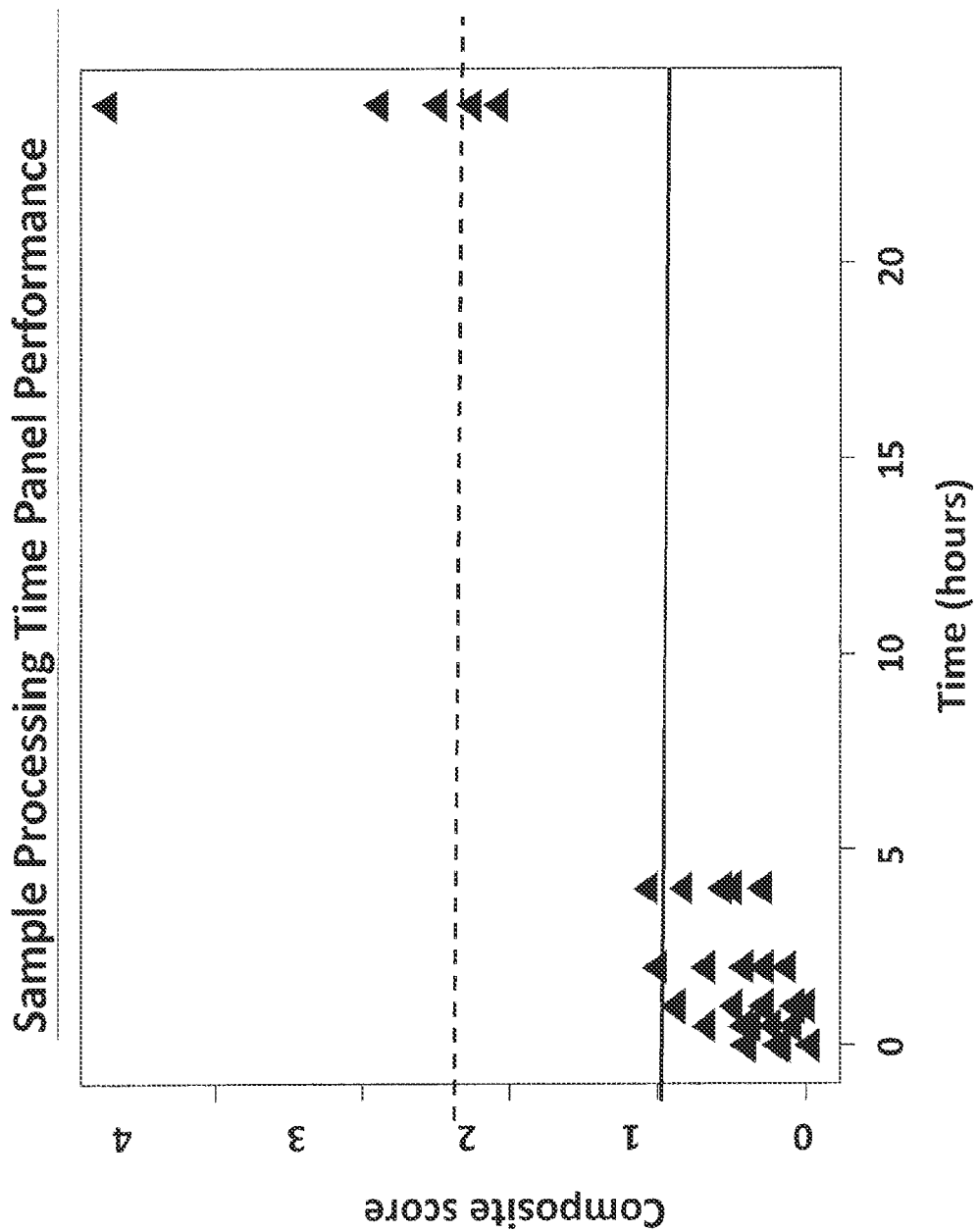
FIG. 5 is a graphical representation of sample processing time composite scores calculated using four exemplary biomarkers. Sample processing time is shown on the x-axis and sample composite score is indicated on the y-axis.

In this example, the composite scores were as follows: less than one for all ten samples incubated for 1 h or less; less than one for 8 of the 10 samples held for 2 h and 4 h; greater than one but less than two for 2 of 10 samples held for 2 h and 4 h; and greater than two for all 5 samples held for 24 h. A graph of the data is shown in FIG. 5.

When evaluating biomarkers, a rule can be established to flag potential protocol violations in the samples and/or to fail samples as violating protocol by setting a cut-off value for the composite score. In this example, the analyst set the composite score value for accepting sample at 1.0 and the composite score value for rejecting samples at 2.0. Thus, a composite score of less than 1.0 indicates that the sample meets acceptance criteria, while a composite score greater than 1.0 but less than 2.0 indicates that the sample should be flagged for additional evaluation; and a sample with a composite score greater than 2.0 is rejected. Using the selected cut-off values in this example, two samples were flagged, five samples were rejected, and the remaining samples were accepted. It should be appreciated that the cut-off value may change with the intended use of the sample. Additionally, the cut-off values may be selected automatically by the computing system or may be selected by the analyst.

Sample quality biomarkers for assessing sample processing time (storage at 4° C. prior to freezing at −80° C.) were also identified in serum, and urine samples. Triplicate samples of serum, and urine were frozen at −80° C. within one hour of collection (control, timepoint 0 h) or were stored at 4° C. for 2, 4, or 20 hours prior to freezing at −80° C. After the levels of metabolites were determined, the data were analyzed by calculating the % difference between the delayed processing samples and the control samples to identify biomarkers for sample processing time. The results are shown in Tables 5 (serum) and 6 (urine).

TABLE 5

Biomarkers for assessing sample processing time (serum)

| | Percent Change vs. Control | | |
|---|---|---|---|
| Biochemical Name | 2 hour Serum | 4 hour Serum | 20 hour Serum |
| benzoate | −22.75 | −18.49 | −16.56 |
| caproate (6:0) | 58.20 | 52.30 | 117.71 |
| N-acetylleucine | 74.39 | 85.73 | 101.90 |
| methylsuccinate | 22.14 | 19.26 | 16.49 |
| hypoxanthine | 4.30 | 19.81 | 20.75 |
| phenylpyruvate | −11.49 | −11.01 | −29.50 |
| 13-HODE + 9-HODE | 14.00 | 4.58 | 25.84 |
| alpha-hydroxyisocaproate | −19.55 | −11.47 | −29.27 |
| hexanoylcarnitine (C6) | −12.96 | −11.66 | −33.36 |

TABLE 6

Biomarkers for assessing sample processing time (urine)

| Biochemical Name | Percent Change vs. Control | | |
|---|---|---|---|
| | 2 hour Urine | 4 hour Urine | 20 hour Urine |
| 3-methyladipate | 28.10 | 24.45 | 24.16 |
| succinate | 34.34 | 36.48 | 19.08 |
| adenosine | 8.95 | 15.36 | 20.47 |
| inosine | 4.96 | 16.41 | 33.43 |
| laurylcarnitine (C12) | −8.02 | −17.04 | −16.90 |
| methionine | −4.52 | −20.58 | −29.25 |
| uridine | 8.67 | 17.79 | 77.30 |
| myristoylcarnitine | −8.61 | −12.00 | −24.62 |
| stearoylcarnitine (C18) | −56.04 | 19.40 | 166.25 |
| 3-hydroxypropanoate | 10.85 | 65.73 | 14.85 |
| 4-guanidinobutanoate | 11.08 | 15.82 | 11.12 |

Example 2

Biomarkers of Sample Storage Temperature

Sample quality biomarkers for assessing sample storage temperature were identified using two sample sets. Sample set 1 consisted of 543 plasma samples that had been stored at −20° C. Sample set 2 consisted of 401 plasma samples that had been stored at −80° C. As a control for both sample sets, a pooled reference sample made up of aliquots taken from an independent set of plasma samples that had been stored at −80° C. was used. After the levels of metabolites were determined, the data were analyzed to identify biomarkers for assessing sample storage temperature. Metabolites that differentiated samples stored at −20° C. from those stored at −80° C. are displayed in Table 7. Table 7 includes, for each biomarker, the biochemical name of the biomarker and the average level of the biomarker (in ion counts) in the samples stored at −20° C. and in the samples stored at −80° C. The average metabolite levels are shown in columns 2 & 3 of Table 7 for sample set 1 and in columns 4 & 5 for sample set 2. For set 1, the levels of alpha-ketoglutarate were so low in the samples stored at −20° C., that the metabolite was detected in only 1 of the 543 samples. In contrast, in set 2 where all samples were stored at −80° C., alpha-ketoglutarate was detected in about 75% of the 401 plasma samples.

TABLE 7

Biomarker metabolites that differentiate sample storage at −20° C. vs. −80° C.

| Biochemical name | Sample Set 1 | | Sample Set 2 | |
|---|---|---|---|---|
| | Metabolite Level −20° C. Storage | Metabolite Level −80° C. Storage (pooled reference) | Metabolite Level −80° C. Storage | Metabolite Level −80° C. Storage (pooled reference) |
| alpha-ketoglutarate | Not Detected | 100,917 | 31,426 | 108,146 |
| acetylcarnitine | 84,822 | 2,494,315 | 2,319,314 | 2,237,562 |
| propionylcarnitine | 76,039 | 332,821 | 362,872 | 320,365 |
| caproate (6:0) | 1,072,216. | 197,267 | 117,546 | 183,523 |
| 4-methyl-2-oxopentanoate | 111,440 | 468,311 | 351,207 | 254,435 |
| 3-methyl-2-oxovalerate | 68,646 | 309,257 | 198,062 | 171,348 |
| 3-methyl-2-oxobutyrate | 14,046 | 125,751 | 119,800 | 74,419 |
| gamma-glutamylleucine | 1,060,875 | 114,832 | 280,939 | 182,965 |
| gamma-glutamylvaline | 1,046,714 | 138,055 | 221,598 | 150,513 |
| glutamine | 63,551 | 424,251 | 1,001,407 | 487,786 |
| methionine | 456,981. | 3,007,630 | 2,431,993 | 2,578,892 |

Next, the biomarkers were used to differentiate samples that had been stored at −20° C. from samples that had been stored at −80° C. For this example, a subset of the biomarkers was used to predict the storage temperature for an independent sample set of 135 serum samples that were blinded for storage temperature. Using the biomarkers, 113 of the 135 samples were predicted to be stored at −20° C. The exemplary biomarkers used for the analysis and the fold change for the biomarkers in samples stored at −20° C. compared to samples stored at −80° C. (−20° C./−80° C.), which is the ratio of the mean level of the biomarkers in samples stored at −20° C. as compared to −80° C. mean level, are shown in Table 8.

TABLE 8

Exemplary serum metabolites used to differentiate sample storage at −20° C. vs. −80° C.

| Biochemical Name | Fold Change (−20° C./80° C.) |
|---|---|
| 4-methyl-2-oxopentanoate | 0.19 |
| acetylcarnitine | 0.68 |
| alpha-ketoglutarate | 0.77 |
| caproate (6:0) | 1.46 |
| gamma-glutamylleucine | 2.54 |
| glutamine | 0.78 |
| methionine | 0.39 |

In a further demonstration, a model was generated to produce a composite score using the seven exemplary biomarkers shown in Table 9 below. In this example, the biomarkers in the model were equally weighted; biomarkers that had higher levels in samples stored at −20° C. were assigned a positive weight and biomarkers that had higher levels in samples stored at −80° C. were assigned a negative weight. The weight for each biomarker is shown in column 2 of Table 9. It should be appreciated that the coefficients (weights) are exemplary and may be refined as additional data becomes available using formal statistical analysis methods as described herein.

TABLE 9

Exemplary metabolites used to assess sample storage temperature

| Biochemical name | WEIGHT |
|---|---|
| 4-methyl-2-oxopentanoate | −1/7 |
| acetylcarnitine | −1/7 |
| alpha-ketoglutarate | −1/7 |
| caproate (6:0) | +1/7 |
| gamma-glutamylleucine | +1/7 |
| glutamine | −1/7 |
| methionine | −1/7 |

Figure 6:
FIG. 6 is a graphical representation of storage temperature scores calculated using seven exemplary biomarkers. Composite scores for samples in the reference population are indicated by open triangles, and composite score for the pseudo-observation is indicated by a closed triangle.

The biomarkers and model were used to generate a composite score to assess sample quality and the storage temperature quality parameter. The composite score for storage temperature for each sample was calculated as follows: Storage Temperature Composite Score=1/7(caproate+gamma-glutamylleucine−4-methyl-2-oxopentanoate−acetylcarnitine−alpha-ketoglutarate−glutamine−methionine). Using this model, composite scores were determined for a $4^{th}$ set of samples consisting of 43 human plasma samples stored at −80° C. In addition, to evaluate how a sample stored at −20° C. might differ from human plasma samples stored at −80° C., a pseudo-observation was created based on the ratios of −20° C. samples to −80° C. samples from sample set 1 in Table 7. The value for alpha-ketoglutarate was set to 0.1 since the metabolite was not detected in −20° C. samples. The values used for the pseudo observation are as follows: alpha-ketoglutarate=0.1, acetylcarnitine=0.034, caproate=5.435, 4-methyl-2-oxopentanoate=0.238, gamma-glutamylleucine=9.238, glutamine=0.15, and methionine=0.15. The storage temperature composite score was calculated for the pseudo-observation which represents a sample stored at −20° C. and for each of the 43 samples held at −80° C. The composite score for the pseudo-sample is 12, while the majority of composite scores for the −80° C. samples is much lower; the highest composite score calculated for the samples stored at −80° C. is only 2. The results are graphically illustrated in FIG. 6.

Example 3

Biomarkers of Sample Freeze-Thaw Cycles

Sample quality biomarkers for assessing sample quality with freeze-thaw cycles were identified using plasma, serum, and urine samples. The samples were collected and frozen at −80° C. according to sample collection protocol. Samples were thawed completely and thoroughly mixed. An aliquot of each sample (serum, urine and plasma) was taken and extracted in triplicate for metabolomics analysis (control, 1 freeze/thaw cycle). The original samples were returned to the freezer and allowed to freeze completely. The process was repeated until all five freeze thaw cycles were completed (2X=two freeze-thaw cycles, 3X=three freeze-thaw cycles, 4X=four freeze-thaw cycles, and 5X=five freeze-thaw cycles). After the levels of metabolites were determined, the data were analyzed by calculating the percent difference between the freeze-thaw samples and the control to identify biomarkers for sample freeze-thaw. One freeze-thaw cycle represents sample collection according to protocol. (The sample is collected, frozen at −80° C., shipped (frozen) to an analysis facility, and thawed at the analysis facility for metabolomics analysis.) The results are shown in Tables 10, 11, & 12 for plasma, serum, and urine, respectively.

TABLE 10

Biomarkers for assessing sample freeze-thaw cycles (plasma)

| Biochemical Name | Percent Change vs. Control | | | |
|---|---|---|---|---|
| | 2X Plasma | 3X Plasma | 4X Plasma | 5X Plasma |
| adenosine | −22.60 | −25.09 | −45.63 | −36.58 |
| succinate | 28.59 | 30.73 | 49.50 | 83.13 |
| 13-HODE + 9-HODE | −7.02 | −22.61 | −35.66 | −48.03 |
| 3-hydroxy-2-ethylpropionate | −9.91 | −16.19 | −41.69 | −50.50 |

TABLE 10-continued

Biomarkers for assessing sample freeze-thaw cycles (plasma)

| Biochemical Name | Percent Change vs. Control | | | |
|---|---|---|---|---|
| | 2X Plasma | 3X Plasma | 4X Plasma | 5X Plasma |
| caproate (6:0) | 12.65 | 16.32 | 23.08 | 23.83 |
| docosahexaenoate (DHA; 22:6n3) | −7.89 | −16.27 | −26.30 | −34.87 |
| eicosapentaenoate (EPA; 20:5n3) | −6.37 | −16.14 | −27.00 | −31.52 |
| 2'-deoxyuridine | −2.35 | −9.26 | −18.13 | −21.27 |
| phenyllactate (PLA) | −3.49 | −15.79 | −15.29 | −16.77 |
| alpha-hydroxyisovalerate | −3.56 | −13.06 | −22.62 | −24.91 |
| arachidonate (20:4n6) | −3.69 | −8.23 | −16.16 | −18.69 |
| gamma-glutamylmethionine | −2.35 | −9.07 | −16.22 | −23.27 |
| inosine | −3.09 | −11.79 | −16.00 | −27.47 |
| isoleucine | −2.04 | −12.58 | −22.05 | −24.33 |
| myristoleate (14:1n5) | −6.21 | −14.78 | −21.06 | −25.51 |
| phenylacetate | −3.31 | −11.24 | −18.82 | −19.66 |
| stearoylcarnitine (C18) | −1.44 | −5.22 | −18.75 | −26.26 |
| 2-methylcitrate | −2.38 | −6.16 | −11.95 | −19.03 |
| decanoylcarnitine (C10) | 4.69 | 9.23 | 11.70 | 19.89 |
| thymine | −1.39 | −7.55 | −10.17 | −18.57 |
| 4-phenylbutyrate | 29.91 | −62.17 | −76.43 | −53.47 |
| 12-HETE | 42.47 | −1.88 | −28.12 | −71.65 |
| alpha-hydroxyisocaproate | 5.36 | −19.95 | −26.44 | −21.40 |
| succinimide | 9.45 | −15.73 | −19.85 | −33.23 |
| 3-methyl-2-oxobutyrate | 0.01 | −10.43 | −18.33 | −21.64 |
| 3-methyl-2-oxovalerate | 0.48 | −10.56 | −16.49 | −15.53 |
| 4-methyl-2-oxopentanoate | 1.42 | −5.21 | −16.25 | −15.96 |
| 5-hydroxyhexanoate | 4.46 | −11.11 | −19.58 | −24.64 |
| isovalerate (C5) | 2.71 | −11.33 | −23.06 | −26.32 |
| urate | 5.88 | −12.72 | −17.22 | −24.31 |
| 1,5-anhydroglucitol (1,5-AG) | 5.79 | −6.90 | −10.18 | −16.92 |
| 3-(3-hydroxyphenyl)propionate | 1.10 | −11.63 | −14.48 | −20.56 |
| 3-(4-hydroxyphenyl)lactate (HPLA) | 5.07 | −9.95 | −8.59 | −17.79 |
| 4-hydroxyphenylacetate | 4.50 | −3.39 | −9.88 | −19.12 |
| docosapentaenoate (n6 DPA; 22:5n6) | −0.70 | −12.06 | −14.83 | −16.24 |
| hexanoylcarnitine (C6) | 4.65 | −5.12 | −13.51 | −23.90 |
| lactate | 4.23 | −5.86 | −12.76 | −16.90 |
| S-adenosylhomocysteine (SAH) | 0.17 | −8.58 | −13.92 | −20.37 |

TABLE 11

Biomarkers for assessing sample freeze-thaw cycles (serum)

| Biochemical Name | Percent Change vs. Control | | | |
|---|---|---|---|---|
| | 2X Serum | 3X Serum | 4X Serum | 5X Serum |
| caproate (6:0) | 61.07 | 84.21 | 118.75 | 119.82 |
| acetylcarnitine (C2) | 16.53 | 13.65 | 29.90 | 21.88 |
| adenosine | −17.74 | −15.37 | −15.58 | −17.35 |
| hexanoylcarnitine (C6) | −4.85 | −14.36 | −22.91 | −22.87 |
| palmitoylcarnitine (C16) | −6.59 | −14.01 | −15.98 | −15.11 |
| myristoylcarnitine | −11.31 | −17.12 | −23.66 | −17.14 |
| 4-phenylbutyrate | 18.99 | −37.17 | −45.93 | −55.73 |
| 2-hydroxy-3-methylvalerate | 8.69 | 3.44 | −12.46 | −15.42 |

TABLE 12

Biomarkers for assessing sample freeze-thaw cycles (urine)

| Biochemical Name | Percent Change vs. Control | | | |
|---|---|---|---|---|
| | 2X Urine | 3X Urine | 4X Urine | 5X Urine |
| 2-methylcitrate | 40.83 | 95.67 | 38.74 | 53.70 |
| phenylpyruvate | −20.29 | −33.17 | −34.57 | −16.33 |
| argininosuccinate | 13.75 | 10.14 | 15.44 | 26.41 |
| inosine | 4.42 | 1.46 | 17.09 | 15.66 |
| laurylcarnitine (C12) | −2.29 | −10.00 | −14.77 | −19.27 |

TABLE 12-continued

Biomarkers for assessing sample freeze-thaw cycles (urine)

| Biochemical Name | Percent Change vs. Control | | | |
|---|---|---|---|---|
| | 2X Urine | 3X Urine | 4X Urine | 5X Urine |
| methionine | 2.33 | −24.10 | −23.81 | −27.48 |
| uridine | 3.34 | −3.62 | 24.35 | 67.91 |

Example 4

Biomarkers for Assessing Fasting Status of an Individual

Sample quality biomarkers for assessing fasting status of an individual were identified using plasma samples, with 41 samples obtained from fasted subjects and 41 matched samples obtained from fed subjects. After the levels of metabolites were determined, the data were analyzed using matched pairs t-test to identify biomarkers for assessing fasting status of an individual. The most significant metabolites (p<0.0001) from the analysis are displayed in Table 13. Table 13 includes, for each biomarker, the biochemical name of the biomarker, the biochemical superpathway and subpathway for the biomarker, the fold change (FC) of the biomarker in samples from fed subjects compared to fasted subjects (fed/fasted) which is the ratio of the mean level of the biomarker in fed samples as compared to the fasted mean level, and the p-value determined in the statistical analysis of the data concerning the biomarkers.

TABLE 13

Biomarkers for fasting/fed status in plasma

| Biochemical Name | Biochemical Super Pathway | Biochemical Sub Pathway | FC (Fed/Fasted) | p-value |
|---|---|---|---|---|
| uridine | Nucleotide | Pyrimidine Metabolism, Uracil containing | 0.66 | 1.15E−14 |
| mannose | Carbohydrate | Fructose, Mannose and Galactose Metabolism | 0.75 | 3.24E−11 |
| xanthine | Nucleotide | Purine Metabolism, (Hypo)Xanthine/Inosine containing | 0.63 | 4.00E−10 |
| 5,6-dihydrothymine | Nucleotide | Pyrimidine Metabolism, Thymine containing | 0.85 | 6.29E−10 |
| orotate | Nucleotide | Pyrimidine Metabolism, Orotate containing | 1.34 | 9.03E−10 |
| prolylglycine | Peptide | Dipeptide | 1.92 | 1.35E−09 |
| glycoursodeoxycholate | Lipid | Secondary Bile Acid Metabolism | 1.92 | 3.29E−09 |
| methionine-sulfoxide | Amino Acid | Methionine, Cysteine, SAM and Taurine Metabolism | 1.57 | 5.14E−09 |
| caffeine | Xenobiotics | Xanthine Metabolism | 2.54 | 8.94E−09 |
| 1-stearoyl-2-linoleoyl-GPE (18:0/18:2) | Lipid | Phospholipid Metabolism | 1.41 | 1.75E−08 |
| glycodeoxycholate | Lipid | Secondary Bile Acid Metabolism | 2.98 | 2.02E−08 |
| glycochenodeoxycholate | Lipid | Primary Bile Acid Metabolism | 2.27 | 2.30E−08 |
| N-acetylglutamate | Amino Acid | Glutamate Metabolism | 1.43 | 2.52E−08 |
| glycolithocholate | Lipid | Secondary Bile Acid Metabolism | 3.82 | 4.57E−08 |
| N(2)-furoyl-glycine | Xenobiotics | Food Component/Plant | 3.18 | 8.23E−08 |
| oleoylcarnitine | Lipid | Fatty Acid Metabolism(Acyl Carnitine) | 0.80 | 8.42E−08 |
| palmitoleate (16:1n7) | Lipid | Long Chain Fatty Acid | 0.51 | 8.99E−08 |
| glycohyocholate | Lipid | Secondary Bile Acid Metabolism | 1.89 | 1.25E−07 |
| myristoleate (14:1n5) | Lipid | Long Chain Fatty Acid | 0.57 | 1.36E−07 |
| 4-guanidinobutanoate | Amino Acid | Guanidino and Acetamido Metabolism | 1.58 | 1.57E−07 |
| 1,3-7-trimethylurate | Xenobiotics | Xanthine Metabolism | 2.28 | 2.47E−07 |
| taurocholate | Lipid | Primary Bile Acid Metabolism | 2.21 | 2.56E−07 |
| pyrraline | Xenobiotics | Food Component/Plant | 1.90 | 2.77E−07 |
| 3-methyl-catechol-sulfate | Xenobiotics | Benzoate Metabolism | 3.63 | 2.97E−07 |
| glycocholate | Lipid | Primary Bile Acid Metabolism | 2.06 | 3.16E−07 |
| taurodeoxycholate | Lipid | Secondary Bile Acid Metabolism | 2.39 | 4.35E−07 |
| o-cresol-sulfate | Amino Acid | Phenylalanine and Tyrosine Metabolism | 3.12 | 4.48E−07 |
| 1-oleoyl-2-linoleoyl-GPE (18:1/18:2) | Lipid | Phospholipid Metabolism | 1.72 | 5.04E−07 |

TABLE 13-continued

Biomarkers for fasting/fed status in plasma

| Biochemical Name | Biochemical Super Pathway | Biochemical Sub Pathway | FC (Fed/ Fasted) | p-value |
|---|---|---|---|---|
| 1-palmitoyl-2-linoleoyl-GPE (16:0/18:2) | Lipid | Phospholipid Metabolism | 1.33 | 6.44E−07 |
| 4-vinylguaiacol-sulfate | Xenobiotics | Food Component/Plant | 4.16 | 6.58E−07 |
| glycodeoxycholate-sulfate | Lipid | Secondary Bile Acid Metabolism | 1.67 | 6.79E−07 |
| 1-stearoyl-2-oleoyl-GPE (18:0/18:1) | Lipid | Phospholipid Metabolism | 1.54 | 7.13E−07 |
| myristoleoylcarnitine | Lipid | Fatty Acid Metabolism(Acyl Carnitine) | 0.65 | 9.32E−07 |
| taurochenodeoxycholate | Lipid | Primary Bile Acid Metabolism | 1.98 | 1.65E−06 |
| maleate | Lipid | Fatty Acid, Dicarboxylate | 2.09 | 1.69E−06 |
| indole-3-carboxylic acid | Amino Acid | Tryptophan Metabolism | 0.69 | 2.09E−06 |
| N-acetyl-beta-alanine | Nucleotide | Pyrimidine Metabolism, Uracil containing | 0.86 | 2.28E−06 |
| octanoylcarnitine | Lipid | Fatty Acid Metabolism(Acyl Carnitine) | 0.63 | 2.67E−06 |
| dopamine-sulfate | Amino Acid | Phenylalanine and Tyrosine Metabolism | 3.63 | 2.67E−06 |
| N2,N2-dimethylguanosine | Nucleotide | Purine Metabolism, Guanine containing | 0.91 | 2.68E−06 |
| glycochenodeoxycholate-sulfate | Lipid | Primary Bile Acid Metabolism | 1.71 | 2.75E−06 |
| quinate | Xenobiotics | Food Component/Plant | 2.02 | 3.62E−06 |
| oleate-vaccenate (18:1) | Lipid | Long Chain Fatty Acid | 0.68 | 3.95E−06 |
| gamma-glutamylalanine | Peptide | Gamma-glutamyl Amino Acid | 1.25 | 3.99E−06 |
| decanoylcarnitine | Lipid | Fatty Acid Metabolism(Acyl Carnitine) | 0.64 | 4.68E−06 |
| cis-4-decenoyl-carnitine | Lipid | Fatty Acid Metabolism(Acyl Carnitine) | 0.72 | 4.97E−06 |
| hydantoin-5-propionic acid | Amino Acid | Histidine Metabolism | 1.44 | 5.83E−06 |
| linoleoylcarnitine- | Lipid | Fatty Acid Metabolism(Acyl Carnitine) | 0.83 | 6.33E−06 |
| 10-heptaadecenoate (17:1n7) | Lipid | Long Chain Fatty Acid | 0.58 | 7.10E−06 |
| oleoyl-ethanolamide | Lipid | Endocannabinoid | 0.67 | 8.72E−06 |
| O-methylcatechol-sulfate | Xenobiotics | Benzoate Metabolism | 1.87 | 1.01E−05 |
| caprylate (8:0) | Lipid | Medium Chain Fatty Acid | 7.70 | 1.29E−05 |
| azelate (nonanedioate) | Lipid | Fatty Acid, Dicarboxylate | 1.49 | 1.66E−05 |
| catechol-sulfate | Xenobiotics | Benzoate Metabolism | 1.75 | 1.66E−05 |
| laurylcarnitine | Lipid | Fatty Acid Metabolism(Acyl Carnitine) | 0.70 | 1.78E−05 |
| palmitate (16:0) | Lipid | Long Chain Fatty Acid | 0.77 | 1.99E−05 |
| N6-acetyllysine | Amino Acid | Lysine Metabolism | 1.26 | 2.57E−05 |
| palmitoylcarnitine | Lipid | Fatty Acid Metabolism(Acyl Carnitine) | 0.88 | 2.64E−05 |
| cortisone | Lipid | Steroid | 0.81 | 2.93E−05 |
| bilirubin-E-E- | Cofactors and Vitamins | Hemoglobin and Porphyrin Metabolism | 0.83 | 3.03E−05 |
| alanine | Amino Acid | Alanine and Aspartate Metabolism | 1.10 | 3.88E−05 |
| citraconate/glutaconate | Energy | TCA Cycle | 2.28 | 4.10E−05 |
| C-glycosyltryptophan | Amino Acid | Tryptophan Metabolism | 0.94 | 4.34E−05 |
| 3-hydroxy-3-methylglutarate | Lipid | Mevalonate Metabolism | 1.29 | 1.00E−04 |
| linoleate (18:2n6) | Lipid | Polyunsaturated Fatty Acid (n3 and n6) | 1.35 | 1.00E−04 |
| 4-hydroxyphenylpyruvate | Amino Acid | Phenylalanine and Tyrosine Metabolism | 1.31 | 1.00E−04 |
| methylsuccinate | Amino Acid | Leucine, Isoleucine and Valine Metabolism | 0.88 | 1.00E−04 |

TABLE 13-continued

Biomarkers for fasting/fed status in plasma

| Biochemical Name | Biochemical Super Pathway | Biochemical Sub Pathway | FC (Fed/ Fasted) | p-value |
|---|---|---|---|---|
| dihomo-linoleate (20:2n6) | Lipid | Polyunsaturated Fatty Acid (n3 and n6) | 0.70 | 1.00E−04 |
| cys-gly, oxidized | Amino Acid | Glutathione Metabolism | 0.76 | 1.00E−04 |
| docosadienoate (22:2n6) | Lipid | Polyunsaturated Fatty Acid (n3 and n6) | 0.70 | 1.00E−04 |
| eicosenoate (20:1) | Lipid | Long Chain Fatty Acid | 1.74 | 1.00E−04 |
| stearidonate (18:4n3) | Lipid | Polyunsaturated Fatty Acid (n3 and n6) | 1.99 | 1.00E−04 |
| linolenate [alpha or gamma] (18:3n3 or 6) | Lipid | Polyunsaturated Fatty Acid (n3 and n6) | 0.74 | 1.00E−04 |
| 2-linoleoyl-GPE (18:2) | Lipid | Lysolipid | 0.66 | 1.00E−04 |
| isovalerylglycine | Amino Acid | Leucine, Isoleucine and Valine Metabolism | 1.22 | 1.00E−04 |
| N6-carbamoylthreonyladenosine | Nucleotide | Purine Metabolism, Adenine containing | 0.90 | 1.00E−04 |
| palmitoyl-ethanolamide | Lipid | Endocannabinoid | 0.74 | 1.00E−04 |
| stearoyl-ethanolamide | Lipid | Endocannabinoid | 0.71 | 1.00E−04 |

Figure 7:
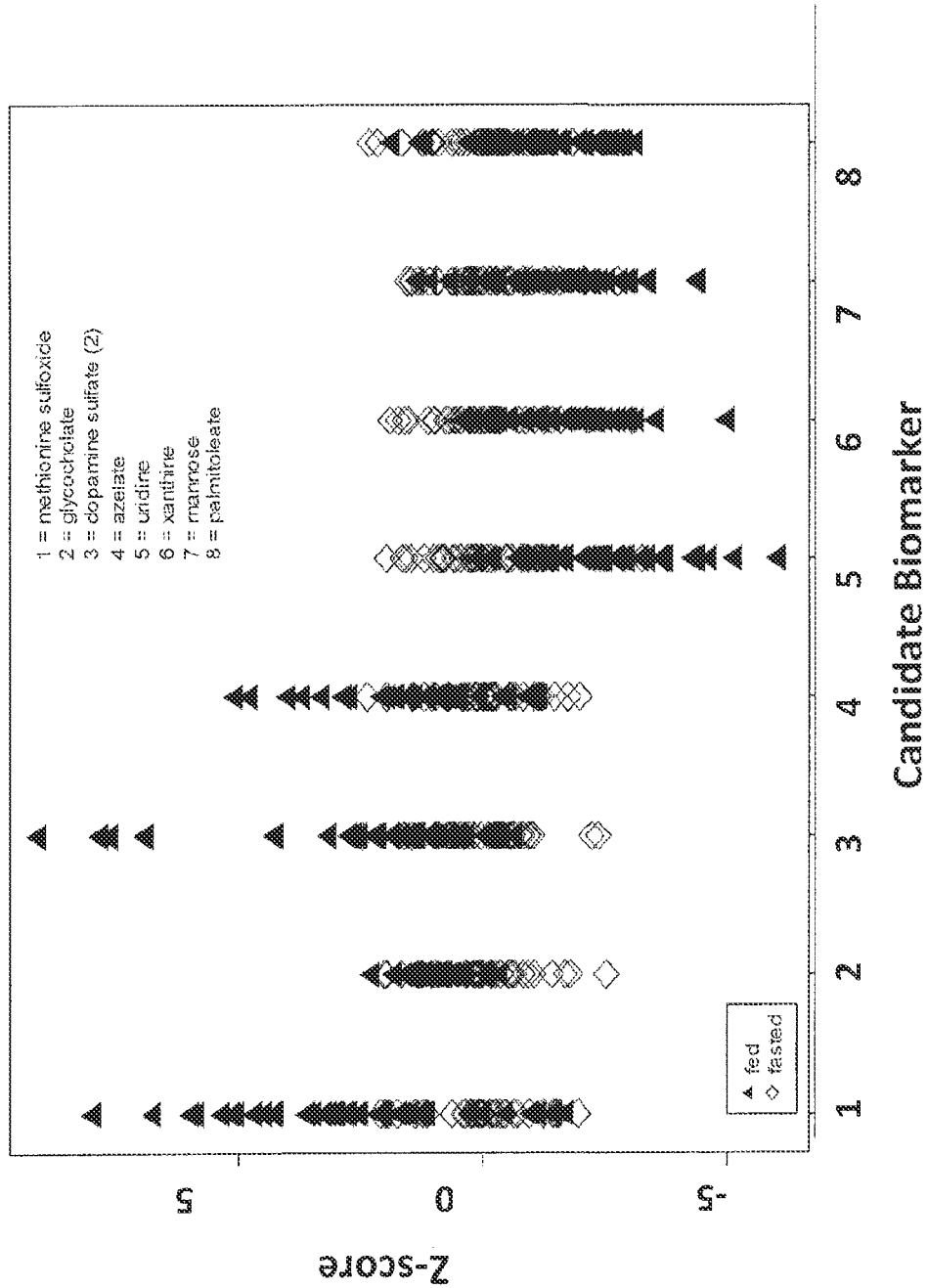
FIG. 7 is a graphical representation of levels of 8 exemplary biomarkers for assessing the sample quality parameter of fasting status. The candidate biomarkers are indicated on the x-axis, and the biomarker level is indicated on the y-axis. Fed samples are indicated by closed triangles, and fasted samples are indicated by open diamonds.

Eight exemplary biomarkers were selected based on significance and biochemical superpathway/subpathway classification. In this example, only one biomarker was selected to be representative of a given subpathway. The eight candidate biomarkers are shown in Table 14 below. Biomarkers were equally weighted; biomarkers that had higher levels in fed samples were assigned a positive weight, and biomarkers that had higher levels in fasted samples (lower levels in fed samples) were assigned a negative weight. The weight for each biomarker is shown in column 2 of Table 14. The level of each of the eight candidate biomarkers as measured by Z-score, with fasted samples as the reference population, is shown in FIG. 7. It should be appreciated that the coefficients (weights) are exemplary and may be refined as additional data becomes available using formal statistical analysis methods as described herein.

TABLE 14

Exemplary biomarkers used to assess fasting/fed status

| METABOLITE | WEIGHT |
|---|---|
| methionine sulfoxide | +1/8 |
| glycocholate | +1/8 |
| dopamine sulfate | +1/8 |
| azelate | +1/8 |
| uridine | −1/8 |
| xanthine | −1/8 |
| mannose | −1/8 |
| palmitoleate | −1/8 |

Figure 8:
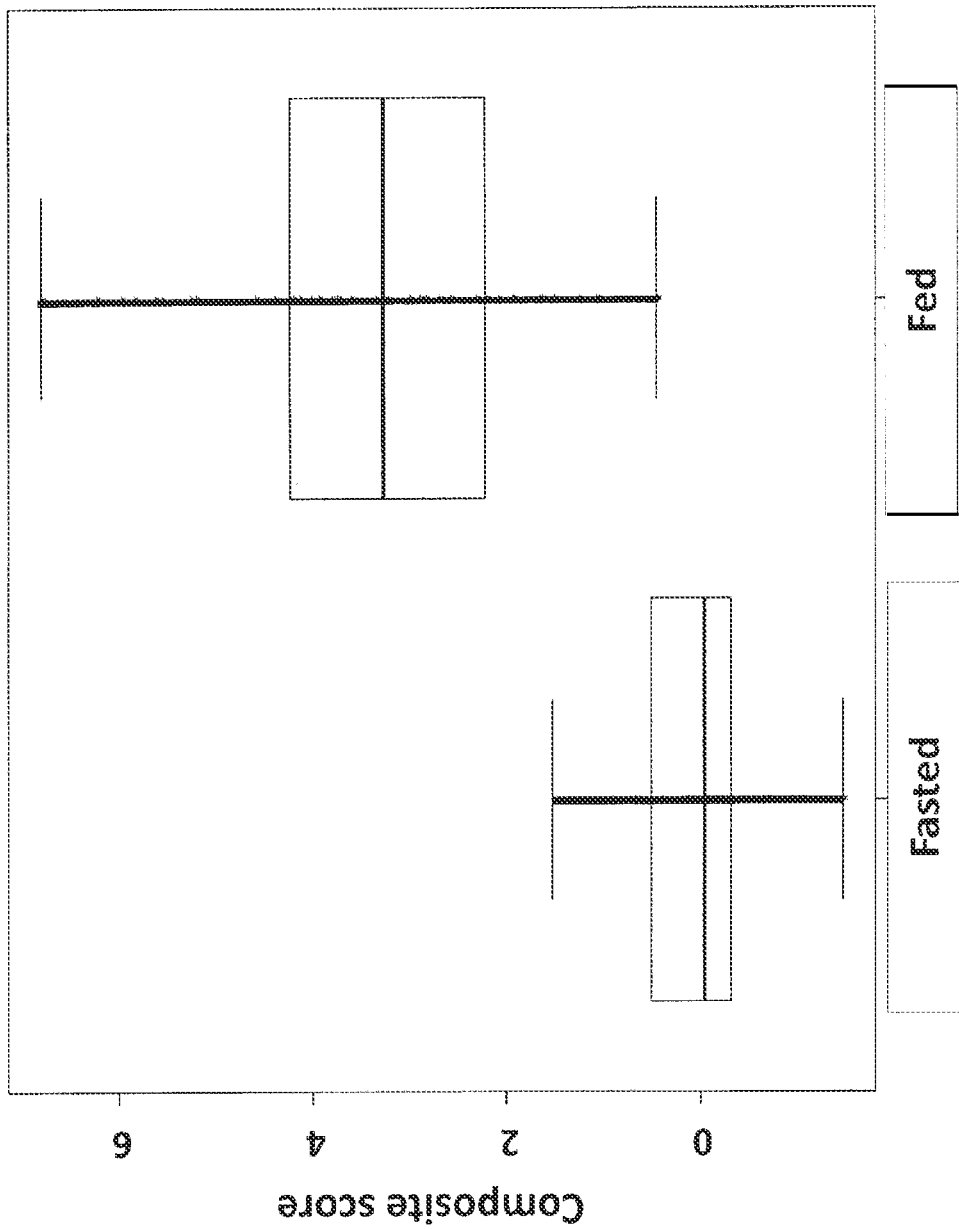
FIG. 8 is a box plot display of fasting status composite scores calculated using eight exemplary biomarkers.

The biomarkers were used to generate a composite score to assess sample quality and the fasting status quality parameter for the samples. The composite score for fasting status was calculated for each sample as follows: Fasting Status Composite Score=⅛(methionine sulfoxide+glycocholate+dopamine sulfate+azelate−uridine−xanthine−mannose−palmitoleate). The composite score was calculated for each of the 41 fasted samples and 41 fed samples, and the data are shown in boxplot format in FIG. 8.

In an exemplary use of the composite score, a rule could be established to flag potential fasting violations in samples. In this example, a rule could be set to flag any samples with a composite score >2 as potential fasting violations. Using this rule, 34 of the fed samples and none of the fasted samples were flagged as potential fasting violations.

Sample quality biomarkers for assessing fasting status of an individual were identified using adipose, liver, and muscle tissue from 8 mice fasted for 24 hours (Fasted) and 8 mice fasted for 24 hours prior to 4 hours of re-feeding (Fed). After the levels of metabolites were determined, the data were analyzed using t-tests to identify biomarkers for assessing fasting status of an individual. Significant metabolites (p<0.05) from the analysis are displayed in Tables 15, 16, and 17 for liver, muscle, and adipose tissue, respectively. Tables 15-17 include, for each biomarker, the biochemical name of the biomarker, the biochemical superpathway and subpathway for the biomarker, the fold change (FC) of the biomarker in samples from fed subjects compared to fasted subjects (fed/fasted) which is the ratio of the mean level of the biomarker in fed samples as compared to the fasted mean level, and the p-value determined in the statistical analysis of the data concerning the biomarkers.

TABLE 15

Biomarkers for fasting status in tissue (liver)

| Biochemical Name | Super Pathway | Sub Pathway | Fed/Fasted Fold Change | p-value |
|---|---|---|---|---|
| mannose | Carbohydrate | Fructose, Mannose and Galactose Metabolism | 5.23 | 7.19E−13 |
| maltopentaose | Carbohydrate | Glycogen Metabolism | 327.89 | 1.18E−11 |
| maltotriose | Carbohydrate | Glycogen Metabolism | 310.05 | 2.87E−11 |

TABLE 15-continued

Biomarkers for fasting status in tissue (liver)

| Biochemical Name | Super Pathway | Sub Pathway | Fed/Fasted Fold Change | p-value |
|---|---|---|---|---|
| suberylglycine | Lipid | Fatty Acid Metabolism (Acyl Glycine) | 0.11 | 5.81E−11 |
| histidine | Amino Acid | Histidine Metabolism | 0.46 | 2.26E−10 |
| sorbitol | Carbohydrate | Fructose, Mannose and Galactose Metabolism | 9.05 | 1.45E−09 |
| glucose | Carbohydrate | Glycolysis, Gluconeogenesis, and Pyruvate Metabolism | 6.49 | 2.56E−09 |
| 4-guanidinobutanoate | Amino Acid | Guanidino and Acetamido Metabolism | 37.93 | 3.33E−09 |
| stachydrine | Xenobiotics | Food Component/Plant | 10.57 | 8.89E−09 |
| pelargonate (9:0) | Lipid | Medium Chain Fatty Acid | 0.53 | 1.54E−08 |
| cysteine-glutathione disulfide | Amino Acid | Glutathione Metabolism | 0.35 | 3.56E−08 |
| hippurate | Xenobiotics | Benzoate Metabolism | 3.22 | 4.74E−08 |
| fructose | Carbohydrate | Fructose, Mannose and Galactose Metabolism | 5.15 | 5.20E−08 |
| lactate | Carbohydrate | Glycolysis, Gluconeogenesis, and Pyruvate Metabolism | 3.21 | 1.19E−07 |
| 2-aminobutyrate | Amino Acid | Methionine, Cysteine, SAM and Taurine Metabolism | 0.39 | 1.28E−07 |
| adipate | Lipid | Fatty Acid, Dicarboxylate | 0.26 | 1.71E−07 |
| laurate (12:0) | Lipid | Medium Chain Fatty Acid | 0.6 | 2.36E−07 |
| maltotetraose | Carbohydrate | Glycogen Metabolism | 226.73 | 3.20E−07 |
| glutathione, oxidized (GSSG) | Amino Acid | Glutathione Metabolism | 1.66 | 3.84E−07 |
| maltose | Carbohydrate | Glycogen Metabolism | 182.59 | 4.44E−07 |
| catechol sulfate | Xenobiotics | Benzoate Metabolism | 4.8 | 4.96E−07 |
| myristate (14:0) | Lipid | Long Chain Fatty Acid | 0.51 | 7.15E−07 |
| 5-ketogluconate | Xenobiotics | Food Component/Plant | 4.76 | 8.22E−07 |
| succinylcarnitine | Energy | TCA Cycle | 3 | 8.33E−07 |
| adenosine 3'-monophosphate (3'-AMP) | Nucleotide | Purine Metabolism, Adenine containing | 0.62 | 9.20E−07 |
| ribose | Carbohydrate | Pentose Metabolism | 1.98 | 1.29E−06 |
| S-methylglutathione | Amino Acid | Glutathione Metabolism | 2.18 | 1.37E−06 |
| azelate (nonanedioate) | Lipid | Fatty Acid, Dicarboxylate | 0.62 | 1.91E−06 |
| caproate (6:0) | Lipid | Medium Chain Fatty Acid | 2.53 | 2.00E−06 |
| myristoleate (14:1n5) | Lipid | Long Chain Fatty Acid | 0.45 | 2.14E−06 |
| fumarate | Energy | TCA Cycle | 1.77 | 3.11E−06 |
| kynurenine | Amino Acid | Tryptophan Metabolism | 0.39 | 4.08E−06 |
| pseudouridine | Nucleotide | Pyrimidine Metabolism, Uracil containing | 0.36 | 6.65E−06 |
| 3-methylglutarylcarnitine (C6) | Amino Acid | Leucine, Isoleucine and Valine Metabolism | 0.34 | 6.91E−06 |
| nicotinamide adenine dinucleotide (NAD+) | Cofactors and Vitamins | Nicotinate and Nicotinamide Metabolism | 0.5 | 7.76E−06 |
| tagatose | Carbohydrate | Fructose, Mannose and Galactose Metabolism | 3.99 | 8.27E−06 |
| 2-aminoadipate | Amino Acid | Lysine Metabolism | 0.24 | 8.80E−06 |
| 3-hydroxybutyrate (BHBA) | Lipid | Ketone Bodies | 0.4 | 1.00E−05 |
| 2-palmitoleoyl-GPC (16:1)* | Lipid | Lysolipid | 1.99 | 1.08E−05 |
| ornithine | Amino Acid | Urea cycle; Arginine and Proline Metabolism | 0.55 | 1.76E−05 |
| cytidine 5'-monophosphate (5'-CMP) | Nucleotide | Pyrimidine Metabolism, Cytidine containing | 0.65 | 1.78E−05 |
| docosadienoate (22:2n6) | Lipid | Polyunsaturated Fatty Acid (n3 and n6) | 1.83 | 2.39E−05 |
| 2-hydroxybutyrate (AHB) | Amino Acid | Methionine, Cysteine, SAM and Taurine Metabolism | 0.5 | 2.73E−05 |
| citrulline | Amino Acid | Urea cycle; Arginine and Proline Metabolism | 0.65 | 2.91E−05 |
| pentadecanoate (15:0) | Lipid | Long Chain Fatty Acid | 0.63 | 3.95E−05 |
| glucuronate | Carbohydrate | Aminosugar Metabolism | 1.44 | 4.50E−05 |
| nicotinamide | Cofactors and Vitamins | Nicotinate and Nicotinamide Metabolism | 1.52 | 6.14E−05 |
| phenylacetylglycine | Amino Acid | Phenylalanine and Tyrosine Metabolism | 0.57 | 6.34E−05 |
| arabonate | Cofactors and Vitamins | Ascorbate and Aldarate Metabolism | 2.5 | 6.78E−05 |
| phosphoethanolamine | Lipid | Phospholipid Metabolism | 0.71 | 7.03E−05 |
| ribulose | Carbohydrate | Pentose Metabolism | 3.24 | 7.10E−05 |
| pipecolate | Amino Acid | Lysine Metabolism | 0.65 | 9.15E−05 |
| xylonate | Carbohydrate | Pentose Metabolism | 0.62 | 9.38E−05 |
| riboflavin (Vitamin B2) | Cofactors and Vitamins | Riboflavin Metabolism | 0.67 | 9.62E−05 |
| dimethylarginine (SDMA + ADMA) | Amino Acid | Urea cycle; Arginine and Proline Metabolism | 1.62 | 0.0001 |
| myo-inositol | Lipid | Inositol Metabolism | 0.73 | 0.0001 |
| xanthine | Nucleotide | Purine Metabolism, (Hypo)Xanthine/Inosine containing | 0.84 | 0.0001 |

TABLE 15-continued

Biomarkers for fasting status in tissue (liver)

| Biochemical Name | Super Pathway | Sub Pathway | Fed/Fasted Fold Change | p-value |
|---|---|---|---|---|
| gamma-glutamylthreonine* | Peptide | Gamma-glutamyl Amino Acid | 1.96 | 0.0002 |
| citrate | Energy | TCA Cycle | 12.81 | 0.0002 |
| succinate | Energy | TCA Cycle | 1.75 | 0.0002 |
| 1,3-dihydroxyacetone | Carbohydrate | Glycolysis, Gluconeogenesis, and Pyruvate Metabolism | 5.8 | 0.0003 |
| trigonelline (N'-methylnicotinate) | Cofactors and Vitamins | Nicotinate and Nicotinamide Metabolism | 1.28 | 0.0003 |
| flavin mononucleotide (FMN) | Cofactors and Vitamins | Riboflavin Metabolism | 0.77 | 0.0003 |
| pantothenate | Cofactors and Vitamins | Pantothenate and CoA Metabolism | 0.83 | 0.0003 |
| gulono-1,4-lactone | Cofactors and Vitamins | Ascorbate and Aldarate Metabolism | 0.72 | 0.0003 |
| ophthalmate | Amino Acid | Glutathione Metabolism | 0.58 | 0.0004 |
| acetylcarnitine | Lipid | Fatty Acid Metabolism (Acyl Carnitine) | 0.51 | 0.0004 |
| 2-stearoyl-GPI (18:0)* | Lipid | Lysolipid | 0.73 | 0.0004 |
| hypoxanthine | Nucleotide | Purine Metabolism, (Hypo)Xanthine/Inosine containing | 0.73 | 0.0004 |
| gluconate | Xenobiotics | Food Component/Plant | 1.55 | 0.0004 |
| phenylpropionylglycine | Amino Acid | Phenylalanine and Tyrosine Metabolism | 1.78 | 0.0005 |
| malate | Energy | TCA Cycle | 1.64 | 0.0005 |
| tetradecanedioate | Lipid | Fatty Acid, Dicarboxylate | 0.51 | 0.0005 |
| 2-oleoyl-GPC (18:1)* | Lipid | Lysolipid | 2.59 | 0.0006 |
| 1-oleoyl-GPI (18:1)* | Lipid | Lysolipid | 0.45 | 0.0006 |
| 3-methylcrotonylglycine | Amino Acid | Leucine, Isoleucine and Valine Metabolism | 0.52 | 0.0007 |
| dihomo-linolenate (20:3n3 or n6) | Lipid | Polyunsaturated Fatty Acid (n3 and n6) | 1.46 | 0.0007 |
| N1-methyladenosine | Nucleotide | Purine Metabolism, Adenine containing | 0.69 | 0.0007 |
| cytidine | Nucleotide | Pyrimidine Metabolism, Cytidine containing | 0.85 | 0.0007 |
| Isobar: betaine aldehyde, N-methyldiethanolamine | Amino Acid | Glycine, Serine and Threonine Metabolism | 0.77 | 0.0008 |
| ribitol | Carbohydrate | Pentose Metabolism | 1.5 | 0.0009 |
| inositol 1-phosphate (I1P) | Lipid | Inositol Metabolism | 0.75 | 0.0009 |
| choline | Lipid | Phospholipid Metabolism | 0.83 | 0.0009 |
| uracil | Nucleotide | Pyrimidine Metabolism, Uracil containing | 0.69 | 0.0009 |
| 5-oxoproline | Amino Acid | Glutathione Metabolism | 0.84 | 0.001 |
| tauroursodeoxycholate | Lipid | Secondary Bile Acid Metabolism | 3.08 | 0.001 |
| kynurenate | Amino Acid | Tryptophan Metabolism | 0.39 | 0.0011 |
| alanine | Amino Acid | Alanine and Aspartate Metabolism | 1.28 | 0.0012 |
| ribose 5-phosphate | Carbohydrate | Pentose Phosphate Pathway | 1.84 | 0.0012 |
| cinnamoylglycine | Xenobiotics | Food Component/Plant | 1.58 | 0.0012 |
| gamma-glutamylleucine | Peptide | Gamma-glutamyl Amino Acid | 1.41 | 0.0013 |
| beta-alanine | Nucleotide | Pyrimidine Metabolism, Uracil containing | 0.5 | 0.0013 |
| sarcosine (N-Methylglycine) | Amino Acid | Glycine, Serine and Threonine Metabolism | 4.25 | 0.0014 |
| N-acetylalanine | Amino Acid | Alanine and Aspartate Metabolism | 0.69 | 0.0014 |
| 3-(4-hydroxyphenyl)lactate | Amino Acid | Phenylalanine and Tyrosine Metabolism | 1.52 | 0.0014 |
| isovalerylglycine | Amino Acid | Leucine, Isoleucine and Valine Metabolism | 0.55 | 0.0014 |
| homostachydrine* | Xenobiotics | Food Component/Plant | 2.66 | 0.0015 |
| palmitoyl sphingomyelin (d18:1/16:0) | Lipid | Sphingolipid Metabolism | 0.76 | 0.0016 |
| alpha-hydroxyisovalerate | Amino Acid | Leucine, Isoleucine and Valine Metabolism | 0.63 | 0.0017 |
| urea | Amino Acid | Urea cycle; Arginine and Proline Metabolism | 1.4 | 0.0017 |
| allo-threonine | Amino Acid | Glycine, Serine and Threonine Metabolism | 0.55 | 0.0018 |
| erythronate* | Carbohydrate | Aminosugar Metabolism | 1.72 | 0.0023 |
| 2-docosahexaenoyl-GPC (22:6)* | Lipid | Lysolipid | 2.8 | 0.0023 |
| margarate (17:0) | Lipid | Long Chain Fatty Acid | 0.76 | 0.0025 |
| glycine | Amino Acid | Glycine, Serine and Threonine Metabolism | 0.83 | 0.0027 |
| glycylvaline | Peptide | Dipeptide | 1.8 | 0.0027 |
| valerylglycine | Lipid | Fatty Acid Metabolism (Acyl Glycine) | 0.69 | 0.0027 |
| 1-dihomo-linolenoyl-GPC (20:3n3 or 6)* | Lipid | Lysolipid | 2.15 | 0.0029 |

TABLE 15-continued

Biomarkers for fasting status in tissue (liver)

| Biochemical Name | Super Pathway | Sub Pathway | Fed/Fasted Fold Change | p-value |
|---|---|---|---|---|
| palmitoleate (16:1n7) | Lipid | Long Chain Fatty Acid | 0.68 | 0.003 |
| 2-arachidonoyl-GPC (20:4)* | Lipid | Lysolipid | 2.39 | 0.0037 |
| hexadecanedioate | Lipid | Fatty Acid, Dicarboxylate | 0.77 | 0.0038 |
| undecanedioate | Lipid | Fatty Acid, Dicarboxylate | 0.75 | 0.0039 |
| propionylcarnitine | Lipid | Fatty Acid Metabolism (also BCAA Metabolism) | 0.61 | 0.0039 |
| equol sulfate | Xenobiotics | Food Component/Plant | 3.56 | 0.0039 |
| 10-heptadecenoate (17:1n7) | Lipid | Long Chain Fatty Acid | 0.74 | 0.0043 |
| ergothioneine | Xenobiotics | Food Component/Plant | 1.46 | 0.0043 |
| eicosapentaenoate (EPA; 20:5n3) | Lipid | Polyunsaturated Fatty Acid (n3 and n6) | 0.69 | 0.0047 |
| docosatrienoate (22:3n3) | Lipid | Polyunsaturated Fatty Acid (n3 and n6) | 1.75 | 0.0047 |
| 9,10-DIHOME | Lipid | Fatty Acid, Dihydroxy | 0.71 | 0.0049 |
| daidzein | Xenobiotics | Food Component/Plant | 2.2 | 0.0051 |
| homoserine | Amino Acid | Glycine, Serine and Threonine Metabolism | 1.88 | 0.0053 |
| creatine | Amino Acid | Creatine Metabolism | 0.73 | 0.0053 |
| 10-nonadecenoate (19:1n9) | Lipid | Long Chain Fatty Acid | 0.76 | 0.0053 |
| C-glycosyltryptophan | Amino Acid | Tryptophan Metabolism | 0.84 | 0.0057 |
| glycylproline | Peptide | Dipeptide | 1.38 | 0.0063 |
| hexanoylglycine | Lipid | Fatty Acid Metabolism (Acyl Glycine) | 0.61 | 0.0066 |
| 1-palmitoleoyl-GPC (16:1)* | Lipid | Lysolipid | 1.63 | 0.0067 |
| flavin adenine dinucleotide (FAD) | Cofactors and Vitamins | Riboflavin Metabolism | 0.85 | 0.0067 |
| 6-phosphogluconate | Carbohydrate | Pentose Phosphate Pathway | 1.35 | 0.0068 |
| 1-palmitoyl-GPC (16:0) | Lipid | Lysolipid | 1.9 | 0.0071 |
| tauro-beta-muricholate | Lipid | Primary Bile Acid Metabolism | 2.26 | 0.0071 |
| 2-linoleoyl-GPC (18:2)* | Lipid | Lysolipid | 2.14 | 0.0075 |
| kojibiose | Xenobiotics | Food Component/Plant | 1.38 | 0.0075 |
| beta-muricholate | Lipid | Primary Bile Acid Metabolism | 2.05 | 0.0076 |
| 1,5-anhydroglucitol (1,5-AG) | Carbohydrate | Glycolysis, Gluconeogenesis, and Pyruvate Metabolism | 1.31 | 0.0082 |
| 1-oleoyl-GPC (18:1) | Lipid | Lysolipid | 2.02 | 0.0087 |
| 6-beta-hydroxylithocholate | Lipid | Secondary Bile Acid Metabolism | 2.19 | 0.0088 |
| 17,18-DiHETE | Lipid | Eicosanoid | 0.76 | 0.0102 |
| 1-margaroyl-GPC (17:0) | Lipid | Lysolipid | 2.2 | 0.0109 |
| 3-indoxyl sulfate | Amino Acid | Tryptophan Metabolism | 2.02 | 0.0124 |
| palmitate (16:0) | Lipid | Long Chain Fatty Acid | 0.85 | 0.0125 |
| chenodeoxycholate | Lipid | Primary Bile Acid Metabolism | 1.56 | 0.0134 |
| deoxycarnitine | Lipid | Carnitine Metabolism | 1.24 | 0.0144 |
| oleate (18:1n9) | Lipid | Long Chain Fatty Acid | 0.72 | 0.0146 |
| 5-methyluridine (ribothymidine) | Nucleotide | Pyrimidine Metabolism, Uracil containing | 0.77 | 0.0158 |
| ascorbate (Vitamin C) | Cofactors and Vitamins | Ascorbate and Aldarate Metabolism | 8.4 | 0.0158 |
| glutathione, reduced (GSH) | Amino Acid | Glutathione Metabolism | 1.57 | 0.0161 |
| 5-aminovalerate | Amino Acid | Lysine Metabolism | 0.79 | 0.0167 |
| 15-methylpalmitate | Lipid | Fatty Acid, Branched | 0.78 | 0.0178 |
| 1-linoleoyl-GPC (18:2) | Lipid | Lysolipid | 1.73 | 0.0202 |
| stearidonate (18:4n3) | Lipid | Polyunsaturated Fatty Acid (n3 and n6) | 0.69 | 0.0204 |
| 1-stearoyl-GPI (18:0) | Lipid | Lysolipid | 0.82 | 0.0215 |
| 2-docosapentaenoyl-GPE (22:5)* | Lipid | Lysolipid | 1.56 | 0.0221 |
| beta-hydroxypyruvate | Amino Acid | Glycine, Serine and Threonine Metabolism | 1.28 | 0.0248 |
| 17-methylstearate | Lipid | Fatty Acid, Branched | 0.8 | 0.0248 |
| 2-docosahexaenoyl-GPE (22:6)* | Lipid | Lysolipid | 1.92 | 0.0253 |
| glycylleucine | Peptide | Dipeptide | 1.99 | 0.0258 |
| pyridoxate | Cofactors and Vitamins | Vitamin B6 Metabolism | 0.77 | 0.0271 |
| tryptophan | Amino Acid | Tryptophan Metabolism | 1.17 | 0.0279 |
| biopterin | Cofactors and Vitamins | Tetrahydrobiopterin Metabolism | 0.86 | 0.0281 |
| 2-arachidonoyl-GPE (20:4)* | Lipid | Lysolipid | 1.97 | 0.0282 |
| isoleucylglycine | Peptide | Dipeptide | 1.91 | 0.0309 |
| glutamine | Amino Acid | Glutamate Metabolism | 1.17 | 0.0341 |
| 1-octadecanol | Lipid | Fatty Alcohol, Long Chain | 0.86 | 0.0357 |
| 2'-deoxycytidine | Nucleotide | Pyrimidine Metabolism, Cytidine containing | 0.74 | 0.0363 |
| 3-phosphoglycerate | Carbohydrate | Glycolysis, Gluconeogenesis, and Pyruvate Metabolism | 0.64 | 0.0364 |

TABLE 15-continued

Biomarkers for fasting status in tissue (liver)

| Biochemical Name | Super Pathway | Sub Pathway | Fed/Fasted Fold Change | p-value |
|---|---|---|---|---|
| 2-hydroxyglutarate | Lipid | Fatty Acid, Dicarboxylate | 1.46 | 0.0395 |
| trans-4-hydroxyproline | Amino Acid | Urea cycle; Arginine and Proline Metabolism | 1.29 | 0.0425 |
| 1-docosahexaenoyl-GPC (22:6)* | Lipid | Lysolipid | 1.77 | 0.046 |
| gamma-glutamylglutamate | Peptide | Gamma-glutamyl Amino Acid | 1.13 | 0.0489 |
| 5-dodecenoate (12:1n7) | Lipid | Medium Chain Fatty Acid | 1.57 | 0.0491 |

TABLE 16

Biomarkers for fasting status in tissue (muscle)

| Biochemical Name | Super Pathway | Sub Pathway | Fed/Fasted Fold Change | p-value |
|---|---|---|---|---|
| stachydrine | Xenobiotics | Food Component/Plant | 4.84 | 6.51E−11 |
| 2-hydroxybutyrate (AHB) | Amino Acid | Methionine, Cysteine, SAM and Taurine Metabolism | 0.15 | 9.65E−10 |
| 3-hydroxybutyrate (BHBA) | Lipid | Ketone Bodies | 0.16 | 9.58E−09 |
| guanosine | Nucleotide | Purine Metabolism, Guanine containing | 0.65 | 1.87E−06 |
| isoleucine | Amino Acid | Leucine, Isoleucine and Valine Metabolism | 0.68 | 2.26E−06 |
| 2-aminobutyrate | Amino Acid | Methionine, Cysteine, SAM and Taurine Metabolism | 0.28 | 2.42E−06 |
| glycolate (hydroxyacetate) | Xenobiotics | Chemical | 1.83 | 2.43E−06 |
| glucose | Carbohydrate | Glycolysis, Gluconeogenesis, and Pyruvate Metabolism | 1.67 | 3.29E−06 |
| glutamine | Amino Acid | Glutamate Metabolism | 0.69 | 1.36E−05 |
| choline | Lipid | Phospholipid Metabolism | 0.46 | 1.43E−05 |
| aspartate | Amino Acid | Alanine and Aspartate Metabolism | 0.55 | 1.57E−05 |
| leucine | Amino Acid | Leucine, Isoleucine and Valine Metabolism | 0.78 | 2.24E−05 |
| uridine | Nucleotide | Pyrimidine Metabolism, Uracil containing | 0.7 | 2.56E−05 |
| ophthalmate | Amino Acid | Glutathione Metabolism | 0.51 | 3.13E−05 |
| cytidine | Nucleotide | Pyrimidine Metabolism, Cytidine containing | 0.52 | 8.46E−05 |
| N-acetylglycine | Amino Acid | Glycine, Serine and Threonine Metabolism | 0.4 | 8.48E−05 |
| 13-HODE + 9-HODE | Lipid | Fatty Acid, Monohydroxy | 0.61 | 9.34E−05 |
| ethanolamine | Lipid | Phospholipid Metabolism | 0.49 | 9.39E−05 |
| eicosenoate (20:1) | Lipid | Long Chain Fatty Acid | 0.55 | 9.64E−05 |
| succinylcarnitine | Energy | TCA Cycle | 1.79 | 9.65E−05 |
| valine | Amino Acid | Leucine, Isoleucine and Valine Metabolism | 0.81 | 0.0001 |
| phosphoenolpyruvate (PEP) | Carbohydrate | Glycolysis, Gluconeogenesis, and Pyruvate Metabolism | 3.06 | 0.0001 |
| hypoxanthine | Nucleotide | Purine Metabolism, (Hypo)Xanthine/Inosine containing | 0.63 | 0.0001 |
| tiglylcarnitine | Amino Acid | Leucine, Isoleucine and Valine Metabolism | 1.78 | 0.0002 |
| 2-phosphoglycerate | Carbohydrate | Glycolysis, Gluconeogenesis, and Pyruvate Metabolism | 3.35 | 0.0002 |
| 10-nonadecenoate (19:1n9) | Lipid | Long Chain Fatty Acid | 0.56 | 0.0002 |
| palmitoylcarnitine | Lipid | Fatty Acid Metabolism (Acyl Carnitine) | 0.16 | 0.0002 |
| uracil | Nucleotide | Pyrimidine Metabolism, Uracil containing | 0.57 | 0.0002 |
| threonine | Amino Acid | Glycine, Serine and Threonine Metabolism | 1.44 | 0.0003 |
| beta-hydroxyisovaleroylcarnitine | Amino Acid | Leucine, Isoleucine and Valine Metabolism | 1.23 | 0.0003 |
| ornithine | Amino Acid | Urea cycle; Arginine and Proline Metabolism | 2.07 | 0.0003 |
| alanyltyrosine | Peptide | Dipeptide | 2.51 | 0.0003 |
| glutamate | Amino Acid | Glutamate Metabolism | 0.67 | 0.0004 |
| glycylvaline | Peptide | Dipeptide | 1.55 | 0.0004 |

TABLE 16-continued

Biomarkers for fasting status in tissue (muscle)

| Biochemical Name | Super Pathway | Sub Pathway | Fed/Fasted Fold Change | p-value |
|---|---|---|---|---|
| serylleucine | Peptide | Dipeptide | 3.14 | 0.0004 |
| 3-phosphoglycerate | Carbohydrate | Glycolysis, Gluconeogenesis, and Pyruvate Metabolism | 4.09 | 0.0004 |
| 17-methylstearate | Lipid | Fatty Acid, Branched | 0.64 | 0.0004 |
| oleoylcarnitine | Lipid | Fatty Acid Metabolism (Acyl Carnitine) | 0.15 | 0.0004 |
| homostachydrine | Xenobiotics | Food Component/Plant | 1.94 | 0.0004 |
| lactate | Carbohydrate | Glycolysis, Gluconeogenesis, and Pyruvate Metabolism | 1.26 | 0.0005 |
| maltotriose | Carbohydrate | Glycogen Metabolism | 4.67 | 0.0005 |
| aspartylleucine | Peptide | Dipeptide | 2.9 | 0.0007 |
| malate | Energy | TCA Cycle | 0.78 | 0.0008 |
| nonadecanoate (19:0) | Lipid | Long Chain Fatty Acid | 0.67 | 0.001 |
| gamma-aminobutyrate (GABA) | Amino Acid | Glutamate Metabolism | 0.46 | 0.0012 |
| glycerate | Carbohydrate | Glycolysis, Gluconeogenesis, and Pyruvate Metabolism | 2.09 | 0.0012 |
| propionylcarnitine | Lipid | Fatty Acid Metabolism (also BCAA Metabolism) | 0.8 | 0.0018 |
| cytidine 5'-monophosphate (5'-CMP) | Nucleotide | Pyrimidine Metabolism, Cytidine containing | 1.39 | 0.002 |
| fumarate | Energy | TCA Cycle | 0.69 | 0.0026 |
| linoleate (18:2n6) | Lipid | Polyunsaturated Fatty Acid (n3 and n6) | 0.7 | 0.0027 |
| oleate (18:1n9) | Lipid | Long Chain Fatty Acid | 0.67 | 0.0029 |
| 1-docosahexaenoyl-GPC (22:6) | Lipid | Lysolipid | 0.32 | 0.0031 |
| tryptophan | Amino Acid | Tryptophan Metabolism | 0.85 | 0.0036 |
| maltose | Carbohydrate | Glycogen Metabolism | 1.97 | 0.0039 |
| octanoylcarnitine | Lipid | Fatty Acid Metabolism (Acyl Carnitine) | 0.44 | 0.0045 |
| dihomo-linoleate (20:2n6) | Lipid | Polyunsaturated Fatty Acid (n3 and n6) | 0.64 | 0.0046 |
| acetylphosphate | Energy | Oxidative Phosphorylation | 0.78 | 0.0052 |
| 4-guanidinobutanoate | Amino Acid | Guanidino and Acetamido Metabolism | 1.81 | 0.0055 |
| 1-margaroyl-GPC (17:0) | Lipid | Lysolipid | 0.62 | 0.0057 |
| alpha-hydroxyisovalerate | Amino Acid | Leucine, Isoleucine and Valine Metabolism | 0.65 | 0.0064 |
| fructose | Carbohydrate | Fructose, Mannose and Galactose Metabolism | 1.58 | 0.0065 |
| alanylleucine | Peptide | Dipeptide | 2.4 | 0.007 |
| urea | Amino Acid | Urea cycle; Arginine and Proline Metabolism | 1.4 | 0.0074 |
| alanine | Amino Acid | Alanine and Aspartate Metabolism | 1.2 | 0.0076 |
| phenylalanine | Amino Acid | Phenylalanine and Tyrosine Metabolism | 0.86 | 0.0077 |
| xanthine | Nucleotide | Purine Metabolism, (Hypo)Xanthine/Inosine containing | 0.83 | 0.0078 |
| inosine | Nucleotide | Purine Metabolism, (Hypo)Xanthine/Inosine containing | 0.86 | 0.0079 |
| glycylleucine | Peptide | Dipeptide | 1.32 | 0.0085 |
| methionine sulfoxide | Amino Acid | Methionine, Cysteine, SAM and Taurine Metabolism | 1.22 | 0.0086 |
| 1-arachidonoyl-GPC (20:4n6) | Lipid | Lysolipid | 0.42 | 0.0089 |
| 2-palmitoyl-GPC (16:0) | Lipid | Lysolipid | 0.39 | 0.0109 |
| arabitol | Carbohydrate | Pentose Metabolism | 1.39 | 0.0112 |
| butyrylcarnitine | Lipid | Fatty Acid Metabolism (also BCAA Metabolism) | 0.58 | 0.012 |
| serylphenylalanine | Peptide | Dipeptide | 1.93 | 0.0121 |
| sorbitol | Carbohydrate | Fructose, Mannose and Galactose Metabolism | 2.57 | 0.0128 |
| dihomo-linolenate (20:3n3 or n6) | Lipid | Polyunsaturated Fatty Acid (n3 and n6) | 0.73 | 0.0129 |
| 1-palmitoleoyl-GPC (16:1) | Lipid | Lysolipid | 0.39 | 0.0141 |
| 2-arachidonoyl-GPE (20:4) | Lipid | Lysolipid | 0.43 | 0.015 |
| 2-docosapentaenoyl-GPE (22:5) | Lipid | Lysolipid | 0.41 | 0.0153 |
| 1-oleoyl-GPC (18:1) | Lipid | Lysolipid | 0.39 | 0.016 |
| margarate (17:0) | Lipid | Long Chain Fatty Acid | 0.77 | 0.0172 |
| mannose | Carbohydrate | Fructose, Mannose and Galactose Metabolism | 1.44 | 0.018 |
| docosahexaenoate (DHA; 22:6n3) | Lipid | Polyunsaturated Fatty Acid (n3 and n6) | 0.8 | 0.0185 |
| 1-linoleoyl-GPC (18:2) | Lipid | Lysolipid | 0.39 | 0.0185 |
| stearate (18:0) | Lipid | Long Chain Fatty Acid | 0.83 | 0.0195 |

TABLE 16-continued

Biomarkers for fasting status in tissue (muscle)

| Biochemical Name | Super Pathway | Sub Pathway | Fed/Fasted Fold Change | p-value |
|---|---|---|---|---|
| 2-docosahexaenoyl-GPE (22:6) | Lipid | Lysolipid | 0.41 | 0.0195 |
| myo-inositol | Lipid | Inositol Metabolism | 0.85 | 0.0198 |
| hexanoylcarnitine | Lipid | Fatty Acid Metabolism (Acyl Carnitine) | 0.56 | 0.0206 |
| 2-arachidonoyl-GPC (20:4) | Lipid | Lysolipid | 0.43 | 0.0212 |
| 1-palmitoyl-GPC (16:0) | Lipid | Lysolipid | 0.49 | 0.0216 |
| 2-docosahexaenoyl-GPC (22:6) | Lipid | Lysolipid | 0.39 | 0.0225 |
| N-glycolylneuraminate | Xenobiotics | Food Component/Plant | 0.65 | 0.0258 |
| 2-oleoyl-GPC (18:1) | Lipid | Lysolipid | 0.43 | 0.0265 |
| prolylleucine | Peptide | Dipeptide | 1.21 | 0.0277 |
| 1-(1-enyl-palmitoyl)-GPE (P-16:0) | Lipid | Lysoplasmalogen | 0.75 | 0.0284 |
| dehydroascorbate | Cofactors and Vitamins | Ascorbate and Aldarate Metabolism | 1.82 | 0.0284 |
| 1-myristoyl-GPC (14:0) | Lipid | Lysolipid | 0.5 | 0.0285 |
| pipecolate | Amino Acid | Lysine Metabolism | 1.35 | 0.0287 |
| 3-(4-hydroxyphenyl)lactate | Amino Acid | Phenylalanine and Tyrosine Metabolism | 1.2 | 0.029 |
| 2-linoleoyl-GPC (18:2) | Lipid | Lysolipid | 0.45 | 0.0317 |
| 2-stearoyl-GPC (18:0) | Lipid | Lysolipid | 0.53 | 0.0364 |
| betaine | Amino Acid | Glycine, Serine and Threonine Metabolism | 1.15 | 0.0384 |
| glucose 6-phosphate | Carbohydrate | Glycolysis, Gluconeogenesis, and Pyruvate Metabolism | 2.41 | 0.0416 |
| Isobar: fructose 1,6-diphosphate, glucose 1,6-diphosphate, myo-inositol 1,4 or 1,3-diphosphate | Carbohydrate | Glycolysis, Gluconeogenesis, and Pyruvate Metabolism | 1.74 | 0.0484 |

TABLE 17

Biomarkers for fasting status in tissue (adipose)

| Biochemical Name | Super Pathway | Sub Pathway | Fed/Fasted Fold Change | p-value |
|---|---|---|---|---|
| 2-hydroxybutyrate (AHB) | Amino Acid | Methionine, Cysteine, SAM and Taurine Metabolism | 0.29 | 7.74E−06 |
| stachydrine | Xenobiotics | Food Component/Plant | 4.14 | 2.52E−05 |
| 4-guanidinobutanoate | Amino Acid | Guanidino and Acetamido Metabolism | 6.47 | 3.66E−05 |
| oleate (18:1n9) | Lipid | Long Chain Fatty Acid | 0.4 | 0.0003 |
| phosphoethanolamine | Lipid | Phospholipid Metabolism | 0.5 | 0.0003 |
| maltose | Carbohydrate | Glycogen Metabolism | 5.89 | 0.0004 |
| glycolate (hydroxyacetate) | Xenobiotics | Chemical | 1.75 | 0.0009 |
| cis-vaccenate (18:1n7) | Lipid | Long Chain Fatty Acid | 0.43 | 0.001 |
| 12,13-DiHOME | Lipid | Fatty Acid, Dihydroxy | 0.42 | 0.0028 |
| glucose | Carbohydrate | Glycolysis, Gluconeogenesis, and Pyruvate Metabolism | 2.13 | 0.0029 |
| 9,10-DiHOME | Lipid | Fatty Acid, Dihydroxy | 0.35 | 0.0031 |
| homostachydrine* | Xenobiotics | Food Component/Plant | 2.03 | 0.0034 |
| spermidine | Amino Acid | Polyamine Metabolism | 0.57 | 0.0083 |
| taurocholate | Lipid | Primary Bile Acid Metabolism | 0.13 | 0.0085 |
| nonadecanoate (19:0) | Lipid | Long Chain Fatty Acid | 0.47 | 0.012 |
| isovalerylcarnitine | Amino Acid | Leucine, Isoleucine and Valine Metabolism | 1.84 | 0.0125 |
| 17-methylstearate | Lipid | Fatty Acid, Branched | 0.48 | 0.014 |
| ethanolamine | Lipid | Phospholipid Metabolism | 0.51 | 0.0157 |
| tauro-beta-muricholate | Lipid | Primary Bile Acid Metabolism | 0.1 | 0.0157 |
| isopalmitic acid | Lipid | Fatty Acid, Branched | 0.58 | 0.0162 |
| stearate (18:0) | Lipid | Long Chain Fatty Acid | 0.67 | 0.0167 |
| eicosenoate (20:1) | Lipid | Long Chain Fatty Acid | 0.46 | 0.0186 |
| linolenate [alpha or gamma; (18:3n3 or 6)] | Lipid | Polyunsaturated Fatty Acid (n3 and n6) | 0.68 | 0.0192 |
| 1-stearoyl-GPC (18:0) | Lipid | Lysolipid | 1.95 | 0.0195 |
| beta-alanine | Nucleotide | Pyrimidine Metabolism, Uracil containing | 0.64 | 0.0238 |

TABLE 17-continued

Biomarkers for fasting status in tissue (adipose)

| Biochemical Name | Super Pathway | Sub Pathway | Fed/Fasted Fold Change | p-value |
|---|---|---|---|---|
| margarate (17:0) | Lipid | Long Chain Fatty Acid | 0.59 | 0.024 |
| isobutyrylcarnitine | Amino Acid | Leucine, Isoleucine and Valine Metabolism | 1.58 | 0.0241 |
| 1-oleoyl-GPC (18:1) | Lipid | Lysolipid | 1.61 | 0.0241 |
| ergothioneine | Xenobiotics | Food Component/Plant | 1.78 | 0.0256 |
| trans-4-hydroxyproline | Amino Acid | Urea cycle; Arginine and Proline Metabolism | 1.96 | 0.0309 |
| docosahexaenoate (DHA; 22:6n3) | Lipid | Polyunsaturated Fatty Acid (n3 and n6) | 0.74 | 0.0334 |
| palmitate (16:0) | Lipid | Long Chain Fatty Acid | 0.72 | 0.0371 |
| 1-palmitoyl-GPC (16:0) | Lipid | Lysolipid | 1.63 | 0.0389 |
| succinate | Energy | TCA Cycle | 1.5 | 0.0424 |
| stearidonate (18:4n3) | Lipid | Polyunsaturated Fatty Acid (n3 and n6) | 0.71 | 0.0443 |
| nicotinamide | Cofactors and Vitamins | Nicotinate and Nicotinamide Metabolism | 1.66 | 0.0477 |

Example 5

Assessing Sample Quality in Fasted and Non-Fasted Samples from an Individual

In one example, the quality of two human plasma samples was assessed using the biomarkers and methods described herein. Both samples were collected from the same subject; one was a fasted sample that was collected following an overnight fast and one was a non-fasted sample. The samples were stored and processed according to the same protocol. The levels of the quality biomarkers in each sample were determined and a composite score for each of the quality parameters of fasting status, sample processing and sample storage was generated and compared to a reference.

In this example, the Acceptable Reference Composite Score for Fasting is <0.51, for Storage is <0.61 and for Processing is <0.93. For Sample 1 the composite score obtained for each parameter was acceptable (−0.58 for Fasting, −0.24 for Storage, −0.25 for Processing). For Sample 2 the composite score for Fasting was unacceptable (1.98) and the composite scores for Storage and Processing were acceptable (−0.44 for Storage, −0.47 for Processing).

In this example, a composite score in the 95$^{th}$ percentile or greater is also considered to be unacceptable. For Sample 1 the composite score percentile for the Fasting, Storage and Processing parameters was 2, 23 and 35, respectively. For Sample 2 the composite score percentile for the Fasting, Storage and Processing parameters was 100, 12 and 23, respectively.

Figure 9:
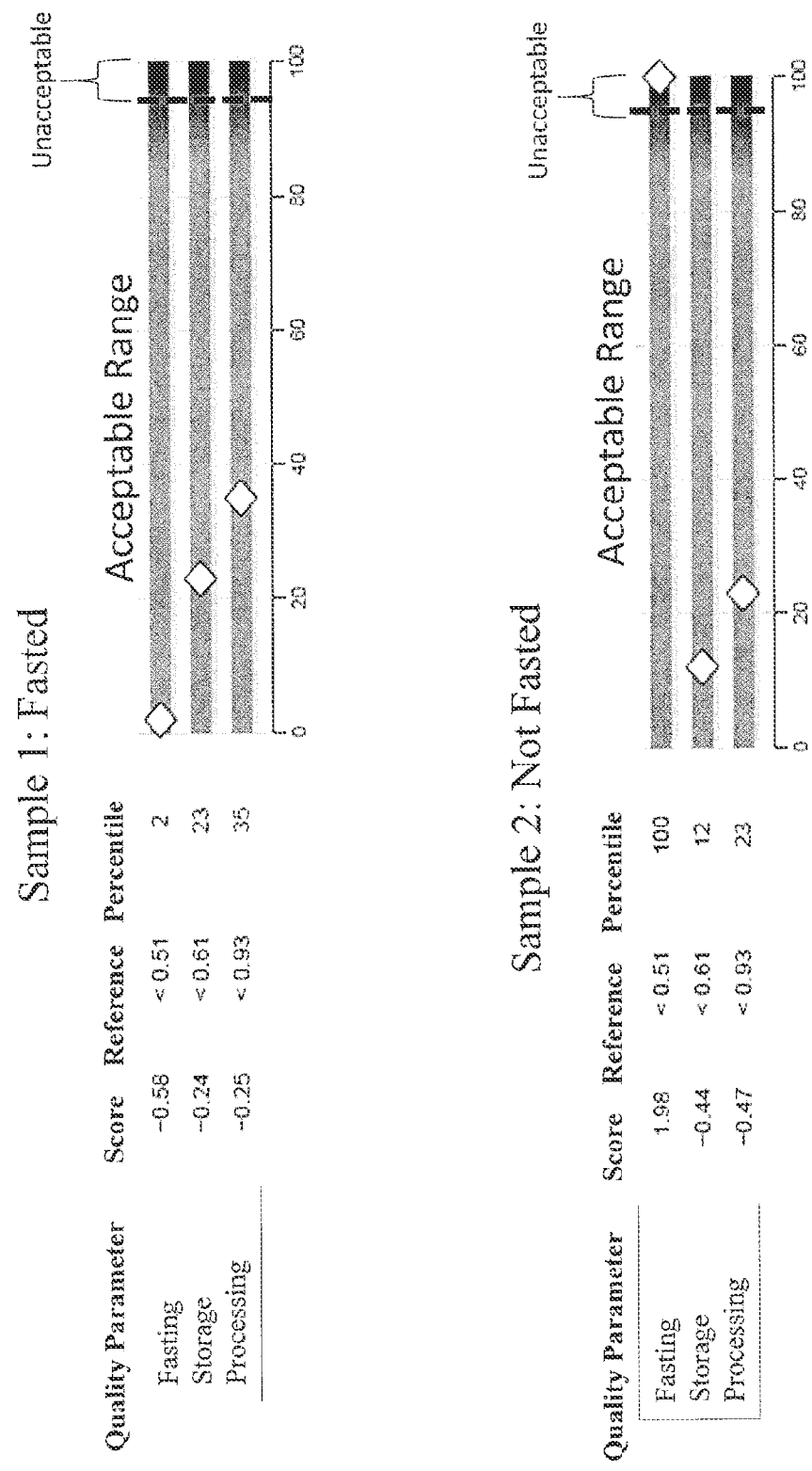
FIG. 9 is a graphical illustration of the composite scores obtained for the sample quality parameters of fasting status, sample storage and sample processing. The value obtained for the composite score for the indicated quality parameter for the sample is indicated by a diamond. "Score" means the composite score for that parameter for the sample, "Reference" means the Reference Score cut-off value, "Percentile" means the percentile of the composite score for the indicated quality parameter.

Based on the composite score analysis, both samples were acceptable for sample storage and sample processing quality parameters, Sample 1 was determined to be a fasted sample and Sample 2 was determined to be a non-fasted sample; Sample 2 was flagged as non-fasted. The composite scores obtained for each parameter are graphically illustrated in FIG. 9. In addition, the analysis of the levels obtained for the individual biomarkers that comprise the composite score for each of the quality parameters related to sample storage, sample processing and fasting status is summarized below.

The composite score for the fasting status parameter was based on the levels of the biomarkers glycocholate, palmitoleate (16:1n7), uridine, mannose, xanthine, azelate (nonanedioate), methionine sulfoxide, and dopamine sulfate measured in the sample. In Sample 1 (fasted sample), the Z-score values for all of the biomarkers were within the given reference range. For Sample 2 (non-fasted sample), three individual fasting status biomarkers (uridine, azelate, and methionine sulfoxide) had Z-scores outside the reference range, two biomarkers (xanthine, dopamine-sulfate) had borderline Z-scores and three biomarkers (glycocholate, palmitoleate (16:1n7), mannose) had Z-scores within the reference range.

Figure 10:
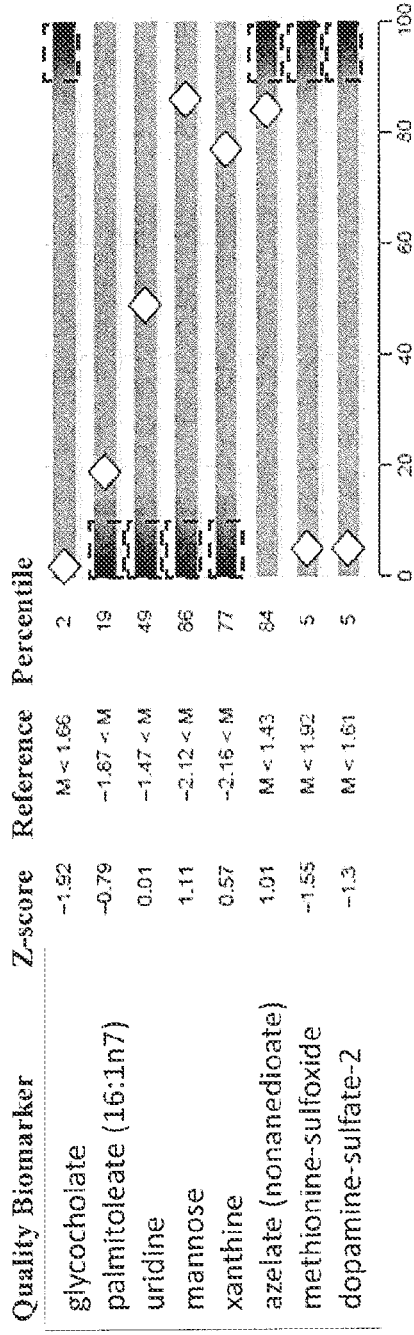
FIG. 10 is a graphical illustration of the data for the biomarkers for fasting status. The unacceptable range is indicated by the dashed boxes. The region outside the dashed box indicates the acceptable range. The value obtained for the biomarker in the sample is indicated by a diamond. "Z-Score" means the statistical score calculated for that biomarker for the sample, "Reference" means the Reference cut-off value, and "Percentile" means the percentile of the indicated quality biomarker.
Figure 10:
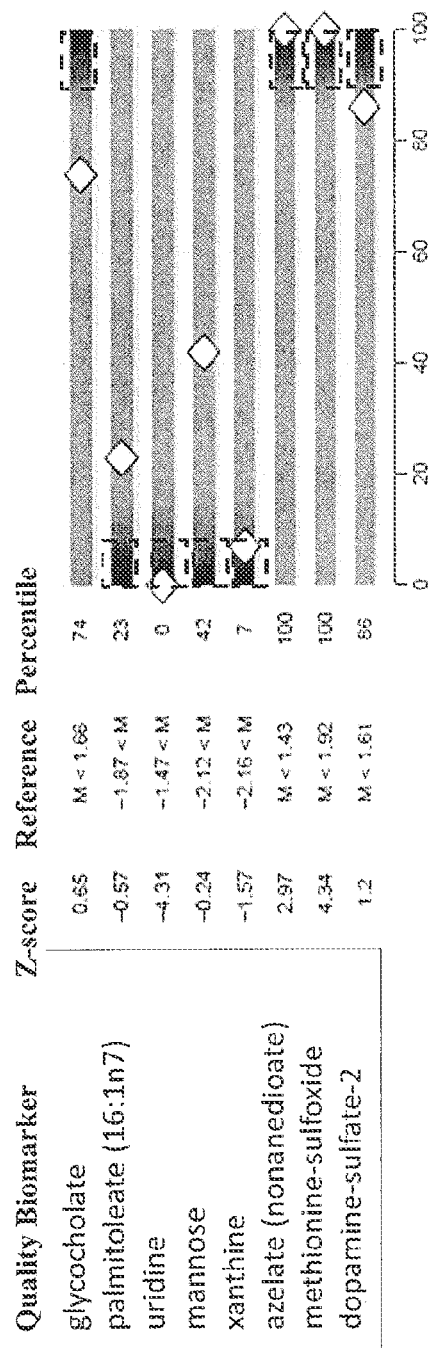

Another method of evaluating the results was based on the "Percentile", which indicates where the test sample ranks relative to the reference population for the indicated biomarker. For biomarkers that decrease when a subject was fasted (methionine sulfoxide, glycocholate, dopamine sulfate, azelate), a value above the 95$^{th}$ percentile indicates that the test sample was from a subject that was not fasted. For biomarkers that increase when a subject is fasted (uridine, xanthine, mannose, palmitoleate), a value below 5$^{th}$ percentile indicates that the test sample was from a subject that was not fasted. In the non-fasted sample, the percentile for methionine sulfoxide and azelate is above 95 and the percentile for uridine was less than 5. The fasting status biomarker data is graphically displayed in FIG. 10.

Figure 11:
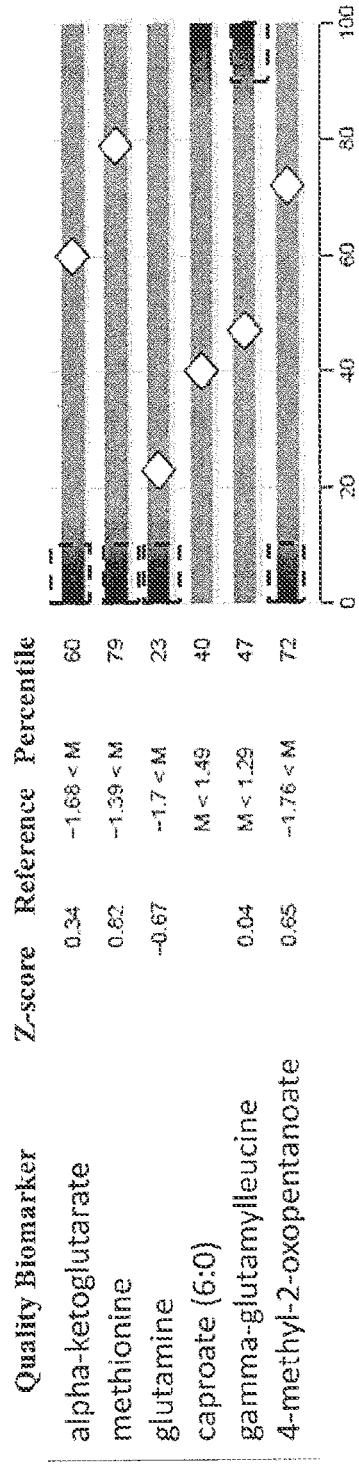
FIG. 11 is a graphical illustration of the data for the biomarkers for sample storage. The unacceptable range is indicated by the dashed boxes. The region outside the dashed box indicates the acceptable range. The value obtained for the biomarker in the sample is indicated by a diamond. "Z-Score" means the statistical score obtained for that biomarker for the sample, "Reference" means the Reference cut-off value, and "Percentile" means the percentile of the indicated quality biomarker.
Figure 11:
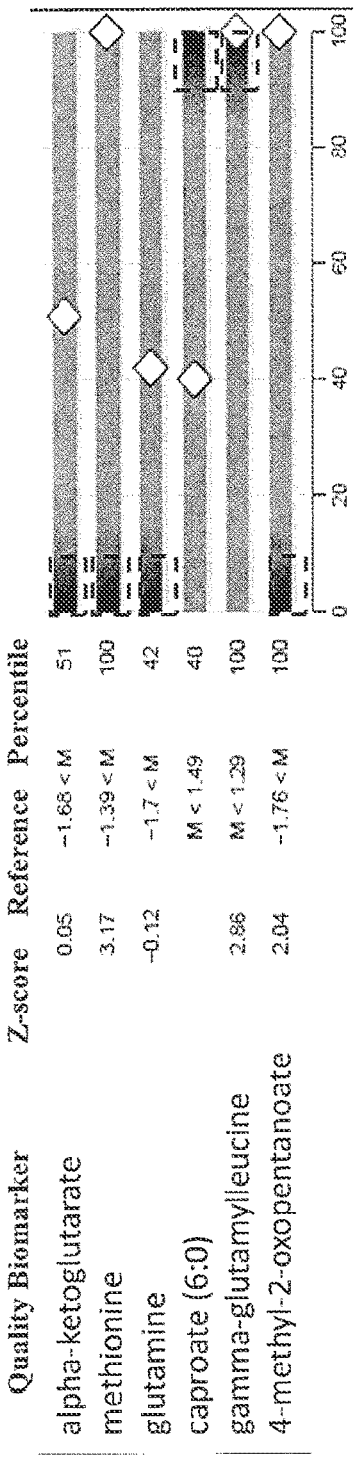

The composite score for the sample storage quality parameter was based on the levels of the biomarkers alpha-ketoglutarate, methionine, glutamine, caproate (6:0), gamma-glutamylleucine and 4-methyl-2-oxopentanoate in the sample. For the fasted sample, the levels of each biomarker for sample storage were within the reference range and for the non-fasted sample alpha-ketoglutarate, methionine, glutamine, caproate (6:0), and 4-methyl-2-oxopentanoate were within the reference range, only gamma-glutamylleucine fell outside the acceptable reference range. The storage quality biomarker data is graphically illustrated in FIG. 11.

Figure 12:
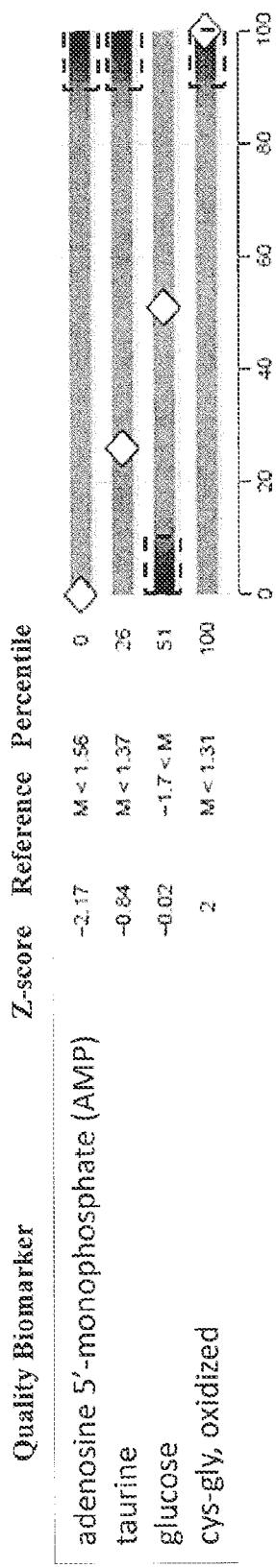
FIG. 12 is a graphical illustration of the data for biomarkers of sample processing. The unacceptable range is indicated by the dashed boxes. The region outside the dashed box indicates the acceptable range. The value obtained for the biomarker in the sample is indicated by a diamond. "Z-Score" means the statistical score for that biomarker for the sample, "Reference" means the Reference cut-off value, and "Percentile" means the percentile of the indicated quality biomarker.
Figure 12:
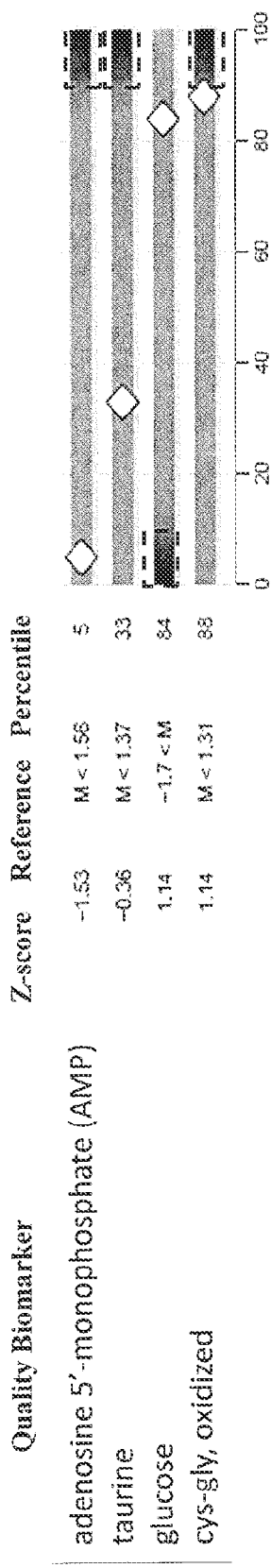

The composite score for the sample processing quality parameter was based on the levels of the biomarkers adenosine 5'-monophosphate (AMP), taurine, glucose and cys-gly, oxidized in the sample. The results obtained for each biomarker for sample processing for both samples indicated that adenosine 5'-monophosphate (AMP), taurine, and glucose were within the reference range; cys-gly oxidized fell outside the acceptable reference range for Sample 1 and was borderline for Sample 2. The sample processing biomarker data is graphically illustrated in FIG. 12.

Example 6

Biomarkers of Sample Storage Temperature (New to PCT)

Sample quality biomarkers for assessing sample storage over time, at −20° C. and −80° C. were identified. Plasma samples were stored for 1 month, 3 months, or 6 months at −20° C. or at −80° C. before being processed for analysis. For each time point and storage condition, ten plasma samples were used. After the levels of metabolites were determined, the data were analyzed to identify biomarkers for assessing sample storage at different storage temperatures over time. Welch's two-sample t-tests were performed to compare the two temperature conditions at each timepoint. Metabolites that differentiated samples stored at −20° C. from those stored at −80° C. are displayed in Table 18. Table 18 includes, for each biomarker, the biochemical name of the biomarker and the fold change for the biomarker in samples stored at −20° C. compared to samples stored at −80° C. (−20° C./−80° C.), which is the ratio of the mean level of the biomarkers in samples stored at −20° C. as compared to the −80° C. mean level. The fold change values are shown for the 1 month, 3 month, and 6 month timepoints.

TABLE 18

Biomarker metabolites that differentiate sample storage at −20° C. vs. −80° C.

| | Fold Change (−20° C./80° C.) | | |
|---|---|---|---|
| Biochemical Name | 1 Month | 3 Months | 6 Months |
| 4-methyl-2-oxopentanoate | 0.8 | 0.43 | 0.25 |
| alpha-ketoglutarate | 0.84 | 0.46 | 0.26 |
| glutamine | 0.72 | 0.39 | 0.29 |
| methionine | 0.96 | 0.88 | 0.85 |
| gamma-glutamylleucine | 1.26 | 1.58 | 1.8 |
| caproate (6:0) | 1.08 | 1.15 | 1.26 |
| pyruvate | 0.32 | 0.15 | 0.16 |
| gamma-glutamylglycine | 3.34 | 4.44 | 4.92 |
| gamma-glutamylmethionine | 7.44 | 9.44 | 9.39 |
| gamma-glutamylhistidine | 1.86 | 2.65 | 3 |
| methionine sulfoxide | 1.25 | 1.49 | 2.14 |
| isovalerate | 1.36 | 1.94 | 2.46 |
| valylvaline | 1.25 | 1.55 | 1.91 |
| gamma-glutamylglutamine | 2.14 | 1.63 | 1.29 |
| gamma-glutamyltyrosine | 1.27 | 1.62 | 1.88 |
| succinate | 1.17 | 1.44 | 1.68 |
| 3-methyl-2-oxobutyrate | 0.83 | 0.5 | 0.26 |
| methionylalanine | 1.14 | 1.21 | 1.28 |
| 3-methyl-2-oxovalerate | 0.89 | 0.64 | 0.43 |
| seryltyrosine | 1.21 | 1.18 | 1.22 |
| glutamate | 1.11 | 1.15 | 1.22 |
| aspartate | 0.92 | 0.78 | 0.8 |
| 4-guanidinobutanoate | 1.09 | 1.24 | 1.52 |
| inosine | 1.4 | 1.37 | 1.58 |
| 5-KETE | 0.7 | 0.57 | 0.74 |
| N6-methyladenosine | 0.46 | 0.38 | 0.38 |
| phenylalanyllysine | 1.08 | 1.24 | 1.3 |
| butyrylcarnitine | 0.96 | 0.7 | 0.53 |
| gamma-glutamylphenylalanine | 1.16 | 1.34 | 1.46 |
| bilirubin (E,E) | 0.83 | 0.52 | 0.45 |
| urate | 0.9 | 0.8 | 0.94 |
| asparagine | 0.98 | 0.81 | 0.78 |
| gamma-glutamylvaline | 1.11 | 1.16 | 1.25 |
| bilirubin (Z,Z) | 0.81 | 0.53 | 0.35 |
| xanthine | 0.91 | 0.82 | 0.96 |
| leucylalanine | 1.09 | 1.08 | 1.17 |
| 1-oleoyl-2-docosahexaenoyl-GPC (18:1/22:6) | 0.9 | 0.86 | 0.8 |
| 1-palmitoyl-2-docosahexaenoyl-GPC (16:0/22:6) | 0.9 | 0.87 | 0.85 |
| histidylalanine | 1.07 | 1.06 | 1.16 |

TABLE 18-continued

Biomarker metabolites that differentiate sample storage at −20° C. vs. −80° C.

| | Fold Change (−20° C./80° C.) | | |
|---|---|---|---|
| Biochemical Name | 1 Month | 3 Months | 6 Months |
| 1-(1-enyl-stearoyl)-2-arachidonoyl-GPE (P-18:0/20:4) | 0.91 | 0.85 | 0.82 |
| succinylcarnitine | 1.24 | 1.31 | 1.6 |
| gamma-glutamylthreonine | 1.11 | 1.4 | 1.61 |
| 1-(1-enyl-palmitoyl)-2-arachidonoyl-GPE (P-16:0/20:4) | 0.94 | 0.88 | 0.86 |
| N-formylmethionine | 0.98 | 0.88 | 0.86 |
| alpha-ketobutyrate | 0.56 | 0.45 | 0.34 |
| N-acetylmethionine | 0.93 | 0.85 | 0.78 |
| 16a-hydroxy DHEA 3-sulfate | 1.03 | 0.89 | 0.77 |
| 1-palmityl-2-arachidonoyl-GPC (O-16:0/20:4) | 0.92 | 0.93 | 0.91 |
| cysteine sulfinic acid | 1.17 | 1.27 | 1.4 |
| biliverdin | 1.66 | 0.84 | 0.37 |
| 1-(1-enyl-palmitoyl)-2-docosahexaenoyl-GPE (P-16:0/22:6) | 0.91 | 0.83 | 0.77 |
| valylglycine | 1.09 | 1.06 | 1.14 |

A model was generated to produce a composite score using the levels of six exemplary biomarkers, caproate, gamma-glutamylleucine, 4-methyl-2-oxopentanoate, alpha-ketoglutarate, glutamine, and methionine. In this example, the biomarkers in the model were equally weighted; biomarkers that had higher levels in samples stored at −20° C. were assigned a positive weight and biomarkers that had higher levels in samples stored at −80° C. were assigned a negative weight. Thus, the biomarkers caproate and gamma-glutamylleucine were assigned a positive weight; the biomarkers 4-methyl-2-oxopentanoate, alpha-ketoglutarate, glutamine, and methionine were assigned a negative weight. The weighted value can be used as a coefficient in the generated model. It should be appreciated that the coefficients (weights) are exemplary and may be refined using formal statistical analysis methods as described herein.

The biomarkers and model can be used to generate a composite score to assess sample quality and a storage temperature quality parameter. For example, the composite score for storage temperature for a sample may be calculated as follows: Storage Temperature Composite Score=⅙(caproate+gamma-glutamylleucine−4-methyl-2-oxopentanoate−alpha-ketoglutarate−glutamine−methionine).

Example 7

Assessing Sample Quality

Metabolic profiling was used as described herein to assess sample quality simultaneously with performing intended use analysis of 98 plasma samples that were evaluated in five analytical batches. The samples were reportedly collected according to the determined sample collection protocol (i.e., plasma separated from whole blood within one hour of collection and freezing immediately at −80° C.).

Metabolic profiling identified between 476 and 806 metabolites in the samples. After the levels of the metabolites were determined, statistical analysis was performed to determine z-score values for each of the metabolites. Sample quality was assessed using the biomarkers and methods described herein. Further, the levels of quality biomarkers were used to generate a composite score for each of the quality parameters of sample processing, sample storage, stability and fasting status. Based on this analysis, samples were flagged for having aberrant scores for biomarkers of Storage (4 samples), Stability (16 samples) or Processing (2 samples), and five (5) samples were flagged as having aberrant quality biomarker scores for Storage Temperature, Stability and Processing. The aberrant quality biomarker scores indicate that the samples were not properly handled and were not processed according to protocol. No samples were flagged as being fed samples. The scores are summarized in Table 19. Failing/flagged scores are indicated by bold italics. The detailed results of the analysis for the five samples that failed all three quality parameters related to sample handling and processing are detailed below.

TABLE 19

Summary of Quality Scores for Flagged Samples

| Sample Number | Batch Number | Storage Score | Stability Score | Processing Score | Fasting |
|---|---|---|---|---|---|
| 1 | 85 | *-2.805* | *-0.321* | -2.300 | Fasted |
| 2 | 24 | *-1.435* | 0.812 | -1.423 | Fasted |
| 3 | 85 | -0.912 | *-0.422* | -1.100 | Fasted |
| 4 | 24 | *-1.356* | 0.081 | -1.073 | Fasted |
| 5 | 24 | -0.517 | *1.489* | -0.987 | Fasted |
| 6 | 24 | -1.082 | *1.137* | -0.963 | Fasted |
| 7 | 24 | -0.965 | *0.822* | -0.912 | Fasted |
| 8 | 24 | -0.630 | *-0.421* | -0.287 | Fasted |
| 9 | 91 | *-1.794* | -0.174 | -0.240 | Fasted |
| 10 | 91 | -0.597 | *-0.410* | -0.053 | Fasted |
| 11 | 24 | 0.221 | *0.834* | -0.034 | Fasted |
| 12 | 85 | 0.021 | *-0.462* | -0.014 | Fasted |
| 13 | 91 | 0.452 | *-0.525* | 0.013 | Fasted |
| 14 | 85 | 0.452 | *-0.556* | 0.029 | Fasted |
| 15 | 24 | 0.377 | *-0.746* | 0.183 | Fasted |
| 16 | 85 | 0.135 | *-1.170* | 0.215 | Fasted |
| 17 | 85 | 0.640 | *1.248* | 0.395 | Fasted |
| 18 | 73 | -0.395 | *-0.412* | Flag | Fasted |
| 19 | 73 | -0.615 | *-0.409* | Flag | Fasted |
| A | 91 | *1.671* | *-0.319* | *0.083* | Fasted |
| B | 24 | *0.131* | *-0.445* | *0.800* | Fasted |
| C | 85 | *9.377* | *0.818* | *7.335* | Fasted |
| D | 73 | *2.285* | *-0.508* | *7.34* | Fasted |
| E | 13 | *-1.293* | *0.127* | *-0.97* | Fasted |

In the first sample (Sample A), metabolic profiling identified 632 metabolites in the sample and analysis showed that the sample quality biomarkers 5-oxoproline, lactate, glutamate, pyruvate, arginine, glucose, and cysteinylglycine, were aberrant based on the calculated Z-scores. The composite score for sample processing was also determined to be unacceptable (Score <$5^{th}$ percentile). A composite score in the $95^{th}$ percentile or greater is also considered to be unacceptable. For this sample, the Z-scores calculated for the quality biomarkers and the composite Z-score calculated for fasting status were acceptable while the composite score percentiles for the Storage and Processing parameters were not within the acceptable range. The Z-scores that were calculated for the levels of the aberrant biomarkers for this sample are shown in Table 20.

TABLE 20

Sample A: Aberrant Sample Quality Biomarkers

| Biochemical Name | Z-score |
|---|---|
| 5-oxoproline | 2.83 |
| Lactate | 2.64 |
| Glutamate | 2.31 |

TABLE 20-continued

Sample A: Aberrant Sample Quality Biomarkers

| Biochemical Name | Z-score |
|---|---|
| Cysteinylglycine | 2.27 |
| Pyruvate | 1.95 |
| Arginine | -3.22 |
| Glucose | -4.81 |

Based on the levels of the quality biomarkers in the sample, the sample quality parameter of sample processing was flagged (i.e., identified as aberrant), and the sample was determined to not have been handled according to the defined sample collection protocol.

In the same sample, metabolic profiling also identified biomarkers of subject compliance. The biomarkers 2-hydroxyacetaminophen sulfate, 4-acetaminophen sulfate, and 4-acetamidophenylglucuronide were elevated in the plasma sample relative to control samples with Z-score values of 3.35, 3.10, and 2.93, respectively. Based on the presence and levels of these biomarkers, the subject was determined to be undergoing acetaminophen treatment at the time of sample collection. This result may indicate that the subject was not in compliance with protocol if acetaminophen was not allowed prior to sample collection; alternatively, if acetaminophen was allowed, then the subject may be in compliance with instructions.

In a second plasma sample (Sample B), metabolic profiling identified 806 metabolites in the sample. After the levels of the metabolites were determined, statistical analysis was performed to determine Z-score values for each of the metabolites; the sample quality biomarkers pyruvate, cys-gly (oxidized), 5-oxoproline, fumarate, inosine, ornithine, lactate, glucose, arginine, oleoyl ethanolamide, sphingosine 1-phosphate, sphinganine-1-phosphate, ergothioneine, and cysteinylglycine, were determined to be aberrant. Based on the scores calculated for the levels of the quality biomarkers in the sample, the sample quality parameter of sample processing was identified as aberrant, and the sample was determined to not have been handled according to the defined sample collection protocol. The Z-scores calculated for each of the biomarkers are shown in Table 21.

TABLE 21

Sample B: Aberrant Sample Quality Biomarkers

| Biochemical Name | Z-score |
|---|---|
| Pyruvate | 2.87 |
| Cys-gly, oxidized | 2.80 |
| 5-oxoproline | 2.45 |
| Sphingosine 1-phosphate | 2.34 |
| Oleoyl ethanolamide | 2.10 |
| Sphinganine-1-phosphate | 2.08 |
| Ergothioneine | 1.99 |
| Fumarate | 1.81 |
| Inosine | 1.71 |
| Cysteinylglycine | 1.65 |
| Ornithine | 1.60 |
| Lactate | 1.54 |
| Glucose | -1.68 |
| Arginine | -3.07 |

In a third plasma sample (Sample C), metabolic profiling identified 627 metabolites in the sample. After the levels of the metabolites were determined, statistical analysis was performed to calculate z-score values for each of the metabolites. Sample quality was assessed using the biomarkers described herein. The sample quality biomarkers 5-oxoproline, cys-gly (oxidized), pyruvate, fumarate, lactate, glycerol, hypoxanthine, arginine, mannose, glucose sphinganine-1-phosphate, and sphingosine 1-phosphate, were determined to be aberrant. Based on the calculated Z-scores for the levels of the quality biomarkers measured in the sample, the sample quality parameter of sample processing was identified as failing the quality metric, and the sample was determined to not have been handled according to the defined sample collection protocol. The Z-scores calculated for levels of the biomarkers are shown in Table 22.

TABLE 22

Sample C: Aberrant Sample Quality Biomarkers

| Biochemical Name | Z-score |
| --- | --- |
| 5-oxoproline | 5.22 |
| Cys-gly, oxidized | 4.3 |
| Pyruvate | 3.66 |
| Sphinganine-1-phosphate | 3.64 |
| Spingosine 1-phosphate | 3.42 |
| Fumarate | 3.17 |
| Lactate | 2.95 |
| Glycerol | −2.66 |
| Hypoxanthine | −4.54 |
| Arginine | −6.07 |
| Mannose | −9.51 |
| Glucose | −32.3 |

In a fourth plasma sample (Sample D), metabolic profiling identified 616 metabolites in the sample. The sample quality biomarkers hypoxanthine, lactate, inosine, lysine, arginine, mannose, and glucose were determined to be aberrant, indicating problems with the sample quality parameter of sample processing. Thus, the sample was determined to not have been handled according to the defined sample collection protocol. The calculated Z-scores for the measured levels of the biomarkers are shown in Table 23.

TABLE 23

Sample D: Aberrant Sample Quality Biomarkers

| Biochemical Name | Z-score |
| --- | --- |
| Hypoxanthine | 2.42 |
| Lactate | 2.33 |
| Inosine | 2.28 |
| Lysine | −2.64 |
| Arginine | −3.84 |
| Mannose | −9.54 |
| Glucose | −25.3 |

In a fifth plasma sample (Sample E), metabolic profiling identified 476 metabolites in the sample. After the levels of the metabolites were determined, statistical analysis was performed to calculate z-score values for each of the metabolites. Sample quality was assessed using the biomarkers described herein. The sample quality biomarkers 5-oxoproline, glutamate, fumarate, palmitoylcarnitine, and linoleoylcarnitine were determined to be aberrant. Based on the levels of the quality biomarkers in the sample, the time incubated as whole blood prior to separation, a quality parameter of sample processing, was flagged. The sample was determined to have had a delayed separation of plasma from whole blood, indicating that the sample was not handled according to the defined sample collection protocol. The levels of the biomarkers (Z-score) are shown in Table 23.

TABLE 24

Sample E: Aberrant Sample Quality Biomarkers

| Biochemical Name | Z-score |
| --- | --- |
| 5-oxoproline | 13.04 |
| glutamate | 4.18 |
| fumarate | 3.47 |
| palmitoylcarnitine | −2.38 |
| linoleoylcarnitine | −2.28 |

Example 8

Assessing Sample Handling in Clinical Samples

In another example, metabolic profiling was performed as described herein and the biomarkers and algorithms described herein were used in the process as outlined in FIGS. 1 and 2 to simultaneously assess sample quality while performing intended use analysis of 937 clinical plasma samples. Using these systems, methods, biomarkers and algorithms, of the 937 samples tested, 47 samples were flagged as having quality problems due to sample handling in the clinic. The types of sample quality issues that were identified in these flagged samples include use of the wrong collection tube (protocol calls for EDTA but flagged samples do not meet that requirement), delayed processing, improper or delayed separation of whole blood, improper collection temperature, and hemolysis. The results are summarized in Table 24 and notes describing the quality biomarker signatures indicating sample should be flagged for quality issues are summarized in Table 26. The numbers in Table 26 indicate the score calculated for that biomarker in that sample. The signatures for each sample indicating that the sample should be flagged for having aberrant quality are based on combinations of biomarkers. The aberrant biomarkers are not necessarily identical for each sample affected by the same quality issue; rather it is the composite score for overlapping sets of biomarkers and the various combinations of biomarkers that indicate which quality parameter is aberrant.

TABLE 25

Summary of Flagged Samples Based on Aberrant Sample Quality Biomarkers and Resulting Quality Scores.

| Quality Issue | Number of Samples |
| --- | --- |
| Improper Collection Tube (non-EDTA) | 26 |
| Delayed sample processing | 3 |
| Improper or delayed whole blood separation | 6 |
| Incorrect Temperature | 1 |
| Hemolysis | 11 |

TABLE 26

Quality Marker Signatures Measured in Flagged Samples

Improper Collection Tube (non-EDTA)

Notes: The following scores for the biomarkers indicate improper collection tube:
iminodiacetate ranged from −12.35 to −2.83 and EDTA ranged from −11.85 to −3.3;
several samples having citrate levels ranging from −7 to −4 indicate heparin collection
Delayed Separation and/or Delayed Processing Notes: The following biomarkers signatures were measured indicating samples should
be flagged:
Example Signature #1) Pyruvate 4.26; 5-oxoproline 3.17; Lactate 3.13; Long-chain
acylcarnitines >2; Arginine −5.81; Glucose −3.6
Example Signature #2) Cys-gly, oxidized 3.30; 5-oxoproline 3.28; Lactate 3.17;
Malate 2.89; Cysteinylglycine 2.63; Ornithine 2.28; Pyruvate 2.12; Hypoxanthine −3.14;
Glycerol −4.16; Arginine −5.16; Glucose −7.85
Improper Handling:

Notes: The following biomarker signatures were measured indicating samples were
not handled according to protocol:
Example Signature #1) 5-oxoproline 2.83 Lactate 2.64 Glutamate 2.31
Cysteinylglycine 2.27 Pyruvate 1.95 Arginine −3.22 Glucose −4.81
Example Signature #2) 5-oxoproline 5.22 Cys-gly, oxidized 4.30 Pyruvate 3.66
Sphinganine-1-phosphate 3.64 Spingosine 1-phosphate 3.42 Fumarate 3.17 Lactate
2.95 All BCKA's have Z >2 and several acylcarntines have Z >2. Glycerol −2.66
Hypoxanthine −4.54 Arginine −6.07 Glucose −32.3 Mannose −9.51
Example Signature #3) Cys-Gly 2.20 5-oxoproline 3.27 lactate 2.70 pyruvate 2.69
Cys-Gly, ox 2.33 oleoylcarnitine 2.41 ornithine 2.18 hypoxanthine −5.25 glucose −3.24
arginine −1.91 (increased lactate, pyruvate, and ornithine coupled with
decreased glucose and arginine is suggestive of improper sample handling)
Example Signature #4) 1-palmitoylglycerol 6.37 hypoxanthine 5.26 inosine 5.12 2-
palmityolglycerol 3.82 5-oxoproline 3.03 azelate 2.96 oleoylcarnitine 2.52 malate
2.39 lactate 2.18 stearoylcarnitine 2.16 IDA −3.57 urea −3.00 1,5-AG −2.76
mannose −2.67 Arg −2.35 citrulline −2.17 glucose −1.93
Example Signature #5) pyruvate 2.66, lactate 2.27, arginine −5.05, hypoxanthine −4.34,
inosine −3.10, glucose −3.02
Improper Temperature:

Notes: The following signature indicated the sample was not held at the proper
temperature:
Example Signature: Hypoxanthine 2.42 Lactate 2.33 Inosine 2.28 Lysine −2.64
Arginine −3.84 Mannose −9.54 Glucose −25.30
Hemolysis:

Notes: When one or more of the listed biomarkers have Z-scores >2 the sample may
be flagged for hemolysis:
heme, 3-phosphoglycerate, 2,3-diphosphoglycerate, and biliverdin

We claim:

1. A system to assess sample quality, the system comprising:
   an analytical device comprising mass spectrometry or mass spectroscopy analytical capabilities, the device configured to detect and measure levels of one or more small molecules in a biological sample obtained from a subject, wherein at least a portion of the one or more small molecules are one or more sample quality biomarkers and wherein at least a portion of the one or more small molecules are measured as a part of metabolic profiling analysis or a biochemical analysis; and
   a database in communication with the analytical device, said database being configured to automatically receive from the analytical device data corresponding to the measured level(s) of the one or more small molecules, including the one or more sample quality biomarkers and the small molecules from metabolic profiling or biochemical analysis, measured in the biological sample obtained from the subject, and
   a processor device in communication with the database, the processor device being configured to compare the levels of the one or more sample quality biomarkers in the sample to sample quality reference levels of the one or more sample quality biomarkers to identify one or more aberrant sample quality biomarkers to assess sample quality,
   wherein the sample quality assessment is used to identify and provide a list of affected sample quality parameters, identify at least one intended use associated with the one or more aberrant sample quality biomarkers, and/or provide a list of recommended approaches for evaluating the sample, and
   wherein the sample quality analysis is performed concomitantly with metabolic profiling or biochemical analysis of the same sample.

2. The system of claim 1, wherein the one or more sample quality biomarkers are selected from the group consisting of 1-(1-enyl-palmitoyl)-2-arachidonoyl-GPE (P-16:0/20:4), 1-(1-enyl-palmitoyl)-2-docosahexaenoyl-GPE (P-16:0/22:6), 1-(1-enyl-palmitoyl)-GPE (P-16:0), 1-(1-enyl-stearoyl)-2-arachidonoyl-GPE (P-18:0/20:4), 1,3-7-trimethylurate, 1,3-dihydroxyacetone, 1,5-anhydroglucitol (1,5-AG), 10-heptadecenoate (17:1n7), 10-nonadecenoate (19:1n9), 12,13-DiHOME, 12-HETE, 13-HODE +9-HODE, 15-methylpalmitate, 16a-hydroxy DHEA 3-sulfate, 17,18-DiHETE, 17-methylstearate, 1-arachidonoylglyercophosphate, 1-arachidonoyl-GPC (20:4n6), 1-dihomo-linolenoyl-GPC (20:3n3 or 6), 1-docosahexaenoyl-GPC (22:6), 1-linoleoylglycerol (18:2), 1-linoleoyl-GPC (18:2), 1-margaroyl-GPC (17:0), 1-methylguanosine, 1-myristoyl-GPC (14:0), 1-octadecanol, 1-oleoyl-2-docosahexaenoyl-GPC (18:1/22:6), 1-oleoyl-2-linoleoyl-GPE (18:1/18:2), 1-oleoylglycerol (18:1), 1-oleoyl-GPC (18:1), 1-oleoyl-GPI (18:1), 1-palmitoleoyl-GPC (16:1), 1-palmitoyl-2-docosahexaenoyl-GPC (16:0/22:6), 1-palmitoyl-2-linoleoyl-GPE (16:0/18:2), 1-palmitoylglycerol (16:0), 1-palmitoylglycerophosphate, 1-palmitoyl-GPC (16:0), 1-palmityl-2-arachidonoyl-GPC (O-16:0/20:4), 1-pentadecanoylglycerophosphocholine (15:0), 1-stearoyl-2-linoleoyl-GPE (18:0/18:2), 1-stearoyl-2-oleoyl-GPE (18:0/18:1), 1-stearoylglycerophosphoserine, 1-stearoyl-GPC (18:0), 1-stearoyl-GPI (18:0), 2-aminoadipate, 2-aminobutyrate, 2-arachidonoyl-GPC (20:4), 2-arachidonoyl-GPE (20:4), 2'-deoxycytidine, 2'-deoxyguanosine, 2'-deoxyinosine, 2'-deoxyuridine, 2-docosahexaenoyl-GPC (22:6), 2-docosahexaenoyl-GPE (22:6), 2-docosapentaenoyl-GPE (22:5), 2-hydroxy-3-methylvalerate, 2-hydroxybutyrate (AHB), 2-hydroxyglutarate, 2-linoleoyl-GPC (18:2), 2-linoleoyl-GPE (18:2), 2-methylcitrate, 2-oleoyl-GPC (18:1), 2-palmitoleoyl-GPC (16:1), 2-palmitoyl-GPC (16:0), 2-phosphoglycerate, 2-stearoyl-GPC (18:0), 2-stearoyl-GPI (18:0), 3-(3-hydroxyphenyl)propionate, 3-(4-hydroxyphenyl)lactate (HPLA), 3-hydroxy-2-ethylpropionate, 3-hydroxy-3-methylglutarate, 3-hydroxybutyrate (BHBA), 3-hydroxypropanoate, 3-indoxyl sulfate, 3-methyl-2-oxobutyrate, 3-methyl-2-oxovalerate, 3-methyladipate, 3-methyl-catechol-sulfate, 3-methylcrotonylglycine, 3-methylglutarylcarnitine (C6), 3-phosphoglycerate, 4-guanidinobutanoate, 4-hydroxyphenylacetate, 4-hydroxyphenylpyruvate, 4-methyl-2-oxopentanoate, 4-phenylbutyrate, 4-vinylguaiacol-sulfate, 5,6-dihydrothymine, 5,6-dihydrouracil, 5-aminovalerate, 5-dodecenoate (12:1n7), 5-hydroxyhexanoate, 5-KETE, 5-ketogluconate, 5-methyluridine (ribothymidine), 5-oxoproline, 6-beta-hydroxylithocholate, 6-hosphogluconate, 9,10-DiHOME, acetylcarnitine, acetylphosphate, adenosine, adenosine 3'-monophosphate (3'-AMP), adenosine monophosphate (AMP), adipate, alanine, alanylleucine, alanyltyrosine, allothreonine, alpha-hydroxyisocaproate, alpha-hydroxyisovalerate, alpha-ketobutyrate, alpha-ketoglutarate, arabitol, arabonate, arachidonate (20:4n6), arginine, argininosuccinate, ascorbate (Vitamin C), asparagine, asparagylleucine, aspartate, aspartylleucine, azelate, azelate (nonanedioate), benzoate, beta-alanine, beta-hydroxyisovaleroylcarnitine, beta-hydroxypyruvate, betaine, beta-muricholate, bilirubin (E,E), bilirubin (Z,Z), biliverdin, biopterin, butyrylcarnitine, caffeine, caprate (6:0), caproate (6:0), caprylate (8:0), catechol sulfate, C-glycosyltryptophan, chenodeoxycholate, choline, cinnamoylglycine, cis-4-decenoyl-carnitine, cis-vaccenate (18:1n7), citraconate/glutaconate, citrate, citrulline, cortisone, creatine, cys-gly, oxidized, cysteine sulfinic acid, cysteine-glutathione disulfide, Cysteinylglycine, cytidine, cytidine 5'-monophosphate (5'-CMP), daidzein, decanoylcarnitine (C10), dehydroascorbate, deoxycarnitine, dihomo-linoleate (20:2n6), dihomo-linolenate (20:3n3 or n6), dimethylarginine (SDMA+ADMA), docosadienoate (22:2n6), docosahexaenoate (DHA; 22:6n3), docosapentaenoate (n6 DPA; 22:5n6), docosatrienoate (22:3n3), dopamine sulfate, eicosapentaenoate (EPA; 20:5n3), eicosenoate (20:1), equol sulfate, ergothioneine, erythronate, ethanolamine, flavin adenine dinucleotide (FAD), flavin mononucleotide (FMN), fructose, fumarate, gamma-aminobutyrate (GABA), gamma-glutamylalanine, gamma-glutamylglutamate, gamma-glutamylglutamine, gamma-glutamylglycine, gamma-glutamylhistidine, gamma-glutamylleucine, gamma-glutamylmethionine, gamma-glutamylphenylalanine, gamma-glutamylthreonine, gamma-glutamyltyrosine, gamma-glutamylvaline, gluconate, glucose, glucose 6-phosphate, glucuronate, glutamate, glutamine, glutathione, oxidized (GSSG), glutathione, reduced (GSH), glycerate, glycerol, glycerophosphoethanolamine, glycerophosphorylcholine (GPC), glycine, glycochenodeoxycholate, glycochenodeoxycholate-sulfate, glycocholate, glycodeoxycholate, glycodeoxycholate-sulfate, glycohyocholate, glycolate (hydroxyacetate), glycolithocholate, glycoursodeoxycholate, glycylleucine, glycylproline, glycylvaline, guanosine, gulono-1,4-lactone, hexadecanedioate, hexanoylcarnitine (C6), hexanoylglycine, hippurate, histidine, histidylalanine, homoserine, homostachydrine, HWESASLLR, HWESASXX, hydantoin-5-propionic acid, hypoxanthine, indole-3-carboxylic acid, inosine, inositol 1-phosphate (I1P), Isobar: betaine aldehyde, N-methyldiethanolamine, Isobar: fructose 1,6-diphosphate, glucose 1,6-diphosphate, myo-inositol 1,4 or 1,3-diphosphate, isobutyrylcarnitine, isoleucine, isoleucylglycine, isoleucylvaline, isopalmitic acid, isovalerate (C5), isovalerylcarnitine, isovalerylglycine, kojibiose, kynurenate, kynurenine, lactate, laurate (12:0), laurylcarnitine (C12), leucine, leucylalanine, leucylleucine, linoleate (18:2n6), linolenate [alpha or gamma] (18:3n3 or 6), linoleoylcarnitine, lysine, malate, maleate, maltopentaose, maltose, maltotetraose, maltotriose, mannose, margarate (17:0), methionine, methionine sulfoxide, methionylalanine, methylsuccinate, myo-inositol, myristate (14:0), myristoleate (14:1n5), myristoleoylcarnitine, myristoylcarnitine, N(2)-furoyl-glycine, N1-methyladenosine, N2,N2-dimethylguanosine, N6-acetyllysine, N6-carbamoylthreonyladenosine, N6-methyladenosine, N-acetylalanine, N-acetylaspartate (NAA), N-acetyl-beta-alanine, N-acetylglutamate, N-acetylglycine, N-acetylleucine, N-acetylmethionine, N-formylmethionine, N-glycolylneuraminate, nicotinamide, nicotinamide adenine dinucleotide (NAD+), nonadecanoate (19:0), o-cresol-sulfate, octanoylcarnitine, oleate (18:1n9), oleate-vaccenate (18:1), oleic ethanolamide, Oleoyl ethanolamide, oleoylcarnitine (C18), oleoyl-ethanolamide, O-methylcatechol-sulfate, ophthalmate, ornithine, orotate, oxalate (ethanedioate), palmitate (16:0), palmitoleate, palmitoleate (16:1n7), palmitoyl ethanolamide, palmitoyl sphingomyelin (d18:1/16:0), palmitoylcarnitine (C16), palmitoyl-ethanolamide, pantothenate, pelargonate (9:0), pentadecanoate (15:0), phenylacetate, phenylacetylglycine, phenylalanine, phenylalanyllysine, phenylalanyltryptophan, phenyllactate (PLA), phenylpropionylglycine, phenylpyruvate, phosphoenolpyruvate (PEP), phosphoethanolamine, pipecolate, prolylglycine, prolylleucine, propionylcarnitine, pseudouridine, pyridoxate, pyrraline, pyruvate, quinate, ribitol, riboflavin (Vitamin B2), ribose, ribose 5-phosphate, ribulose, S-adenosylhomocysteine (SAH), sarcosine (N-Methylglycine), sebacate (decanedioate), serylleucine, serylphenylalanine, seryltyrosine, S-methylglutathione, sorbitol, spermidine, spermine, sphinganine, Sphinganine-1-phosphate, sphingosine, sphingosine 1-phosphate, stachydrine, stearate (18:0), stearidonate (18:4n3), stearoylcarnitine (C18), stearoylethanolamide, suberylglycine, succinate, succinimide, succinylcarnitine, tagatose, tartronate (hydroxymalonate), taurine, tauro-beta-muricholate, taurochenodeoxycholate, taurocholate, taurodeoxycholate, tauroursodeoxycholate, tetradecanedioate, threonine, thymine, tiglylcarnitine, trans-4-hydroxyproline, trigonelline (N'-methylnicotinate), tryptophan, undecanedioate, uracil, urate, urea, uridine, valerylglycine, valine, valylglycine, valylvaline, xanthine, xylonate and the sample quality biomarkers cysteinylglycine, sphinganine-1-phosphate, and combinations thereof.

3. The system of claim 1, wherein the processor device is further configured to assess and compare the level(s) of the one or more sample quality biomarkers using statistical analysis to identify the one or more aberrant sample quality biomarkers in said sample, list the one or more aberrant sample quality biomarkers, and provide a sample quality assessment.

4. The system of claim 3, wherein the system provides a sample quality assessment score wherein the score is a composite score for the sample as a whole or a Quality Parameter Score (QPS) for one or more sample quality parameters.

5. The system of claim 3, wherein the system associates the one or more aberrant sample quality biomarkers with sample quality parameters, and provides a list of affected sample quality parameters.

6. The system of claim 1, wherein the sample quality assessment provides one or more of the following recommendations:
application of a correction factor to one or more small molecules before using the one or more small molecules in a further assessment,
elimination of certain small molecules or biochemical pathways from the metabolic profiling or biochemical analysis,
substitution of certain small molecules or biochemical pathways with a different small molecules or biochemical pathway to use in the metabolic profiling or biochemical analysis, and
rejection of the sample for metabolic profiling or biochemical analysis.

7. A method of determining whether metabolic profiling or biochemical analysis result obtained for a biological sample is acceptable to be used, the method comprising:
analyzing a biological sample obtained from a subject by measuring levels of at least 25 small molecules to generate a small molecule profile, wherein the measured small molecules include one or more sample quality biomarkers and one or more intended use small molecules,
analyzing the biological sample obtained from the subject for metabolic profiling or biochemical analysis, wherein the sample quality analysis is performed concomitantly with metabolic profiling or biochemical analysis of the same sample, and
assessing the quality of the biological sample using the one or more biomarkers of sample quality to determine whether the sample meets acceptance criteria for metabolic profiling or biochemical analysis,
for a sample that is determined to meet acceptance criteria for metabolic profiling or biochemical analysis, using the result of the metabolic profiling or biochemical analysis and for a sample that is determined to not meet acceptance criteria for metabolic profiling or biochemical analysis, not using the result of the metabolic profiling or biochemical analysis or modifying the result of the metabolic profiling or biochemical analysis based on the quality assessment analysis.

8. The method of claim 7, wherein the one or more sample quality biomarkers are selected from the group consisting of 1-(1-enyl-palmitoyl)-2-arachidonoyl-GPE (P-16:0/20:4), 1-(1-enyl-palmitoyl)-2-docosahexaenoyl-GPE (P-16:0/22:6), 1-(1-enyl-palmitoyl)-GPE (P-16:0), 1-(1-enyl-stearoyl)-2-arachidonoyl-GPE (P-18:0/20:4), 1,3-7-trimethylurate, 1,3-dihydroxyacetone, 1,5-anhydroglucitol (1,5-AG), 10-heptadecenoate (17:1n7), 10-nonadecenoate (19:1n9), 12,13-DiHOME, 12-HETE, 13-HODE+9-HODE, 15-methylpalmitate, 16a-hydroxy DHEA 3-sulfate, 17,18-DiHETE, 17-methylstearate, 1-arachidonoylglyercophosphate, 1-arachidonoyl-GPC (20:4n6), 1-dihomo-linolenoyl-GPC (20:3n3 or 6), 1-docosahexaenoyl-GPC (22:6), 1-linoleoylglycerol (18:2), 1-linoleoyl-GPC (18:2), 1-margaroyl-GPC (17:0), 1-methylguanosine, 1-myristoyl-GPC (14:0), 1-octadecanol, 1-oleoyl-2-docosahexaenoyl-GPC (18:1/22:6), 1-oleoyl-2-linoleoyl-GPE (18:1/18:2), 1-oleoylglycerol (18:1), 1-oleoyl-GPC (18:1), 1-oleoyl-GPI (18:1), 1-palmitoleoyl-GPC (16:1), 1-palmitoyl-2-docosahexaenoyl-GPC (16:0/22:6), 1-palmitoyl-2-linoleoyl-GPE (16:0/18:2), 1-palmitoylglycerol (16:0), 1-palmitoylglycerophosphate, 1-palmitoyl-GPC (16:0), 1-palmityl-2-arachidonoyl-GPC (O-16:0/20:4), 1-pentadecanoylglycerophosphocholine (15:0), 1-stearoyl-2-linoleoyl-GPE (18:0/18:2), 1-stearoyl-2-oleoyl-GPE (18:0/18:1), 1-stearoylglycerophosphoserine, 1-stearoyl-GPC (18:0), 1-stearoyl-GPI (18:0), 2-aminoadipate, 2-aminobutyrate, 2-arachidonoyl-GPC (20:4), 2-arachidonoyl-GPE (20:4), 2'-deoxycytidine, 2'-deoxyguanosine, 2'-deoxyinosine, 2'-deoxyuridine, 2-docosahexaenoyl-GPC (22:6), 2-docosahexaenoyl-GPE (22:6), 2-docosapentaenoyl-GPE (22:5), 2-hydroxy-3-methylvalerate, 2-hydroxybutyrate (AHB), 2-hydroxyglutarate, 2-linoleoyl-GPC (18:2), 2-linoleoyl-GPE (18:2), 2-methylcitrate, 2-oleoyl-GPC (18:1), 2-palmitoleoyl-GPC (16:1), 2-palmitoyl-GPC (16:0), 2-phosphoglycerate, 2-stearoyl-GPC (18:0), 2-stearoyl-GPI (18:0), 3-(3-hydroxyphenyl)propionate, 3-(4-hydroxyphenyl)lactate (HPLA), 3-hydroxy-2-ethylpropionate, 3-hydroxy-3-methylglutarate, 3-hydroxybutyrate (BHBA), 3-hydroxypropanoate, 3-indoxyl sulfate, 3-methyl-2-oxobutyrate, 3-methyl-2-oxovalerate, 3-methyladipate, 3-methyl-catechol-sulfate, 3-methylcrotonylglycine, 3-methylglutarylcarnitine (C6), 3-phosphoglycerate, 4-guanidinobutanoate, 4-hydroxyphenylacetate, 4-hydroxyphenylpyruvate, 4-methyl-2-oxopentanoate, 4-phenylbutyrate, 4-vinylguaiacol-sulfate, 5,6-dihydrothymine, 5,6-dihydrouracil, 5-aminovalerate, 5-dodecenoate (12:1n7), 5-hydroxyhexanoate, 5-KETE, 5-ketogluconate, 5-methyluridine (ribothymidine), 5-oxoproline, 6-beta-hydroxylithocholate, 6-phosphogluconate, 9,10-DiHOME, acetylcarnitine, acetylphosphate, adenosine, adenosine 3'-monophosphate (3'-AMP), adenosine monophosphate (AMP), adipate, alanine, alanylleucine, alanyltyrosine, allo-threonine, alpha-hydroxyisocaproate, alpha-hydroxyisovalerate, alpha-ketobutyrate, alpha-ketoglutarate, arabitol, arabonate, arachidonate (20:4n6), arginine, argininosuccinate, ascorbate (Vitamin C), asparagine, asparagylleucine, aspartate, aspartylleucine, azelate, azelate (nonanedioate), benzoate, beta-alanine, beta-hydroxyisovaleroylcarnitine, beta-hydroxypyruvate, betaine, beta-muricholate, bilirubin (E,E), bilirubin (Z,Z), biliverdin, biopterin, butyrylcarnitine, caffeine, caprate (6:0), caproate (6:0), caprylate (8:0), catechol sulfate, C-glycosyltryptophan, chenodeoxycholate, choline, cinnamoylglycine, cis-4-decenoyl-carnitine, cis-vaccenate (18:1n7), citraconate/glutaconate, citrate, citrulline, cortisone, creatine, cys-gly, oxidized, cysteine sulfinic acid, cysteine-glutathione disulfide, Cysteinylglycine, cytidine, cytidine 5'-monophosphate (5'-CMP), daidzein, decanoylcarnitine (C10), dehydroascorbate, deoxycarnitine, dihomo-linoleate (20:2n6), dihomo-linolenate (20:3n3 or n6), dimethylarginine (SDMA+ADMA), docosadienoate (22:2n6), docosahexaenoate (DHA; 22:6n3), docosapentaenoate (n6 DPA; 22:5n6), docosatrienoate (22:3n3), dopamine sulfate, eicosapentaenoate (EPA; 20:5n3), eicosenoate (20:1), equol sulfate, ergothioneine, erythronate, ethanolamine, flavin adenine dinucleotide (FAD), flavin mononucleotide (FMN), fructose, fumarate, gamma-aminobutyrate (GABA), gamma-glutamylalanine, gamma-glutamylglutamate, gamma-glutamylglutamine, gamma-glutamylglycine, gamma-glutamylhistidine, gamma-glutamylleucine, gamma-glutamylmethionine, gamma-glutamylphenylalanine, gamma-glutamylthreonine, gamma-glutamyltyrosine, gamma-glutamylvaline, gluconate, glucose, glucose 6-phosphate, glucuronate, glutamate, glutamine, glutathione, oxidized (GSSG), glutathione, reduced (GSH), glycerate, glycerol, glycerophosphoethanolamine, glycerophosphorylcholine (GPC), glycine, glycochenodeoxycholate, glycochenodeoxycholate-sulfate, glycocholate, glycodeoxycholate, glycodeoxycholate-sulfate, glycohyocholate, glycolate (hydroxyacetate), glycolithocholate, glycoursodeoxycholate, glycylleucine, glycylproline, glycylvaline, guanosine, gulono-1,4-lactone, hexadecanedioate, hexanoylcarnitine (C6), hexanoylglycine, hippurate, histidine, histidylalanine, homoserine, homostachydrine, HWESASLLR, HWESASXX, hydantoin-5-propionic acid, hypoxanthine, indole-3-carboxylic acid, inosine, inositol 1-phosphate (I1P), Isobar: betaine aldehyde, N-methyldiethanolamine, Isobar: fructose 1,6-diphosphate, glucose 1,6-diphosphate, myo-inositol 1,4 or 1,3-diphosphate, isobutyrylcarnitine, isoleucine, isoleucylglycine, isoleucylvaline, isopalmitic acid, isovalerate (C5), isovalerylcarnitine, isovalerylglycine, kojibiose, kynurenate, kynurenine, lactate, laurate (12:0), laurylcarnitine (C12), leucine, leucylalanine, leucylleucine, linoleate (18:2n6), linolenate [alpha or gamma] (18:3n3 or 6), linoleoylcarnitine, lysine, malate, maleate, maltopentaose, maltose, maltotetraose, maltotriose, mannose, margarate (17:0), methionine, methionine sulfoxide, methionylalanine, methylsuccinate, myo-inositol, myristate (14:0), myristoleate (14:1n5), myristoleoylcarnitine, myristoylcarnitine, N(2)-furoyl-glycine, N1-methyladenosine, N2,N2-dimethylguanosine, N6-acetyllysine, N6-carbamoylthreonyladenosine, N6-methyladenosine, N-acetylalanine, N-acetylaspartate (NAA), N-acetyl-beta-alanine, N-acetylglutamate, N-acetylglycine, N-acetylleucine, N-acetylmethionine, N-formylmethionine, N-glycolylneuraminate, nicotinamide, nicotinamide adenine dinucleotide (NAD+), nonadecanoate (19:0), o-cresol-sulfate, octanoylcarnitine, oleate (18:1n9), oleate-vaccenate (18:1), oleic ethanolamide, Oleoyl ethanolamide, oleoylcarnitine (C18), oleoyl-ethanolamide, O-methylcatechol-sulfate, ophthalmate, ornithine, orotate, oxalate (ethanedioate), palmitate (16:0), palmitoleate, palmitoleate (16:1n7), palmitoyl ethanolamide, palmitoyl sphingomyelin (d18:1/16:0), palmitoylcarnitine (C16), palmitoyl-ethanolamide, pantothenate, pelargonate (9:0), pentadecanoate (15:0), phenylacetate, phenylacetylglycine, phenylalanine, phenylalanyllysine, phenylalanyltryptophan, phenyllactate (PLA), phenylpropionylglycine, phenylpyruvate, phosphoenolpyruvate (PEP), phosphoethanolamine, pipecolate, prolylglycine, prolylleucine, propionylcarnitine, pseudouridine, pyridoxate, pyrraline, pyruvate, quinate, ribitol, riboflavin (Vitamin B2), ribose, ribose 5-phosphate, ribulose, S-adenosylhomocysteine (SAH), sarcosine (N-Methylglycine), sebacate (decanedioate), serylleucine, serylphenylalanine, seryltyrosine, S-methylglutathione, sorbitol, spermidine, spermine, sphinganine, Sphinganine-1-phosphate, sphingosine, sphingosine 1-phosphate, stachydrine, stearate (18:0), stearidonate (18:4n3), stearoylcarnitine (C18), stearoylethanolamide, suberylglycine, succinate, succinimide, succinylcarnitine, tagatose, tartronate (hydroxymalonate), taurine, tauro-beta-muricholate, taurochenodeoxycholate, taurocholate, taurodeoxycholate, tauroursodeoxycholate, tetradecanedioate, threonine, thymine, tiglylcarnitine, trans-4-hydroxyproline, trigonelline (N'-methylnicotinate), tryptophan, undecanedioate, uracil, urate, urea, uridine, valerylglycine, valine, valylglycine, valylvaline, xanthine, xylonate and from the biomarkers cysteinylglycine, sphinganine-1-phosphate and combinations thereof.

9. The method of claim 7, wherein the one or more sample quality biomarkers selected from the group consisting of adenosine monophosphate (AMP), 1-(1-enyl-palmitoyl)-2-arachidonoyl-GPE (P-16:0/20:4), 1-(1-enyl-palmitoyl)-2-docosahexaenoyl-GPE (P-16:0/22:6), 1-(1-enyl-stearoyl)-2-arachidonoyl-GPE (P-18:0/20:4), 1,5-anhydroglucitol (1,5-AG), 12-HETE, 13-HODE+9-HODE, 16a-hydroxy DHEA 3-sulfate, 1-arachidonoylglyercophosphate, 1-linoleoylglycerol (18:2), 1-methylguanosine, 1-oleoyl-2-docosahexaenoyl-GPC (18:1/22:6), 1-oleoylglycerol (18:1), 1-palmitoyl-2-docosahexaenoyl-GPC (16:0/22:6), 1-palmitoylglycerol (16:0), 1-palmitoylglycerophosphate, 1-palmitoyl-GPC (16:0), 1-palmityl-2-arachidonoyl-GPC (O-16:0/20:4), 1-pentadecanoylglycerophosphocholine (15:0), 1-stearoylglycerophosphoserine, 2'-deoxyguanosine, 2'-deoxyinosine, 2'-deoxyuridine, 2-hydroxy-3-methylvalerate, 2-hydroxyglutarate, 2-methylcitrate, 3-(3-hydroxyphenyl)propionate, 3-(4-hydroxyphenyl)lactate (HPLA), 3-hydroxy-2-ethylpropionate, 3-hydroxypropanoate, 3-methyl-2-oxobutyrate, 3-methyl-2-oxovalerate, 3-methyladipate, 4-guanidinobutanoate, 4-hydroxyphenylacetate, 4-methyl-2-oxopentanoate, 4-phenylbutyrate, 5,6-dihydrouracil, 5-hydroxyhexanoate, 5-KETE, 5-oxoproline, acetylcarnitine, acetylcarnitine (C2), adenosine, adipate, alpha-hydroxyisocaproate, alpha-hydroxyisovalerate, alpha-ketobutyrate, alpha-ketoglutarate, arachidonate (20:4n6), arginine, argininosuccinate, asparagine, asparagylleucine, benzoate, bilirubin (E,E), bilirubin (Z,Z), biliverdin, caprate (6:0), caproate (6:0), choline, cys-gly, oxidized, cysteine sulfinic acid, cysteine-glutathione disulfide, decanoylcarnitine (C10), docosahexaenoate (DHA; 22:6n3), docosapentaenoate (n6 DPA; 22:5n6), eicosapentaenoate (EPA; 20:5n3), fumarate, gamma-glutamylalanine, gamma-glutamylglutamine, gamma-glutamylglycine, gamma-glutamylhistidine, gamma-glutamylleucine, gamma-glutamylmethionine, gamma-glutamylphenylalanine, gamma-glutamylthreonine, gamma-glutamyltyrosine, gamma-glutamylvaline, glucose, glutamate, glutamine, glutathione, oxidized (GSSG), glycerophosphoethanolamine, glycerophosphorylcholine (GPC), glycylproline, hexanoylcarnitine (C6), histidylalanine, HWESASLLR, HWESASXX, hypoxanthine, inosine, isoleucine, isoleucylvaline, isovalerate, isovalerate (C5), lactate, laurylcarnitine (C12), leucylalanine, leucylleucine, linoleoylcarnitine, malate, maltose, mannose, methionine, methionylalanine, methylsuccinate, myristoleate (14:1n5), myristoylcarnitine, N6-methyladenosine, N-acetylaspartate (NAA), N-acetylleucine, N-acetylmethionine, N-formylmethionine, oleic ethanolamide, oleoylcarnitine (C18), ornithine, oxalate (ethanedioate), palmitoyl ethanolamide, palmitoylcarnitine, palmitoylcarnitine (C16), phenylacetate, phenylalanyllysine, phenylalanyltryptophan, phenyllactate (PLA), phenylpyruvate, prolylglycine, propionylcarnitine, pyruvate, S-adenosylhomocysteine (SAH), sebacate (decanedioate), seryltyrosine, spermine, sphinganine, sphingosine, sphingosine 1-phosphate, stearoylcarnitine, stearoylcarnitine (C18), succinate, succinimide, tartronate (hydroxymalonate), taurine, thymine, uracil, urate, uridine, valylglycine, valylvaline, and xanthine provide an indication of at least one sample processing condition for the sample.

10. The method of claim 9, wherein the at least one sample processing condition is selected from one or more of the group consisting of time incubated as whole blood prior to separation, time of cold incubation prior to freezing, time of room temperature incubation prior to freezing, sample storage temperature, sample storage time, and number of freeze/thaw cycles.

11. The method of claim 7, wherein the one or more sample quality biomarkers selected from the group consisting of 1-(1-enyl-palmitoyl)-GPE (P-16:0), 1,3-7-trimethylurate, 1,3-dihydroxyacetone, 1,5-anhydroglucitol (1,5-AG), 10-heptadecenoate (17:1n7), 10-nonadecenoate (19:1n9), 12,13-DiHOME, 13-HODE+9-HODE, 15-methylpalmitate, 17,18-DiHETE, 17-methylstearate, 1-arachidonoyl-GPC (20:4n6), 1-dihomo-linolenoyl-GPC (20:3n3 or 6), 1-docosahexaenoyl-GPC (22:6), 1-linoleoyl-GPC (18:2), 1-margaroyl-GPC (17:0), 1-myristoyl-GPC (14:0), 1-octadecanol, 1-oleoyl-2-linoleoyl-GPE (18:1/18:2), 1-oleoyl-GPC (18:1), 1-oleoyl-GPI (18:1), 1-palmitoleoyl-GPC (16:1), 1-palmitoyl-2-linoleoyl-GPE (16:0/18:2), 1-palmitoyl-GPC (16:0), 1-stearoyl-2-linoleoyl-GPE (18:0/18:2), 1-stearoyl-2-oleoyl-GPE (18:0/18:1), 1-stearoyl-GPC (18:0), 1-stearoyl-GPI (18:0), 2-aminoadipate, 2-aminobutyrate, 2-arachidonoyl-GPC (20:4), 2-arachidonoyl-GPE (20:4), 2'-deoxycytidine, 2-docosahexaenoyl-GPC (22:6), 2-docosahexaenoyl-GPE (22:6), 2-docosapentaenoyl-GPE (22:5), 2-hydroxybutyrate (AHB), 2-hydroxyglutarate, 2-linoleoyl-GPC (18:2), 2-linoleoyl-GPE (18:2), 2-oleoyl-GPC (18:1), 2-palmitoleoyl-GPC (16:1), 2-palmitoyl-GPC (16:0), 2-phosphoglycerate, 2-stearoyl-GPC (18:0), 2-stearoyl-GPI (18:0), 3-(4-hydroxyphenyl)lactate, 3-hydroxy-3-methylglutarate, 3-hydroxybutyrate (BHBA), 3-indoxyl sulfate, 3-methyl-catechol-sulfate, 3-methylcrotonylglycine, 3-methylglutarylcarnitine (C6), 3-phosphoglycerate, 4-guanidinobutanoate, 4-hydroxyphenylpyruvate, 4-vinylguaiacol-sulfate, 5,6-dihydrothymine, 5-aminovalerate, 5-dodecenoate (12:1n7), 5-ketogluconate, 5-methyluridine (ribothymidine), 5-oxoproline, 6-beta-hydroxylithocholate, 6-phosphogluconate, 9,10-DiHOME, acetylcarnitine, acetylphosphate, adenosine 3'-monophosphate (3'-AMP), adipate, alanine, alanylleucine, alanyltyrosine, allo-threonine, alpha-hydroxyisovalerate, arabitol, arabonate, ascorbate (Vitamin C), aspartate, aspartylleucine, azelate, azelate (nonanedioate), azelate (nonanedioate), beta-alanine, beta-hydroxyisovaleroylcarnitine, beta-hydroxypyruvate, betaine, beta-muricholate, bilirubin-E-E-, biopterin, butyrylcarnitine, caffeine, caproate (6:0), caprylate (8:0), catechol sulfate, catechol-sulfate, C-glycosyltryptophan, chenodeoxycholate, choline, cinnamoylglycine, cis-4-decenoyl-carnitine, cis-vaccenate (18:1n7), citraconate/glutaconate, citrate, citrulline, cortisone, creatine, cys-gly, oxidized, cysteine-glutathione disulfide, cytidine, cytidine 5'-monophosphate (5'-CMP), daidzein, decanoylcarnitine, dehydroascorbate, deoxycarnitine, dihomo-linoleate (20:2n6), dihomo-linolenate (20:3n3 or n6), dimethylarginine (SDMA+ADMA), docosadienoate (22:2n6), docosahexaenoate (DHA; 22:6n3), docosatrienoate (22:3n3), dopamine sulfate, eicosapentaenoate (EPA; 20:5n3), eicosenoate (20:1), equol sulfate, ergothioneine, erythronate, ethanolamine, flavin adenine dinucleotide (FAD), flavin mononucleotide (FMN), fructose, fumarate, gamma-aminobutyrate (GABA), gamma-glutamylalanine, gamma-glutamylglutamate, gamma-glutamylleucine, gamma-glutamylthreonine, gluconate, glucose, glucose 6-phosphate, glucuronate, glutamate, glutamine, glutathione, oxidized (GSSG), glutathione, reduced (GSH), glycerate, glycine, glycochenodeoxycholate, glycochenodeoxycholate-sulfate, glycocholate, glycodeoxycholate, glycodeoxycholate-sulfate, glycohyocholate, glycolate (hydroxyacetate), glycolithocholate, glycoursodeoxycholate, glycylleucine, glycylproline, glycylvaline, guanosine, gulono-1,4-lactone, hexadecanedioate, hexanoylcarnitine, hexanoylglycine, hippurate, histidine, homoserine, homostachydrine, hydantoin-5-propionic acid, hypoxanthine, indole-3-carboxylic acid, inosine, inositol 1-phosphate (I1P), Isobar: betaine aldehyde, N-methyldiethanolamine, Isobar: fructose 1,6-diphosphate, glucose 1,6-diphosphate, myo-inositol 1,4 or 1,3-diphosphate, isobutyrylcarnitine, isoleucine, isoleucylglycine, isopalmitic acid, isovalerylcarnitine, isovalerylglycine, kojibiose, kynurenate, kynurenine, lactate, laurate (12:0), laurylcarnitine, leucine, linoleate (18:2n6), linolenate [alpha or gamma; (18:3n3 or 6)], linoleoylcarnitine, malate, maleate, maltopentaose, maltose, maltotetraose, maltotriose, mannose, margarate (17:0), methionine sulfoxide, methylsuccinate, myo-inositol, myristate (14:0), myristoleate (14:1n5), myristoleoylcarnitine, N(2)-furoyl-glycine, N1-methyladenosine, N2,N2-dimethylguanosine, N6-acetyllysine, N6-carbamoylthreonyladenosine, N-acetylalanine, N-acetyl-beta-alanine, N-acetylglutamate, N-acetylglycine, N-glycolylneuraminate, nicotinamide, nicotinamide adenine dinucleotide (NAD+), nonadecanoate (19:0), o-cresol-sulfate, octanoylcarnitine, oleate (18:1n9), oleate-vaccenate (18:1), oleoylcarnitine, oleoyl-ethanolamide, O-methylcatechol-sulfate, ophthalmate, ornithine, orotate, palmitate (16:0), palmitoleate (16:1n7), palmitoyl sphingomyelin (d18:1/16:0), palmitoylcarnitine, palmitoyl-ethanolamide, pantothenate, pelargonate (9:0), pentadecanoate (15:0), phenylacetylglycine, phenylalanine, phenylpropionylglycine, phosphoenolpyruvate (PEP), phosphoethanolamine, pipecolate, prolylglycine, prolylleucine, propionylcarnitine, pseudouridine, pyridoxate, pyrraline, quinate, ribitol, riboflavin (Vitamin B2), ribose, ribose 5-phosphate, ribulose, sarcosine (N-Methylglycine), serylleucine, serylphenylalanine, S-methylglutathione, sorbitol, spermidine, stachydrine, stearate (18:0), stearidonate (18:4n3), stearoyl-ethanolamide, suberylglycine, succinate, succinylcarnitine, tagatose, tauro-beta-muricholate, taurochenodeoxycholate, taurocholate, taurodeoxycholate, tauroursodeoxycholate, tetradecanedioate, threonine, tiglylcarnitine, trans-4-hydroxyproline, trigonelline (N'-methylnicotinate), tryptophan, undecanedioate, uracil, urea, uridine, valerylglycine, valine, xanthine, and xylonate provide an indication of the fasting status of the subject.

12. The method of claim 7, wherein the sample quality assessment is used to identify and provide a list of affected sample quality parameters, identify at least one intended use associated with one or more affected parameters, identify at least one intended use associated with one or more aberrant sample quality biomarkers, and/or provide a list of recommended approaches for evaluating the results obtained from the sample.

13. The method of claim 7, wherein the sample quality assessment provides a recommendation for the application of a correction factor to one or more small molecules before using the measured results obtained from the one or more small molecules in a further assessment or for an intended use.

14. The method of claim 7, wherein the sample quality assessment provides a recommendation to eliminate the results obtained for certain of the one or more small molecules or biochemical pathways from the metabolic profiling or biochemical analysis.

15. The method of claim 7, wherein the sample quality assessment provides a recommendation to substitute the results obtained for one small molecule with the results obtained for a different small molecule for a certain biochemical pathway.

16. The method of claim 7, further comprising using the measured levels of the one or more sample quality biomarkers in a composite score.

17. The method of claim 7, wherein assessing the quality of the sample comprises surveying the sample for the level(s) of one or more sample quality biomarkers by statistical analysis to identify one or more aberrant sample quality biomarkers in said sample, listing one or more aberrant sample quality biomarkers, and providing a sample quality assessment.

18. The method of claim 17, further comprising associating the one or more aberrant sample quality biomarkers with sample quality parameters and providing a list of affected sample quality parameters.

19. A method of assessing the quality of a biological sample obtained from a subject to determine the suitability of the biological sample for metabolic profiling or biochemical analysis, the method comprising:

analyzing the biological sample to measure the level(s) of one or more sample quality biomarkers, wherein the one or more sample quality biomarkers are selected from the group consisting of 1-(1-enyl-palmitoyl)-2-arachidonoyl-GPE (P-16:0/20:4), 1-(1-enyl-palmitoyl)-2-docosahexaenoyl-GPE (P-16:0/22:6), 1-(1-enyl-palmitoyl)-GPE (P-16:0), 1-(1-enyl-stearoyl)-2-arachidonoyl-GPE (P-18:0/20:4), 1,3-7-trimethylurate, 1,3-dihydroxyacetone, 1,5-anhydroglucitol (1,5-AG), 10-heptadecenoate (17:1n7), 10-nonadecenoate (19:1n9), 12,13-DiHOME, 12-HETE, 13-HODE+9-HODE, 15-methylpalmitate, 16a-hydroxy DHEA 3-sulfate, 17,18-DiHETE, 17-methylstearate, 1-arachidonoylglyercophosphate, 1-arachidonoyl-GPC (20:4n6), 1-dihomo-linolenoyl-GPC (20:3n3 or 6), 1-docosahexaenoyl-GPC (22:6), 1-linoleoylglycerol (18:2), 1-linoleoyl-GPC (18:2), 1-margaroyl-GPC (17:0), 1-methylguanosine, 1-myristoyl-GPC (14:0), 1-octadecanol, 1-oleoyl-2-docosahexaenoyl-GPC (18:1/22:6), 1-oleoyl-2-linoleoyl-GPE (18:1/18:2), 1-oleoylglycerol (18:1), 1-oleoyl-GPC (18:1), 1-oleoyl-GPI (18:1), 1-palmitoleoyl-GPC (16:1), 1-palmitoyl-2-docosahexaenoyl-GPC (16:0/22:6), 1-palmitoyl-2-linoleoyl-GPE (16:0/18:2), 1-palmitoylglycerol (16:0), 1-palmitoylglycerophosphate, 1-palmitoyl-GPC (16:0), 1-palmitoyl-2-arachidonoyl-GPC (O-16:0/20:4), 1-pentadecanoylglycerophosphocholine (15:0), 1-stearoyl-2-linoleoyl-GPE (18:0/18:2), 1-stearoyl-2-oleoyl-GPE (18:0/18:1), 1-stearoylglycerophosphoserine, 1-stearoyl-GPC (18:0), 1-stearoyl-GPI (18:0), 2-aminoadipate, 2-aminobutyrate, 2-arachidonoyl-GPC (20:4), 2-arachidonoyl-GPE (20:4), 2'-deoxycytidine, 2'-deoxyguanosine, 2'-deoxyinosine, 2'-deoxyuridine, 2-docosahexaenoyl-GPC (22:6), 2-docosahexaenoyl-GPE (22:6), 2-docosapentaenoyl-GPE (22:5), 2-hydroxy-3-methylvalerate, 2-hydroxybutyrate (AHB), 2-hydroxyglutarate, 2-linoleoyl-GPC (18:2), 2-linoleoyl-GPE (18:2), 2-methylcitrate, 2-oleoyl-GPC (18:1), 2-palmitoleoyl-GPC (16:1), 2-palmitoyl-GPC (16:0), 2-phosphoglycerate, 2-stearoyl-GPC (18:0), 2-stearoyl-GPI (18:0), 3-(3-hydroxyphenyl)propionate, 3-(4-hydroxyphenyl)lactate (HPLA), 3-hydroxy-2-ethylpropionate, 3-hydroxy-3-methylglutarate, 3-hydroxybutyrate (BHBA), 3-hydroxypropanoate, 3-indoxyl sulfate, 3-methyl-2-oxobutyrate, 3-methyl-2-oxovalerate, 3-methyladipate, 3-methyl-catechol-sulfate, 3-methylcrotonylglycine, 3-methylglutarylcarnitine (C6), 3-phosphoglycerate, 4-guanidinobutanoate, 4-hydroxyphenylacetate, 4-hydroxyphenylpyruvate, 4-methyl-2-oxopentanoate, 4-phenylbutyrate, 4-vinylguaiacol-sulfate, 5,6-dihydrothymine, 5,6-dihydrouracil, 5-aminovalerate, 5-dodecenoate (12:1n7), 5-hydroxyhexanoate, 5-KETE, 5-ketogluconate, 5-methyluridine (ribothymidine), 5-oxoproline, 6-beta-hydroxylithocholate, 6-phosphogluconate, 9,10-DiHOME, acetylcarnitine, acetylphosphate, adenosine, adenosine 3'-monophosphate (3'-AMP), adenosine monophosphate (AMP), adipate, alanine, alanylleucine, alanyltyrosine, allo-threonine, alpha-hydroxyisocaproate, alpha-hydroxyisovalerate, alpha-ketobutyrate, alpha-ketoglutarate, arabitol, arabonate, arachidonate (20:4n6), arginine, argininosuccinate, ascorbate (Vitamin C), asparagine, asparagylleucine, aspartate, aspartylleucine, azelate, azelate (nonanedioate), benzoate, beta-alanine, beta-hydroxyisovaleroylcarnitine, beta-hydroxypyruvate, betaine, beta-muricholate, bilirubin (E,E), bilirubin (Z,Z), biliverdin, biopterin, butyrylcarnitine, caffeine, caprate (6:0), caproate (6:0), caprylate (8:0), catechol sulfate, C-glycosyltryptophan, chenodeoxycholate, choline, cinnamoylglycine, cis-4-decenoyl-carnitine, cis-vaccenate (18:1n7), citraconate/glutaconate, citrate, citrulline, cortisone, creatine, cys-gly, oxidized, cysteine sulfinic acid, cysteine-glutathione disulfide, Cysteinylglycine, cytidine, cytidine 5'-monophosphate (5'-CMP), daidzein, decanoylcarnitine (C10), dehydroascorbate, deoxycarnitine, dihomo-linoleate (20:2n6), dihomo-linolenate (20:3n3 or n6), dimethylarginine (SDMA+ADMA), docosadienoate (22:2n6), docosahexaenoate (DHA; 22:6n3), docosapentaenoate (n6 DPA; 22:5n6), docosatrienoate (22:3n3), dopamine sulfate, eicosapentaenoate (EPA; 20:5n3), eicosenoate (20:1), equol sulfate, ergothioneine, erythronate, ethanolamine, flavin adenine dinucleotide (FAD), flavin mononucleotide (FMN), fructose, fumarate, gamma-aminobutyrate (GABA), gamma-glutamylalanine, gamma-glutamylglutamate, gamma-glutamylglutamine, gamma-glutamylglycine, gamma-glutamylhistidine, gamma-glutamylleucine, gamma-glutamylmethionine, gamma-glutamylphenylalanine, gamma-glutamylthreonine, gamma-glutamyltyrosine, gamma-glutamylvaline, gluconate, glucose, glucose 6-phosphate, glucuronate, glutamate, glutamine, glutathione, oxidized (GSSG), glutathione, reduced (GSH), glycerate, glycerol, glycerophosphoethanolamine, glycerophosphorylcholine (GPC), glycine, glycochenodeoxycholate, glycochenodeoxycholate-sulfate, glycocholate, glycodeoxycholate, glycodeoxycholate-sulfate, glycohyocholate, glycolate (hydroxyacetate), glycolithocholate, glycoursodeoxycholate, glycylleucine, glycylproline, glycylvaline, guanosine, gulono-1,4-lactone, hexadecanedioate, hexanoylcarnitine (C6), hexanoylglycine, hippurate, histidine, histidylalanine, homoserine, homostachydrine, HWESASLLR, HWESASXX, hydantoin-5-propionic acid, hypoxanthine, indole-3-carboxylic acid, inosine, inositol 1-phosphate (I1P), Isobar: betaine aldehyde, N-methyldiethanolamine, Isobar: fructose 1,6-diphosphate, glucose 1,6-diphosphate, myo-inositol 1,4 or 1,3-diphosphate, isobutyrylcarnitine, isoleucine, isoleucylglycine, isoleucylvaline, isopalmitic acid, isovalerate (C5), isovalerylcarnitine, isovalerylglycine, kojibiose, kynurenate, kynurenine, lactate, laurate (12:0), laurylcarnitine (C12), leucine, leucylalanine, leucylleucine, linoleate (18:2n6), linolenate [alpha or gamma] (18:3n3 or 6), linoleoylcarnitine, lysine, malate, maleate, maltopentaose, maltose, maltotetraose, maltotriose, mannose, margarate (17:0), methionine, methionine sulfoxide, methionylalanine, methylsuccinate, myo-inositol, myristate (14:0), myristoleate (14:1n5), myristoleoylcarnitine, myristoylcarnitine, N(2)-furoyl-glycine, N1-methyladenosine, N2,N2-dimethylguanosine, N6-acetyllysine, N6-carbamoylthreonyladenosine, N6-methyladenosine, N-acetylalanine, N-acetylaspartate (NAA), N-acetyl-beta-alanine, N-acetylglutamate, N-acetylglycine, N-acetylleucine, N-acetylmethionine, N-formylmethionine, N-glycolylneuraminate, nicotinamide, nicotinamide adenine dinucleotide (NAD+), nonadecanoate (19:0), o-cresol-sulfate, octanoylcarnitine, oleate (18:1n9), oleate-vaccenate (18:1), oleic ethanolamide, Oleoyl ethanolamide, oleoylcarnitine (C18), oleoyl-ethanolamide, O-methylcatechol-sulfate, ophthalmate, ornithine, orotate, oxalate (ethanedioate), palmitate (16:0), palmitoleate, palmitoleate (16:1n7), palmitoyl ethanolamide, palmitoyl sphingomyelin (d18:1/16:0), palmitoylcarnitine (C16), palmitoyl-ethanolamide, pantothenate, pelargonate (9:0), pentadecanoate (15:0), phenylacetate, phenylacetylglycine, phenylalanine, phenylalanyllysine, phenylalanyltryptophan, phenyllactate (PLA), phenylpropionylglycine, phenylpyruvate, phosphoenolpyruvate (PEP), phosphoethanolamine, pipecolate, prolylglycine, prolylleucine, propionylcarnitine, pseudouridine, pyridoxate, pyrraline, pyruvate, quinate, ribitol, riboflavin (Vitamin B2), ribose, ribose 5-phosphate, ribulose, S-adenosylhomocysteine (SAH), sarcosine (N-Methylglycine), sebacate (decanedioate), serylleucine, serylphenylalanine, seryltyrosine, S-methylglutathione, sorbitol, spermidine, spermine, sphinganine, Sphinganine-1-phosphate, sphingosine, sphingosine 1-phosphate, stachydrine, stearate (18:0), stearidonate (18:4n3), stearoylcarnitine (C18), stearoyl-ethanolamide, suberylglycine, succinate, succinimide, succinylcarnitine, tagatose, tartronate (hydroxymalonate), taurine, tauro-beta-muricholate, taurochenodeoxycholate, taurocholate, taurodeoxycholate, tauroursodeoxycholate, tetradecanedioate, threonine, thymine, tiglylcarnitine, trans-4-hydroxyproline, trigonelline (N'-methylnicotinate), tryptophan, undecanedioate, uracil, urate, urea, uridine, valerylglycine, valine, valylglycine, valylvaline, xanthine, xylonate and the biomarkers cysteinylglycine, sphinganine-1-phosphate, and combinations thereof and to detect sample quality biomarkers present at aberrant levels in the sample, assessing the quality of the biological sample by associating the sample quality biomarkers determined to be aberrant with sample quality parameters and determining whether the sample meets acceptance criteria, and simultaneously performing metabolic profiling or biochemical analysis on the same sample.

20. The method of claim 19, wherein for a sample that is determined to meet quality acceptance criteria, the result of the metabolic profiling or biochemical analysis is used; and for a sample that is determined to not meet quality acceptance criteria, either not using the result of the metabolic profiling or biochemical analysis or modifying the result of the metabolic profiling or biochemical analysis based on the quality assessment results.

21. The method of claim 19, wherein determining whether a sample meets acceptance criteria includes assessing compliance with sample handling protocols and/or assessing subject compliance.

* * * * *